United States Patent [19]
Ohi et al.

[11] Patent Number: 5,998,452
[45] Date of Patent: Dec. 7, 1999

[54] BENZENE DERIVATIVES, COMPOSITIONS AND METHODS FOR TREATING ISCHEMIC DISEASES

[75] Inventors: Nobuhiro Ohi; Tatsuya Kato; Tomokazu Ozaki; Kazuhiko Tamura; Yoshiyuki Suzuki; Michitaka Akima, all of Shizuoka, Japan

[73] Assignee: Chugai Seiyaku Kabushiki Kaisha, Tokyo, Japan

[21] Appl. No.: 08/944,550

[22] Filed: Oct. 7, 1997

Related U.S. Application Data

[63] Continuation-in-part of application No. 08/448,492, Jun. 7, 1995, abandoned, application No. 08/860,274, Jun. 17, 1997, application No. PCT/JP94/01009, Jun. 23, 1994, and application No. PCT/JP95/02637, Dec. 22, 1995.

[30] Foreign Application Priority Data

Jun. 23, 1993 [JP] Japan ................................. 5-152248
Dec. 22, 1994 [JP] Japan ................................. 6-320862

[51] Int. Cl.$^6$ ..................... C07D 417/12; A61K 31/425
[52] U.S. Cl. ..................... 514/369; 544/369; 546/198; 546/209; 548/186; 548/122; 548/132; 548/136; 548/146; 548/264.4; 548/311.7; 549/438; 514/369
[58] Field of Search ..................... 548/186, 122, 548/132, 136, 146, 264.4, 311.7; 514/369; 544/369; 546/198, 209; 549/438

[56] References Cited

U.S. PATENT DOCUMENTS

| | | |
|---|---|---|
| 2,520,179 | 8/1950 | Surrey . |
| 2,623,048 | 12/1952 | Long et al. . |
| 3,309,377 | 3/1967 | Surrey . |

FOREIGN PATENT DOCUMENTS

| | | |
|---|---|---|
| 0515684 | 12/1992 | European Pat. Off. . |
| 0705816 | 4/1996 | European Pat. Off. . |
| 9002114 | 3/1990 | WIPO . |

OTHER PUBLICATIONS

Mahgoub, S.A. *Bull. Fac., Assuit Univ.,* 20(2–B), 1991, pp. 43–53.

Ehring, G.R. *Proc. West Pharmacol. Soc.,* vol. 24, pp. 221–224.

Ehring, G.R. *The Journal of Pharmacology and Experimental Therapeutics,* vol. 244, No. 2, 1988, pp. 479–492.

Journal of Heterocyclic Chemistry, vol. 29, 1992, Provo Us, pp. 1081–1084, XP002028431 R. Milicent et al.: "Cyclic transformations of 5–Aryl(or Benzyl–3–(2–bromoethyl–1, 3,4–oxadiazol–2(3H)–ones into 1–Aminoimidazolidin–2–one and 5,6–Dihydro–4H–1,3, 4–oxadiazine Derivatives" *p. 1082; examples, A,B,C; Table II*.

Journal of the American Chemical Society, vol. 73, 1967–1968, XP002028432 R.W. Bost et al.: "N–(beta–Aminoethyl)morpholine as a reagent for the characterization of esters" * p. 1968; table I*.

Helvetica Chimica Acta, vol. 39, 1956, Basel CH, pp. 607–618, XP002028433 H. J. Schmeid et al.: "Sterische und elektrostatische Effekte in der Schmidt–Reaktion" * p. 617, paragraph 5 *.

Journal of Organic Chemistry, vol. 26, 1961, Easton US, pp. 3414–3419, XP002028434 Shin Hayao et al.: "New sedative and hypertensive Phenylpiperazine Amides" * p. 3415, right–hand column; p. 3416, table II *.

Journal of the American Chemical Society, vol. 71, 1949, DC US, pp. 3105–3107, XP002028435 A.R. Surrey: "The preparation of 4–Thiazolidones. III. The reaction of Methyl Thioglycolate with benzylidene dialkylaminoalkylamines" * p. 3106; table II *.

Chemistche Berichte, vol. 70, No. 6, 1937, Weinheim DE, pp. 1230–1240, XP002028436 J.V. Braun et al.: "Synthese des Spermidins und analoger Traimine der Fettreihe" * p. 1240, paragraph 2 *.

Farmaco, Edizione Scientifica, vol. 35, No. 6, 1980, Pavia It, pp. 527–534, XP002028437 G. Mazonne et al.: "Derivati amminoetilici di alcuni 5–aril–1,3,4–ossadiazol–2–oni: sintesi e attivita farmacologica" *p. 532; table I*.

(List continued on next page.)

*Primary Examiner*—Robert Gerstl
*Attorney, Agent, or Firm*—Birch, Stewart, Kolasch & Birch, LLP.

[57] ABSTRACT

The present invention is directed to a compound represented by formula (I):

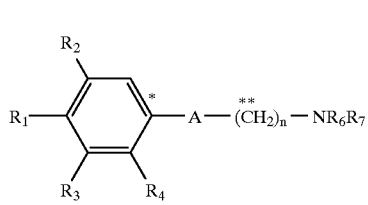

(I)

wherein, for example, $R_1$, $R_2$, $R_3$, and $R_4$ each represents a hydrogen atom; $R_6$ and $R_7$ each represent a substituted or unsubstituted lower alkyl group; A represents a group represented by formula (II):

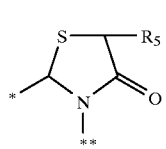

(II)

wherein $R_5$ represents, for example, a hydrogen atom; and n represents an integer of 2 to 6, or a stereoisomer or optical isomer thereof and a pharmaceutically acceptable salt thereof and compositions and methods for treating ischemic diseases. The compounds represented by formula (I) have an inhibitory action on calcium overload in addition to a vasorelaxing activity (calcium antagonism) and an inhibitory action on lipid peroxidation and are useful as a preventive or treating agent for ischemic diseases and hypertension.

46 Claims, 4 Drawing Sheets

OTHER PUBLICATIONS

"Synthesis and Ca$^{2+}$ Antagonistic Activity of 2–[2–[(Aminoalkyl)oxy]–5methoxyphenyl]–3, 4–dihydro–4–methyl–3–oxo–2H–1, 4–benzothiazines", Fujita et al., J.Med.Chem.1990, 33, 1989–1905.

"Some Arlyoxyalkylamines, N–Arylethylenediamines, and Related Compounds aws Anorectic Agents", Shadbolt et al., J.Med.Chem.1971, 14, 836–842.

"Design of 5–(3,5–Di–tert–butyl–4–hydroxyphenyl)–1,3, 4–thiadiazoles,–1,3,4–oxadiazoles, and –1,2,4–triazoles as Orally–Active, Nonulcerogenic Antiinflammatory Agentss", Mullican et al., J.Med.Chem. 1993, 1090–1099.

"Novel Calcium Antagonists. Synthesis and Structure–Activity Relationship Studies of Benzothiazoline Derivatives", Yamamoto et al., J.Med.Chem, 1988, 31, 920–930.

"Base–Induced Cycloaddition of Sulfonylmethyl Isocyanides to C,N Double Bonds. Synthesis of 1,5–Disubstituted and 1,4,5–Trisubstituted Imidazoles from Aldimines and Imidoyl Chlorides", van Leusen, et al., J.Org.Chem., 1977, 42, 1153–1159.

"A Novel, Convenient Synthesis of 2–Aryl–3–oxo–3, 4–dihydro–2H–1,4–benzothiazines", Fujita et al., Synthesis, Aug. 1988, 599–605.

"Synthesis and Antihistamic Activity of Some Thiazolidin–4–ones", Diurno et al., J.Med.Chem, 1992, 35, 2911–2912.

"Synthesis of B–Lactams by the Photochemical Extrusion of Sulfur Dioxide from 1,1–Dioxo–4–thiazolidinones", Johnson et al., J.Org.Chem., 48, 1983, 495–499.

Milcent, Rene et al., "Cyclic transformation of 5–aryl(or benzl)–3–(2–bromoethyl–1,3,4–oxadiazol–2(3H)–ones into 1–aminoimidazolindin–2–one and 5,6–dihydro–4H–1,3, 4–oxadiazine derivatives.", J. Heterocyclic Chem., vol. 29, pp. 1081–1084 (1992).

Bost, R.W. et al., "N–(Beta–aminoethyl)–morphine as a reagent for the characterization of esters.", J. Amer. Chem. Soc., vol. 73, pp. 1967–1968 (1951).

Hayao, Shin et al., "New sedative and hypotensive phenylpiperazine amides.", J. Organ. Chem., vol. 26, pp. 3414–3419 (1961).

Surrey, Alexander R., "The preparation of 4–thiazolidones. III. The reaction of methyl thioglycolate with benzylidene dialkylaminoalkaylamines.", J. Amer. Chem. Soc., vol. 71, pp. 3105–3107 (1949).

Mazzone, G. et al., "Derivati amminoetilici di alcuni 5–aril–1,3,4–ossadiazol–2–oni: sitesi e attivita famrmacologica.", Farmaco, Edizione Scientifica, vol. 35, No. 6, pp. 527–534 (1980).

Braum, J.V. et al., "Synthese des spermidus und analoger triamine der fettreihe.", Chemizhe Berichte, vol. 70, No. 6, pp. 1230–1240 (1937).

Schmid, H.J. et al., "Sterische und elektrostatische effekte in der Schmidt–reaktion.", Helvetica Chimica Acta, vol. 39,pp. 607–618 (1956).

Muhgoub, Bulletin Fac. Sci., Assiut Univ. 20, pp. 3143–3153 (1991), abstract only.

Debellis, Ric. Sci. Rend., Section 4(4) pp. 589–598 (1964), abstract only.

Mahgoub Bull Fac. Sci Assuit Univ. 20 (3143–53 1991 Abstract Only.

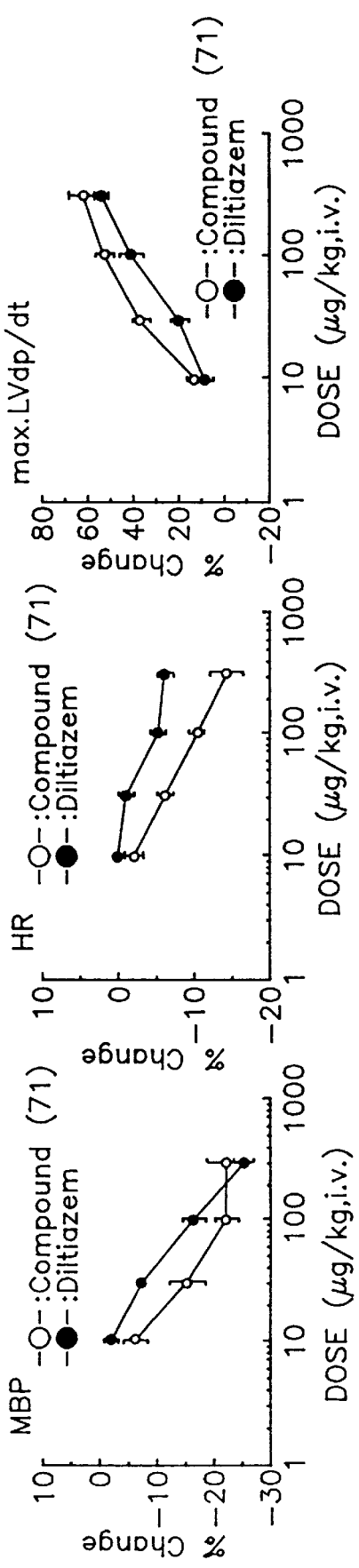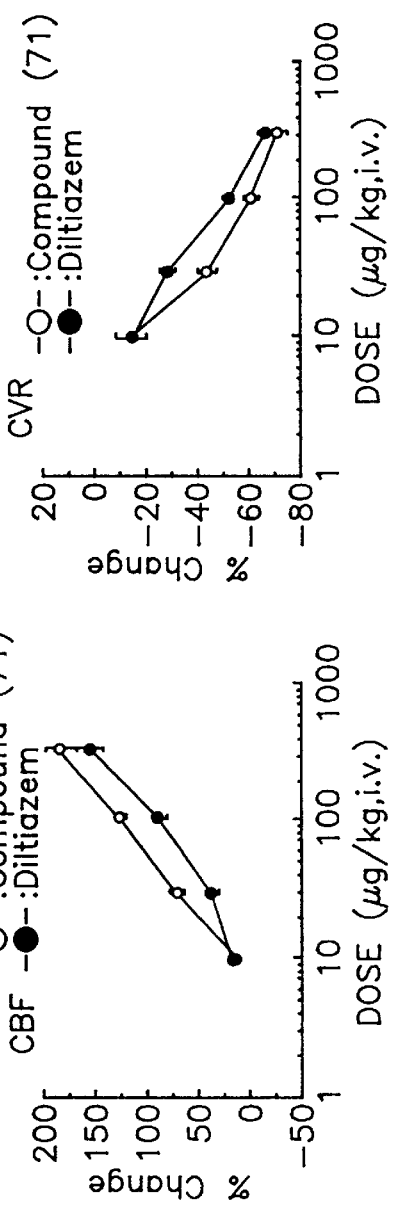

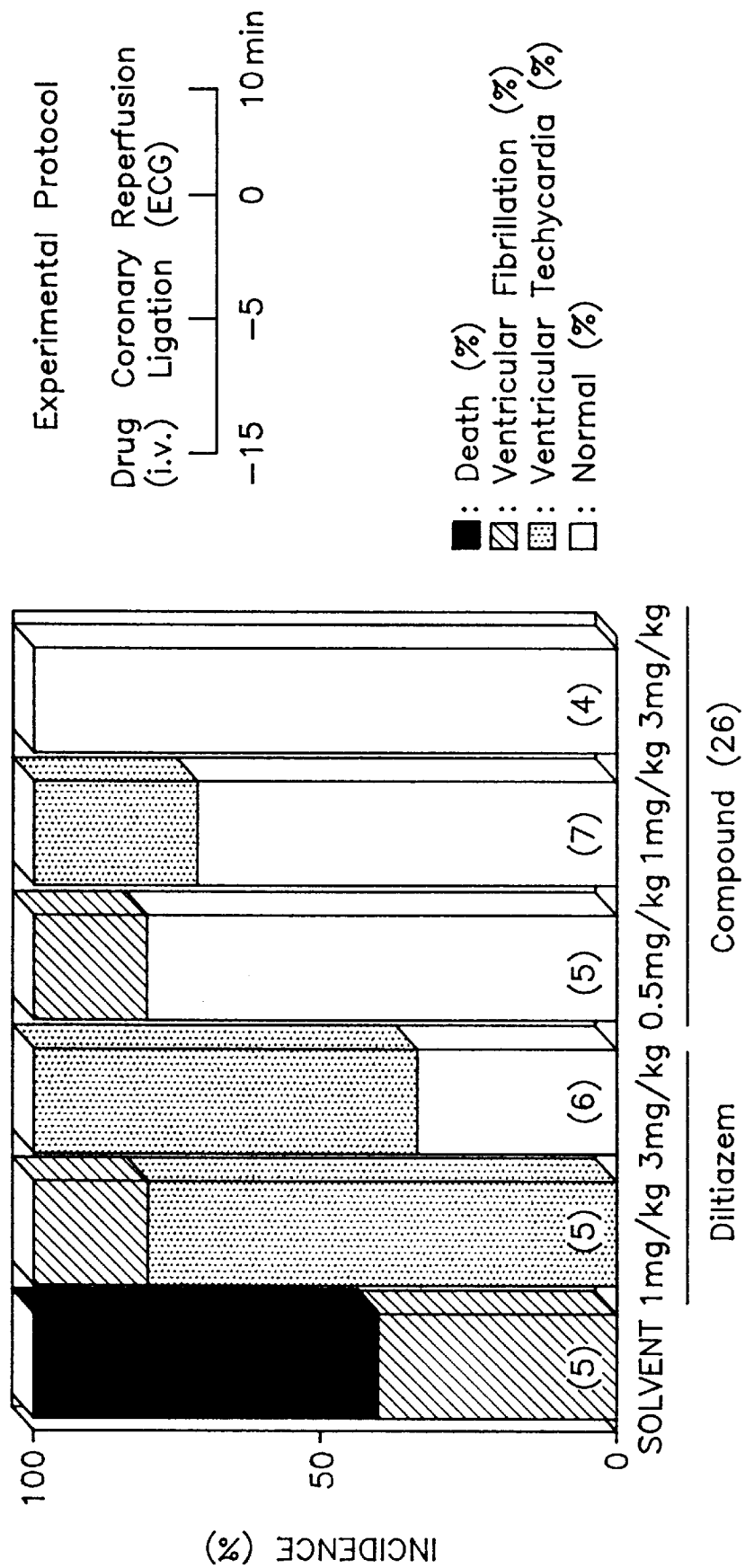

BENZENE DERIVATIVES, COMPOSITIONS AND METHODS FOR TREATING ISCHEMIC DISEASES

This application is a CIP of Ser. No. 08/448,492 Jun. 7, 1995 abandoned and Ser. No. 08/860,274 Jun. 17, 1997, PCT/JP94/01009 Jun. 23, 1994 and PCT/JP95/02637 Dec. 22, 1995, the entire contents of each of which are hereby incorporated by reference.

TECHNICAL FIELD

This invention relates to a preventive or therapeutic agent for ischemic diseases and an antihypertensive agent containing a compound represented by the general formula (I), a pharmaceutically acceptable salt thereof, a possible stereoisomer or optical isomer thereof as an active ingredient, which have an inhibitory action on calcium overload in addition to a vasorelaxing activity (calcium antagonism) and an inhibitory action on lipid peroxidation.

BACKGROUND OF THE INVENTION

The process of cell injuries owing to ischemia is broadly divided into two courses: (1) damages caused by reduction in intracellular ATP level or increase in intracellular calcium concentration etc. under insufficient oxygen supply during ischemia and (2) damages caused by increasing influx of calcium or production of free radicals, etc. followed by reperfusion or restoration of blood vessels after ischemia (Yoshiwara, et al., *Metabolism and disease*, 29, 379 (1992)). As typical ischemic diseases, cardiovascular diseases such as variant angina, unstable angina, myocardial infarction and arrythmia brought by reperfusion of coronary arteries by PTCA/PTCR/CABG, etc. or cerebrovascular diseases such as transient cerebroischemic attack, traumatic injury to the head and sequels after brain surgery can be given. In the treatment for variant angina or unstable angina, nitro compounds exemplified by nitroglycerin and nicorandil and calcium antagonists exemplified by diltiazem, nifedipine and verapamil are used and for the myocardial infarction or coronary reperfusion injury followed by PTCA/PTCR/CABG, etc., use of 5-lipoxygenase inhibitors or radical scavengers is under investigation. As a preventive or treating agent for ischemic cerebrovascular diseases, glyceol (registered trade mark), ozagrel, nizofenone, ticlopidine, nicaraven, etc. have been investigated and used with the idea of reducing the occurrence of cerebral edema or cerebrovascular spasms in the acute stage of cerebrovascular accident. In the chronic stage, cerebral circulation enhancers such as calcium antagonists exemplified by nicardipine, cinnarizine and flunarizine, cerebral circulation enhancers with promotive action for metabolism such as vinpocetine, nicergoline, pentoxifylline, and ifenprodil, or cerebral metabolic activators such as idebenone, GABA, and calcium hopantenate have been used in order to increase blood flow or improve the metabolic state in the tissue which survived the ischemic injury.

Based on extensive investigation to seek for an excellent preventive or therapeutic agent for ischemic diseases and an antihypertensive agent which would be able to suppress the generation of active oxygen species and increase of intracellular calcium concentration that are considered as the main causes of ischemic diseases and hypertension, the present inventors have synthesized the compounds represented by formula (I) and found that these compounds concurrently exhibit vasorelaxing activity (calcium antagonism), lipid peroxidation inhibitory action and calcium overload inhibitory action and that they are effective as a preventive or therapeutic agent for ischemic diseases and an antihypertensive agent. The present invention has been accomplished based on the findings.

Disclosure of the Invention

The present invention provides a therapeutic agent for ischemic diseases characterized by containing a compound represented by the general formula (I):

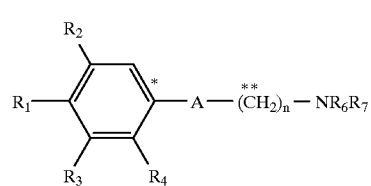

(I)

wherein $R_1$ represents a hydrogen atom, a hydroxyl group, an acyloxy group having 1 to 9 carbon atoms or a lower alkoxy group having 1 to 6 carbon atoms; $R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms; $R_4$ represents a hydrogen atom, a lower alkyl group having 1 to 6 carbon atoms; A represents a fragment represented by formula (II):

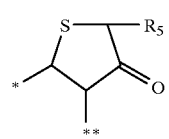

(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or $R_5$ forms a 5- or 6-membered ring containing two or more oxygen atoms or sulfur atoms, in which case the carbon atom to which it is bonded is a spiro atom; or a fragment represented by formula (III):

B (III)

wherein B represents a fragment selected from the group of following fragments represented by formulae (IV), (V), (VI), (VII), (VIII), (IX), (X), (XI), (XII), (XIII), (XIV), (XV), and (XVI):

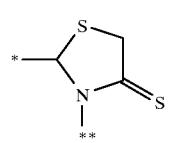

(IV)

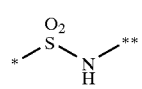

(V)

-continued (VI)
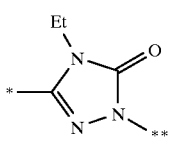

(VII)
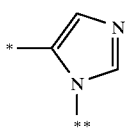

(VIII)
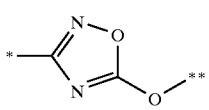

(IX)
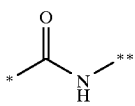

(X)
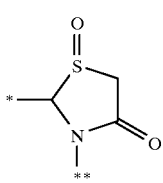

(XI)
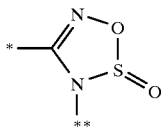

(XII)
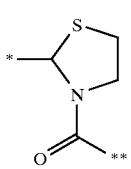

(XIII)
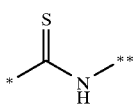

(XIV)
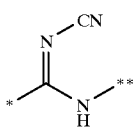

(XV)
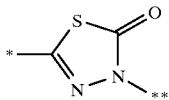

-continued (XVI)
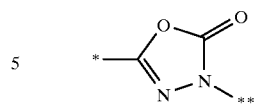

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, provided that $R_6$ and $R_7$ do not represent a methyl group simultaneously, or $R_6$ and $R_7$ are taken together to form a substituted or unsubstituted ring which may be a condensed ring; and n represents an integer of 2, 3, 4, 5 or 6; or a pharmaceutically acceptable salt thereof or a possible stereoisomer or optical isomer thereof as an active ingredient.

In the compounds represented by the general formula (I), examples of the substituents which may be present on the lower alkyl group having 1 to 6 carbon atoms, lower alkenyl group having 1 to 6 carbon atoms, lower alkoxy group having 1 to 6 carbon atoms, aryl group or heterocyclic group include halogen atoms such as chlorine and bromine atoms; a hydroxyl group; a carboxyl group; alkoxycarbonyl groups such as methoxycarbonyl and ethoxycarbonyl groups; carbamoyl groups such as N,N-dimethylcarbamoyl group; alkoxy groups such as methoxy and ethoxy groups; phenoxy groups such as 3,4-methylenedioxyphenoxy, 3,4,5-trimethoxyphenoxy, 3,4-dimethoxyphenoxy and 4-methoxyphenoxy groups; and phenyl groups such as 3,4-methylenedioxyphenyl and 4-methoxyphenyl groups.

BRIEF DESCRIPTION OF THE DRAWINGS

FIG. 3 is a set of graphs which illustrate the actions of the compound of Example 71 and diltiazem on mean blood pressure (MBP), heart rate (HR), coronary blood flow (CBF), and maximal first derivative of left ventricular pressure (max. LVdp/dt) in anesthetized open-chest dogs.

FIG. 4 is a graph which illustrates the actions of the compound of Example 26 and diltiazem on incidence of arrhythmias induced by coronary ligation/reperfusion in rats.

BEST MODE FOR CARRYING OUT THE INVENTION

Figure 1A:
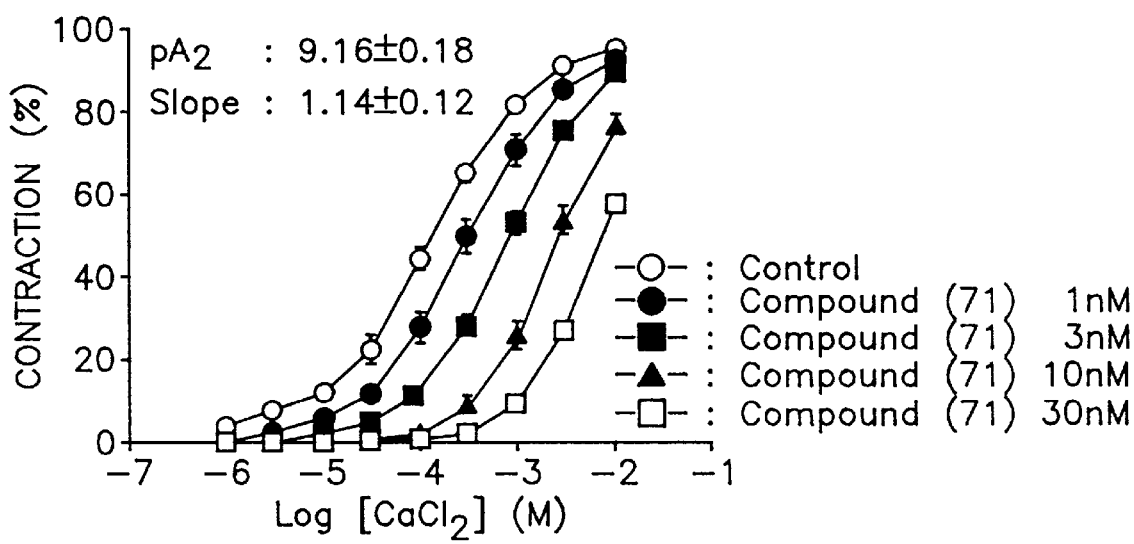
FIG. 1 is a set of graphs which illustrate the inhibitory actions of the compound of Example 71 and diltiazem on $CaCl_2$-induced contractions in isolated rat thoracic aorta.

Examples of the ischemic diseases to be treated by the present invention include ischemic heart diseases and ischemic cerebrovascular diseases. The term "a therapeutic agent for ischemic diseases", as used herein, means a preventive and/or therapeutic agent for these diseases. The therapeutic agents for ischemic heart diseases of the present invention include treating agents for angina pectoris, antihypertensive agents, antiarrhythmic agents, coronary vasodilators and myocardial infarction preventives. The therapeutic agents for ischemic cerebrovascular diseases of the present invention include therapeutic agents for cerebral infarction, cerebral circulation enhancers and cerebral protecting agents.

The pharmaceutically acceptable salts of the compound represented by the general formula (I) include, those with inorganic acids such as hydrochloric acid, sulfuric acid, nitric acid, hydrobromic acid and hydriodic acid; those with organic acids such as formic acid, acetic acid, oxalic acid, tartaric acid and fumaric acid; those with alkali metals such as sodium and potassium; those with alkaline earth metals such as calcium and magnesium, but the salts are not intended to be limited to the above examples so long as they are pharmaceutically acceptable.

The compound of the present invention or the pharmaceutically acceptable salt thereof may be administered orally or parenterally in the form of tablets, granules, subtilized granules, powders, capsules, syrups, elixirs, suspensions, emulsions or injections as formulated with a suitable excipient, auxiliary agent, lubricant, preservative, disintegrator, buffer, binder, stabilizer, humectant, emulsifier, colorant, flavour or fragrance, etc.

Dose of the compound of the present invention or the pharmaceutically acceptable salt thereof will vary depending on the physical constitution, age and condition of the patient, the severity of the disease and the elapsed time from manifestation of the disease. A daily dose in the range from 0.1 to 200 mg/body weight will be preferable. However, in general, blood concentration of the drug in a particular patient sometimes varies widely even if it is administered in an even dose and thus it is ideal that an optimum dose of the drug for a particular patient to be treated is determined by monitoring its blood concentration.

For a dosage form for oral administration, examples of auxiliary materials suitable for carrier include lactose, sucrose, sorbitol, mannitol, starches and their derivatives such as potato starch and corn starch, cellulose derivatives, and gelatin. The carrier may be used together with a lubricant such as magnesium stearate, carbowax or other polyethylene glycols. A mixture of these materials with the compound of the present invention or the pharmaceutically acceptable salt thereof may be formed into granules, tablets, capsules, etc. by a conventional method.

In preparing an aqueous dosage form, an effective amount of the active ingredient may be dissolved in water for injection and, if necessary, an antioxidant, stabilizer, solubilizer, buffer, preservative, etc. may be added to the solution. After a complete solution is formed, it may be filtered, dispensed and sealed in a conventional manner, and then sterilized by a high-pressure steam or hot-air sterilization method to prepare an injectable formulation.

In preparing a lyophilized dosage form, an injectable aqueous solution of the active ingredient may be lyophilized. Alternatively, an excipient that provides for easy lyophilization such as a saccharide or sugar alcohol such as mannitol, inositol, lactose, maltose or sucrose, or glycine, etc. may be added to the solution of the active ingredient, which is then lyophilized.

The compound represented by formula (I) can be prepared by the following processes A to Q.

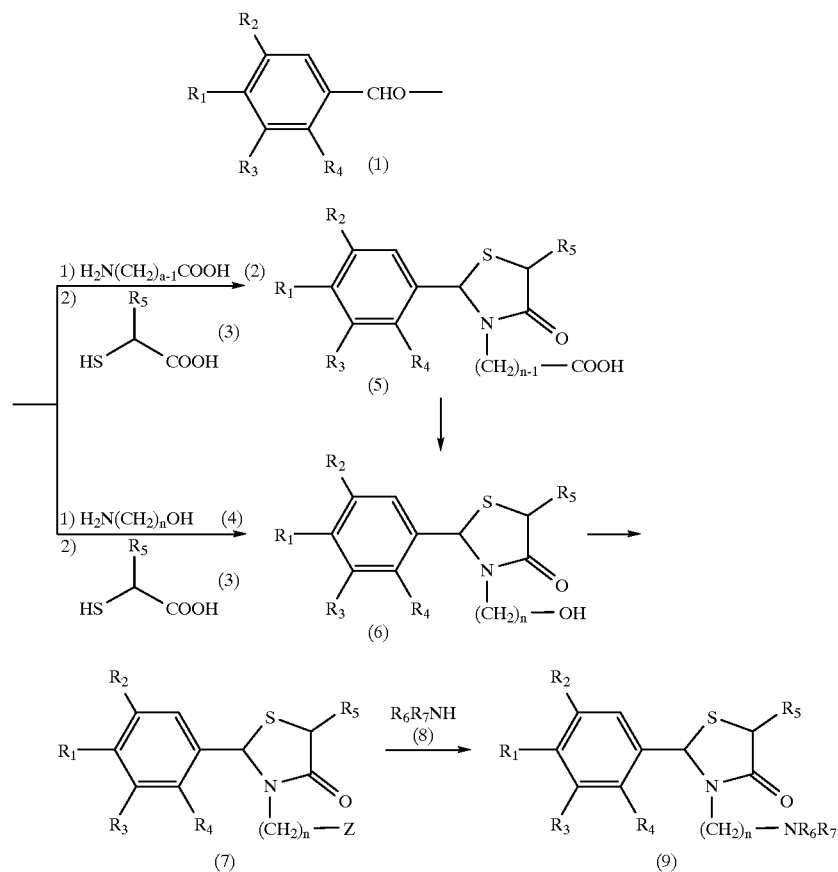

In the scheme of process A, $R_1$ represents a hydrogen atom, a hydroxyl group, an acyloxy group having 1 to 9 carbon atoms or a lower alkoxy group having 1 to 6 carbon atoms; $R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms; $R_4$ represents a hydrogen atom, a lower alkyl group having 1 to 6 carbon atoms; $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group; $R_6$ and $R_7$, which may be the same or different, each represent a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, provided that $R_6$ and $R_7$ do not represent a methyl group simultaneously, or $R_6$ and $R_7$ are taken together to form a substituted or unsubstituted ring which may be a condensed ring; n represents an integer of 2, 3, 4, 5 or 6; and Z represents a halogen atom.

Process B

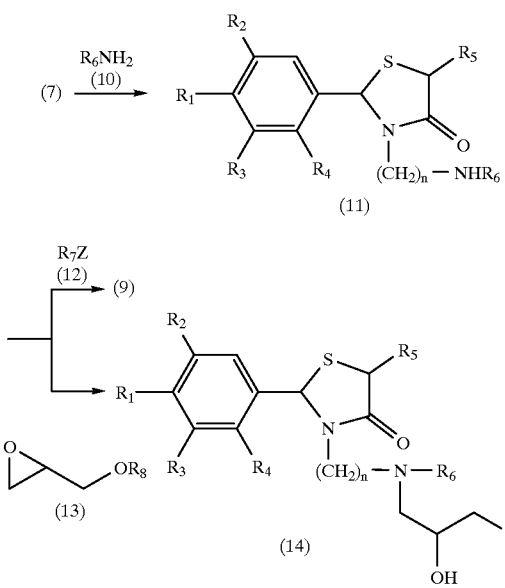

In the scheme of process B, $R_1$, $R_2$, $R_3$, $R_4$, $R_5$, $R_6$, $R_7$, and n are the same as defined previously; $R_8$ represents a substituted or unsubstituted aryl group or a substituted or unsubstituted heterocyclic group; and Z represents a chlorine atom or a bromine atom.

Process C

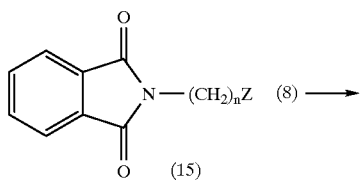

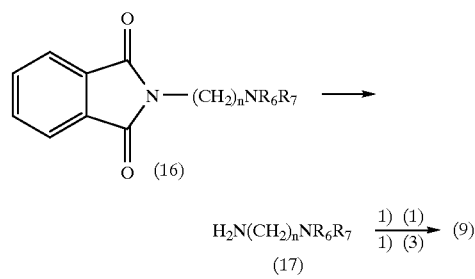

In the scheme of process C, $R_1$, $R_2$, $R_3$, $R_4$, $R_5$, $R_6$, $R_7$, n, and Z are the same as defined previously.

Process D

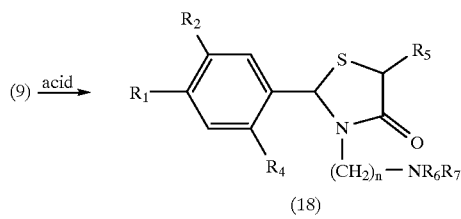

In the scheme of process D, $R_1$, $R_2$, $R_3$, $R_4$, $R_5$, $R_6$, $R_7$, and n are the same as defined previously.

Process E

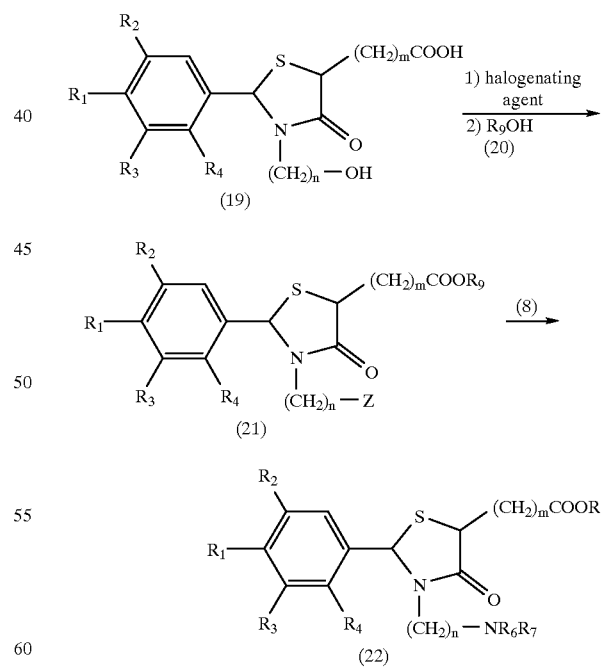

In the scheme of process E, $R_1$, $R_2$, $R_3$, $R_4$, $R_6$, $R_7$, n, and Z are the same as defined previously; $R_9$ represents an alkyl group having 1 to 6 carbon atoms; and m represents an integer of 1 to 7.

Process F

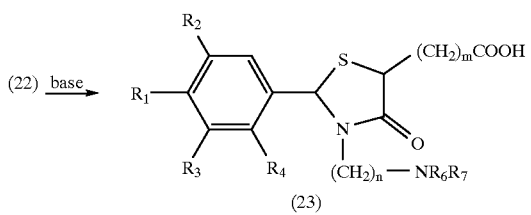

In the scheme of process F, $R_1$, $R_2$, $R_3$, $R_4$, $R_6$, $R_7$, $R_9$, n, and m are the same as defined previously.

Process G

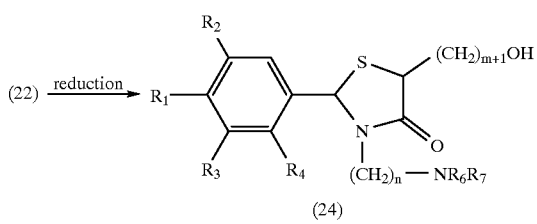

In the scheme of process G, $R_2$, $R_3$, $R_4$, $R_6$, $R_7$, $R_9$, n, and m are the same as defined previously.

Process H

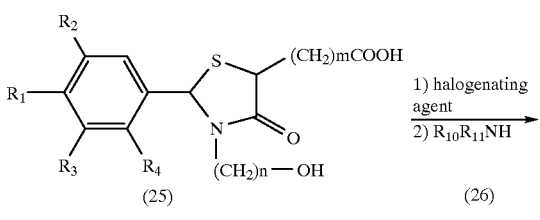

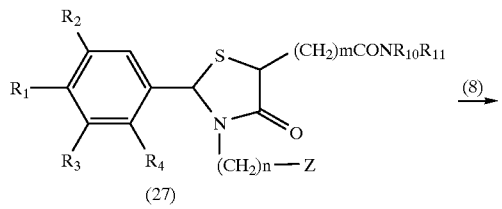

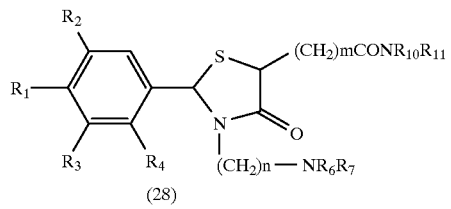

In the scheme of process H, $R_1$, $R_2$, $R_3$, $R_4$, $R_6$, $R_7$, Z, n, and m are the same as defined previously; and $R_{10}$ and $R_{11}$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, or $R_{10}$ and $R_{11}$ are taken together to form a substituted or unsubstituted ring which may be a condensed ring.

Process I

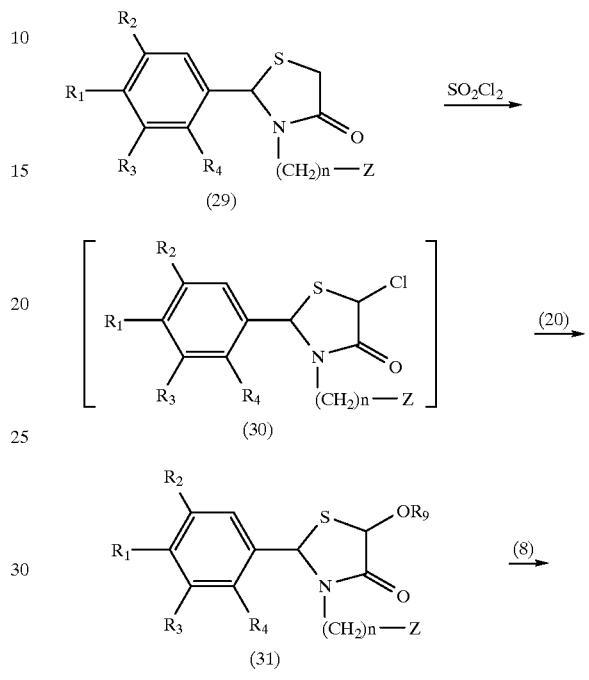

In the scheme of process I, $R_1$, $R_2$, $R_3$, $R_4$, $R_6$, $R_7$, Z, and n are the same as defined previously; and $R_9$ represents a substituted or unsubstituted lower alkyl group having 1 to 6 carbon atoms.

Process J

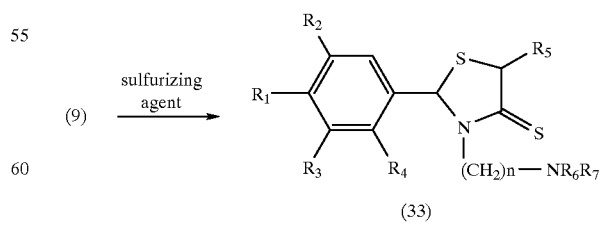

In the scheme of process J, $R_1$, $R_2$, $R_3$, $R_4$, $R_5$, $R_6$, $R_7$, and n are the same as defined previously.

Process K

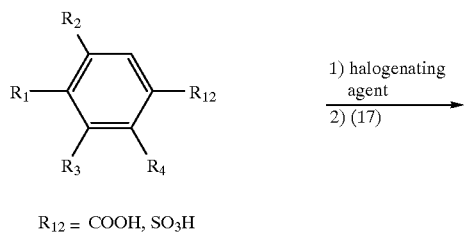

$R_{12}$ = COOH, SO$_3$H

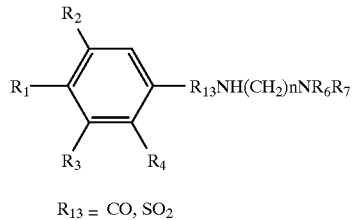

$R_{13}$ = CO, SO$_2$

In the scheme of process K, $R_1$, $R_2$, $R_3$, $R_4$, $R_6$, $R_7$, and n are the same as defined previously; $R_{12}$ represents a carboxyl group or a sulfo group; and $R_{13}$ represents a carbonyl group or a sulfonyl group.

Process L

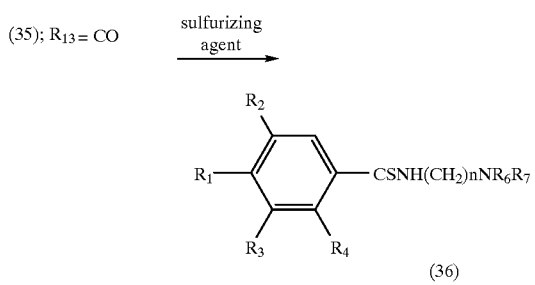

In the scheme of process L, $R_1$, $R_2$, $R_3$, $R_4$, $R_6$, $R_7$, and n are the same as defined previously; and $R_{13}$ represents a carbonyl group.

Process M

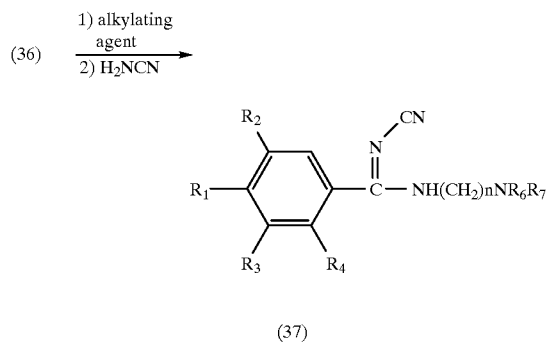

In the scheme of process M, $R_1$, $R_2$, $R_3$, $R_4$, $R_6$, $R_7$, and n are the same as defined previously.

Process N

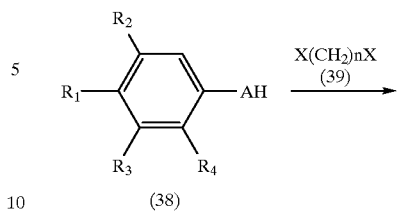

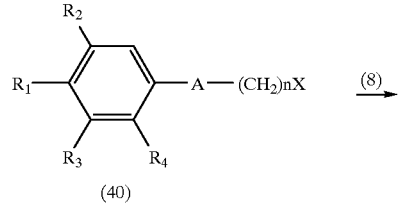

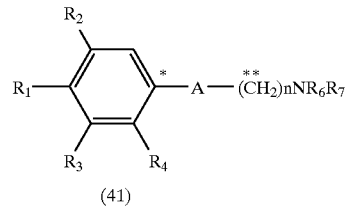

In the scheme of process N, $R_1$, $R_2$, $R_3$, $R_4$, $R_6$, $R_7$, and n are the same as defined previously; A represents a fragment selected from the group of following fragments represented by formulae (VI), (VIII), (XI), (XV), and (XVI):

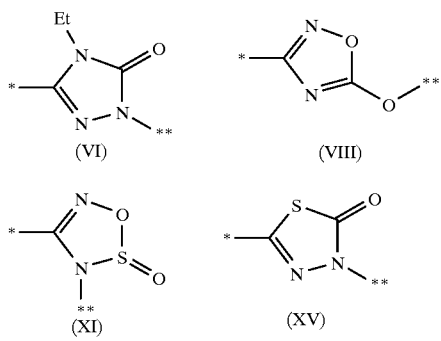

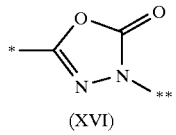

and X represents a chlorine atom or a bromine atom.

Process O

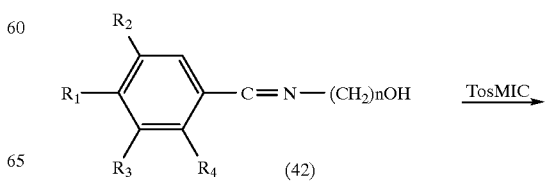

13
-continued

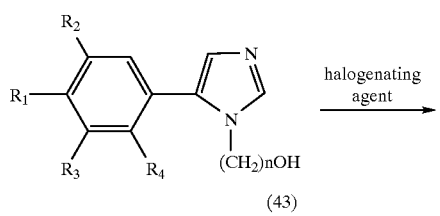

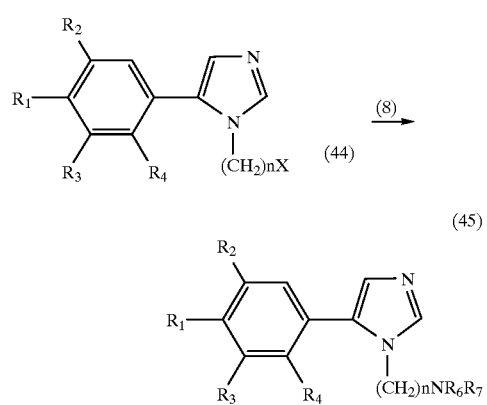

In the scheme of process O, $R_1$, $R_2$, $R_3$, $R_4$, $R_6$, $R_7$, n, and X are the same as defined previously.

Process P

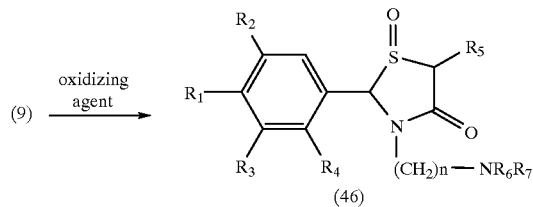

In the scheme of process P, $R_1$, $R_2$, $R_3$, $R_4$, $R_5$, $R_6$, $R_7$, and n are the same as defined previously.

Process O

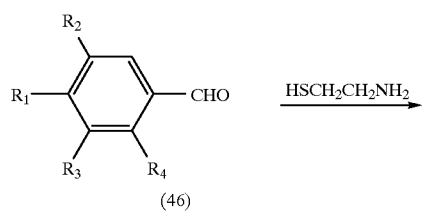

14
-continued

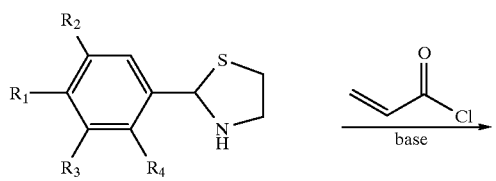

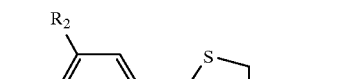

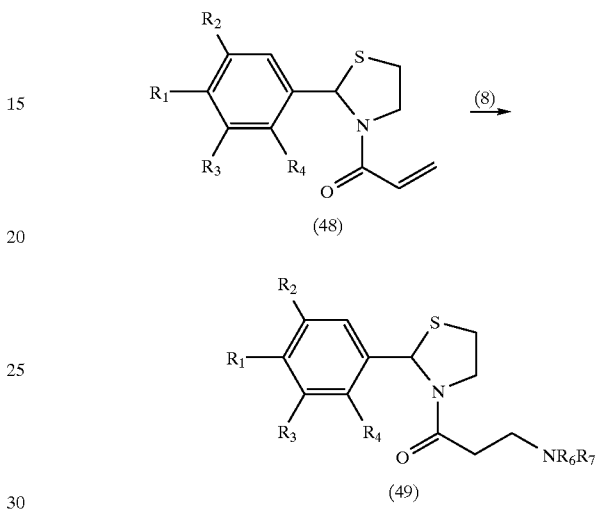

In the scheme of process Q, $R_1$, $R_2$, $R_3$, $R_4$, $R_5$, $R_6$, and $R_7$ are the same as defined previously.

The reaction conditions adopted in processes A to Q are tabulated below.

Process A:

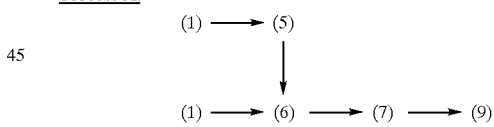

TABLE 1

Reaction Conditions for Each Step of Process A

| Step: | (1) → (5) | (1) → (6) | (5) → (6) | (6) → (7) | (7) → (9) |
|---|---|---|---|---|---|
| Solvent: | inert solvent (preferably benzene or toluene) | the same as the left | inert solvent (preferably tetrahydrofuran or toluene) | inert solvent (preferably dichloromethane, chloroform or diethyl ether) | inert solvent (preferably acetone, acetonitrile, DMF or DMSO) |
| Reaction Temperature: | room temperature to reflux | the same as the left | −20° C. to reflux (prefer- | −10° C. to reflux | −10° C. to reflux |

TABLE 1-continued

Reaction Conditions for Each Step of Process A

| | (preferably refluxing) | | ably −10° C. to room temperature) | (preferably room temperature to reflux) | (preferably room temperature to reflux) |
|---|---|---|---|---|---|
| Reaction Time: | 0.5 to 24 hrs (preferably 3 to 12 hrs) | 0.5 to 24 hrs (preferably 1 to 5 hrs) | 0.5 to 24 hrs (preferably 1 to 6 hrs) | 0.5 to 24 hrs (preferably 1 to 7 hrs) | 1 to 48 hrs (preferably 5 to 24 hrs) |
| Others: | * | | ** | halogenating agent (preferably phosphorus tribromide or thionyl chloride) | inorganic base (preferably potassium carbonate or sodium carbonate)*** |

Note:
*: Racemic mixture of (5) can be separated using an optically active organic base such as brucine, cinchonidine, ephedrine or quinine, to give an optically active form of (5).
**: While any method generally employed for reduction of a carboxylic acid to an alcohol can be used, the reaction is preferably carried out by once converting (5) to a mixed anhydride using ethyl chlorocarbonate, etc., followed by reduction with NaBH$_4$. NaBH$_4$ is used in an amount of 1 to 30 molar equivalents, preferably 10 molar equivalents.
***: The reaction is preferably carried out in the presence of potassium iodide.

Process B:

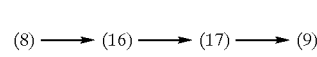

TABLE 2

Reaction Conditions for Each Step of Process B

| Step: | (7) → (11) | (11) → (9) | (11) → (14) |
|---|---|---|---|
| Solvent: | inert solvent (preferably acetonitrile or acetone) | the same as the left | the same as the left |
| Reaction Temperature: | 0° C. to reflux (preferably room temperature to reflux) | the same as the left | the same as the left |
| Reaction Time: | 2 to 48 hrs (preferably 5 to 24 hrs) | the same as the left | the same as the left |
| Base: | | inorganic base (preferably potassium carbonate or sodium carbonate)* | |

Note: *: The reaction is preferably carried out in the presence of potassium iodide.

Process C:

(8) → (16) → (17) → (9)

TABLE 3

Reaction Conditions for Each Step of Process C

| Step: | (8) → (16) | (16) → (17) | (17) → (9) |
|---|---|---|---|
| Solvent: | inert solvent (preferably acetonitrile or acetone) | alcoholic solvent (preferably methanol or ethanol) | inert solvent (preferably benzene or toluene) |

TABLE 3-continued

Reaction Conditions for Each Step of Process C

| Reaction Temperature | 0° C. to reflux (preferably room temperature to reflux) | −10° C. to 50° C. (preferably 0° C. to room temperature) | room temperature to reflux (preferably reflux) |
|---|---|---|---|
| Reaction Time: | 0.5 to 24 hrs (preferably 1 to 5 hrs) | 2 to 48 hrs (preferably 6 to 24 hrs) | 0.5 to 24 hrs (preferably 1 to 5 hrs) |
| Base: | inorganic base (preferably potassium carbonate or sodium carbonate | organic amine (preferably methylamine or ethylamine) or hydrizine hydrate | |

Process D:

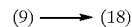

TABLE 4

Reaction Conditions for Process D

| Step: | (9) → (18) |
|---|---|
| Solvent: | water or acid (the acid is preferably acetic acid or hydrochloric acid) |
| Reaction Temperature: | −10° C. to reflux (preferably 0 to 50° C.) |
| Reaction Time: | 2 to 15 days (preferably 4 to 10 days) |
| Acid: | inorganic acid (preferably 47% hydrobromic acid) |

Process E:

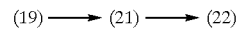

TABLE 5

Reaction Conditions for Each Step of Process E

| Step: | (19) → (21) | (21) → (22) |
|---|---|---|
| Solvent: | inert solvent (preferably dichloromethane, chloroform or diethyl ether) | inert solvent (preferably acetone, acetonitrile, DMF or DMSO) |
| Reaction Temperature | −10° C. to reflux (preferably room temperature to reflux) | −10° C. to reflux (preferably room temperature to reflux) |
| Reaction Time: | 0.5 to 48 hrs (preferably 4 to 24 hrs) | 1 to 48 hrs (preferably 5 to 24 hrs) |
| Reagent: | halogenating agent (preferably phosphorus tribromide or thionyl chloride) | inorganic base (preferably potassium carbonate or sodium carbonate)* |

Note: *: The reaction is preferably carried out in the presence of potassium iodide.

Process F:

     (22) ⟶ (23)

TABLE 6

Reaction Conditions for Process F [(22) → (23)]

| Solvent: | water or alcoholic solvent (preferably aqueous methanol or aqueous ethanol) |
|---|---|
| Reaction Temperature: | −10° C. to reflux (preferably room temperature to reflux) |
| Reaction Time: | 1 to 48 hrs (preferably 6 to 24 hrs) |
| Base or Acid: | aqueous solution of inorganic base, e.g., sodium hydroxide or potassium hydroxide, or inorganic acid, e.g., sulfuric acid or hydrochloric acid |

Process G:

     (22) ⟶ (24)

TABLE 7

Reaction Conditions for Process G [(22) → (24)]

| Solvent: | inert solvent (preferably THF, diethyl ether or toluene) |
|---|---|
| Reaction Temperature: | −78° C. to reflux (preferably −78° C. to room temperature) |
| Reaction Time: | 0.1 to 24 hrs (preferably 1 to 5 hrs) |
| Reducing Agent: | lithium aluminum hydride, lithium borohydride, DIBAL, borane-THF complex, etc. |

Process H:

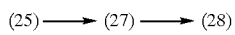     (25) ⟶ (27) ⟶ (28)

TABLE 8

Reaction Conditions for Each Step of Process H

| Step: | (25) → (27) | (27) → (28) |
|---|---|---|
| Solvent: | inert solvent (preferably dichloromethane, chloroform or diethyl ether) | inert solvent (preferably acetone, acetonitrile, DMF or DMSO) |
| Reaction Temperature | −10° C. to reflux (preferably 0° C. to reflux) | −10° C. to reflux (preferably room temperature to reflux) |
| Reaction Time: | 0.5 to 24 hrs (preferably 2 to 12 hrs) | 1 to 48 hrs (preferably 5 to 24 hrs) |
| Reagent: | halogenating agent (preferably thionyl chloride) | inorganic base (preferably potassium carbonate or sodium carbonate)* |

Note: *:The reaction is preferably carried out in the presence of potassium iodide.

Process I:

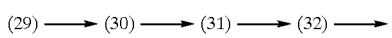     (29) ⟶ (30) ⟶ (31) ⟶ (32) ⟶

TABLE 9

Reaction Conditions for Each Step of Process I

| Step: | (29) → (30) | (30) + (20) → (31) | (31) + (8) → (32) |
|---|---|---|---|
| Solvent: | inert solvent (preferably dichloromethane, chloroform or diethyl ether) | the same as the left | inert solvent (preferably acetone, acetonitrile, DMF or DMSO) |
| Reaction Temperature | −5° C. to reflux (preferably 5° C. to room temperature) | the same as the left | −10° C. to reflux (preferably temperature to reflux) |
| Reaction Time: | 0.5 to 12 hrs (preferably 1 to 3 hrs) | 2 to 72 hrs (preferably 6 to 24 hrs) | 1 to 48 hrs (preferably 5 to 24 hrs) |
| Others: | halogenating agent (preferably sulfuryl chloride) | | inorganic base (preferably potassium carbonate or sodium carbonate)* |

Note: *:The reaction is preferably carried out in the presence of potassium iodide.

Process J:

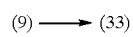     (9) ⟶ (33)

TABLE 10

Reaction Conditions for Process J [(9) → (33)]

| Solvent: | inert solvent (preferably dichloromethane, chloroform or THF) |
|---|---|
| Reaction Temperature: | −10° C. to reflux (preferably 0 to 50° C.) |

TABLE 10-continued

Reaction Conditions for Process J [(9) → (33)]

| | |
|---|---|
| Reaction Time: | 0.5 to 48 hrs (preferably 2 to 10 hrs) |
| Reagent: | sulfurizing agent (preferably phosphorus pentasulfide or Lawesson's reagent) |

Process K:

(34) ⟶ (35)

TABLE 11

Reaction Conditions for Process K [(34) → (35)]

| | |
|---|---|
| Solvent: | inert solvent (preferably THF, diethyl ether or dichloromethane chloroform) |
| Reaction Temperature: | −10° C. to reflux (preferably 0° C. to reflux) |
| Reaction Time: | 0.5 to 48 hrs (preferably 1 to 24 hrs) |
| Halogenating Agent: | thionyl chloride, oxalyl chloride, phosphorus trichloride, phosphorus tribromide, etc. (Note: The reaction is preferably carried out in the presence of catalytic amount of DMF.) |
| Base: | inorganic base or organic base (preferably pyridine or triethylamine) |

Process L:

(35) ⟶ (36)

TABLE 12

Reaction Conditions for Process L [(35) → (36)]

| | |
|---|---|
| Solvent: | inert solvent (preferably dichloromethane or chloroform) |
| Reaction Temperature: | −10° C. to reflux (preferably 0 to 50° C.) |
| Reaction Time: | 0.5 to 48 hrs (preferably 2 to 10 hrs) |
| Sulfurizing Agent: | phosphorus pentasulfide or Lawesson's reagent |

Process M:

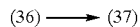
(36) ⟶ (37)

TABLE 13

Reaction Conditions for Process M [(36) → (37)]

| | |
|---|---|
| Solvent: | inert solvent (preferably THF) |
| Reaction Temperature: | −10° C. to reflux (preferably 0° C. to reflux) |
| Reaction Time: | 1 to 48 hrs (preferably 5 to 24 hrs) |
| Base: | inorganic base or organic base (preferably |

TABLE 13-continued

Reaction Conditions for Process M [(36) → (37)]

| | |
|---|---|
| | sodium hydride or lithium diisopropylamide) |
| Alkylating Agent: | alkyl halide (preferably ethyl iodide) |

Process N:

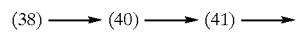
(38) ⟶ (40) ⟶ (41) ⟶

TABLE 14

Reaction Condition for Each Step of Process N

| Step: | (38) → (40) | (40) → (41) |
|---|---|---|
| Solvent: | inert solvent (preferably DMF, DMSO, acetone or acetonitrile) | inert solvent (preferably acetone or acetonitrile) |
| Reaction Temperature | −10° C. to reflux (preferably room temperature to reflux) | −10° C. to reflux (preferably room temperature to reflux) |
| Reaction Time: | 0.5 hr to 4 days (preferably 3 hrs to 3 days) | 1 to 48 hrs (preferably 5 to 24 hrs) |
| Base: | inorganic base (preferably potassium carbonate or sodium carbonate) | inorganic base (preferably potassium carbonate or sodium carbonate)* |

Note: *:The reaction is preferably carried out in the presence of potassium iodide.

Process O:

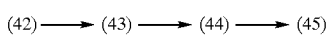
(42) ⟶ (43) ⟶ (44) ⟶ (45)

TABLE 15

Reaction Conditions for Each Step of Process O

| Step: | (42) → (43) | (43) → (44) | (44) → (45) |
|---|---|---|---|
| Solvent: | inert solvent (preferably methanol or ethanol) | inert solvent (preferably dichloro-methane, chloroform or diethyl ether) | inert solvent (preferably DMF, DMSO, acetone or acetonitrile) |
| Reaction Temperature: | 0° C. to reflux (preferably room temperature to reflux) | −10° C. to reflux (preferably room temp. to reflux) | −10° C. to reflux (preferably room temperature to reflux) |
| Reaction Time: | 1 to 24 hrs (preferably 5 to 20 hrs) | 0.5 to 24 hrs (preferably 1 to 7 hrs) | 1 to 48 hrs (preferably 5 to 24 hrs) |
| Reagent: | inorganic base (preferably potassium carbonate or sodium carbonate) | halogenating (preferably phosphorus tribromide or thionyl chloride | inorganic base (preferably potassium carbonate or sodium carbonate)* |

Note: *:The reaction is preferably carried out in the presence of potassium iodide.

Process P:

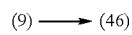

TABLE 16

Reaction Conditions for Process P [(9) → (46)]

| Step: | (9) → (46) |
|---|---|
| Solvent: | organic acid (preferably acetic acid) |
| Reaction Temperature: | −5 to 40° C. (preferably room temperature) |
| Reaction Time: | 0.5 to 48 hrs (preferably 6 to 12 hrs) |
| Oxidizing Agent: | hydrogen peroxide or organic peracid |

Process Q:

TABLE 17

Reaction Conditions for Each Step of Process O

| Step: | (1) → (47) | (47) → (48) | (48) → (49) |
|---|---|---|---|
| Solvent: | inert solvent (preferably methanol or THF) | inert solvent (preferably THF or dichloromethane) | inert solvent (preferably THF or chloroform) |
| Reaction Temperature | −10° C. to reflux (preferably 0° C. to room temperature) | −10° C. to reflux (preferably 0° C. to room temperature) | 0° C. to reflux temperature (preferably room temperature to reflux) |
| Reaction Time: | 0.5 to 48 hrs (preferably 1 to 5 hrs) | 0.5 to 24 hrs (preferably 1 to 5 hrs) | 0.5 to 24 hrs (preferably 1 to 5 hrs) |
| Base: | | inorganic base or organic base (preferably pyridine or triethylamine) | |

The compound of formula (I) according to the present invention contains one or two asymmetric carbon atoms in the structure thereof, and the pure stereoisomers or optical isomers can be obtained by methods known in the art. For example, each enantiomer can be separated by chromatography using an HPLC column for optical resolution or by fractional crystallization utilizing an optically active acid, preferably (R)-(−)-1,1'-binaphthyl-2,2'-diyl hydrogen phosphate. The above-mentioned techniques for separation of optical isomers are applied to not only a final product but also an intermediate having a carboxyl group. In the latter case, commonly used optically active bases such as brucine can be employed. Similarly, diastereomeric mixtures comprising both cis- and trans-stereoisomers can be separated to each optical isomer, i.e., cis(+), cis(−), trans(+) and trans(−), by conventional methods known to those skilled in the art.

As a matter of course, the stereoisomers and optical isomers of the compound of formula (I) are also included in the scope of the present invention.

EXAMPLES

The present invention will now be illustrated in greater detail by referring to reference examples, examples, and pharmacological test examples, which are not intended as a limitation of the invention.

In the following reference examples, examples, and tables 18 to 34 inclusive the NMR data were measured with JEOL JNM-FX200 or JEOL JNM-EX270 except those with asterisk, in which case the measurements were carried out on Hitachi R-24B (60 MHz).

Reference Example 1

Preparation of 2-(3,5-Diisopropyl-4-hydroxyphenyl)-3-(3-hydroxypropyl)-1,3-thiazolidin-4-one In benzene (50 ml) were suspended 3,5-diisopropyl-4-hydroxybenzaldehyde (5.00 g) and 3-aminopropanol (1.82 g) in a nitrogen atmosphere. A Dean-Stark trap was fitted to the reactor, and the suspension was refluxed for 1.5 hours. After allowing the mixture to cool, α-mercaptoacetic acid (2.23 g) was added, then the mixture was further refluxed for 2 hours. After removal of benzene by evaporation, water (50 ml) was added to the residue, and the mixture was extracted with chloroform. The organic layer was dried over anhydrous sodium sulfate, and the solvent was removed under reduced pressure. The residue was purified by silica gel column chromatography (eluent; chloroform-methanol, 99:1) to afford 1.97 g (24%) of the title compound as a colorless oil. NMR (CDCl$_3$, 60 MHz): 1.23 (12H, d, J=6.6 Hz), 1.0–1.8 (2H, m), 2.5–3.8 (7H, m), 3.73 (2H, brs), 5.50 (2H, brs), 6.92 (2H, s)

Each alcohol shown in Tables 18 to 20 was prepared according to the procedure for Reference Example 1, using an appropriate substituted benzaldehyde and a corresponding ω-aminoalkyl alcohol instead of 3,5-diisopropyl-4-hydroxybenzaldehyde and 3-aminopropanol in each case.

TABLE 18

[Structure: 2-R¹-3-(CH₂)ₙ-OH-thiazolidin-4-one]

| Ref. Ex. No. | R¹ | n | Physical Properties (¹H-NMR (CDCl₃)) |
|---|---|---|---|
| 2 | 4-hydroxyphenyl | 3 | 1.3–1.7(2H, m), 2.0(1H, brs), 2.9–3.2 (1H, m), 3.3–3.8(3H, m), 3.74 and 3.82 (2H, ABq, J=16.0Hz), 5.57(1H, s), 6.84 (2H, d, J=8.0Hz), 7.20(2H, d, J=8.0Hz), 7.26(1H, brs) |
| 3 | 2,6-dimethyl-4-hydroxyphenyl | 3 | 1.4–1.7(2H, m), 1.68(1H, brs), 2.26 (6H, s), 2.9–3.1(1H, m), 3.2–3.3(1H, m) 3.4–3.8(2H, m), 3.73 and 3.86(2H, ABq, J=16.0Hz), 5.04(1H, brs), 5.48(1H, s), 6.92(2H, s) |
| 4 | 2,3,5,6-tetramethyl-4-hydroxyphenyl * | 3 | 1.58(2H, quint, J=6.0Hz), 2.17(9H, s), 2.6–3.9(5H, m), 3.70(2H, brs), 5.43 (1H, s), 5.83(1H, brs), 6.72(1H, s) |
| 5 | 2,6-diethyl-4-hydroxyphenyl * | 3 | 1.20(6H, t, J=7.5Hz), 1.0–1.7(2H, m), 2.55(4H, q, J=7.5Hz), 2.8–3.6(5H, m), 3.77(2H, brs), 5.27(1H, brs), 5.47 (1H, brs), 6.87(2H, s) |
| 6 | 2-tert-butyl-6-methyl-4-hydroxyphenyl * | 3 | 1.35(9H, s), 1.0–2.1(2H, m), 2.22(3H, s), 2.7–3.8(5H, m), 3.72(2H, brs), 5.27(1H, brs), 5.43(1H, brs), 6.8–7.2 (2H, m) |
| 7 | 2,6-dimethoxy-4-hydroxyphenyl | 3 | 1.4–1.7(2H, m), 2.9–3.2(1H, m), 3.3–4.1(4H, m), 3.72 and 3.85(2H, ABq, J=16.0 Hz), 3.89(6H, s), 5.55(1H, s), 6.07 (1H, brs), 6.56(2H, s) |
| 8 | 2,6-dichloro-4-hydroxyphenyl * | 3 | 1.67(2H, quint, J=6.0Hz), 2.7–4.0(7H, m), 5.47(1H, s), 6.87(1H, s), 7.17 (2H, s) |

TABLE 19
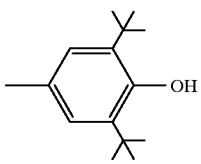
| Ref. Ex. No. | R¹ | n | Physical Properties (¹H-NMR (CDCl₃)) |
|---|---|---|---|
| 9 | 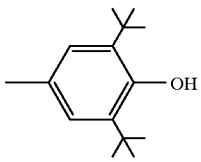 | 4 | 1.37(18H, s), 1.2–1.9(4H, m), 2.6–3.2 (2H, m), 3.3–3.4(3H, m), 3.67(2H, brs), 5.30(1H, brs), 5.53(1H, brs), 7.00(2H, s) |
| 10 | 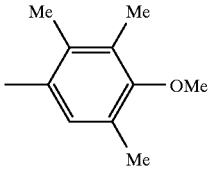 | 5 | 1.40(18H, s), 1.0–1.8(6H, m), 2.23(1H, s), 2.4–3.0(1H, m), 3.2–3.8(3H, m), 3.68(2H, brs), 5.33(1H, s), 5.53(1H, brs), 7.03(2H, s) |
| 11 | 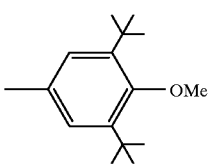 | 3 | 1.65(2H, qunit, J=6.0Hz), 2.20(9H, brs) 2.5–4.2(7H, m), 3.67(3H, s), 5.87(1H, s), 6.77(1H, s) |
| 12 |  | 3 | 1.40(18H, s), 1.2–1.7(2H, m), 2.8–3.7 (5H, m), 3.65(3H, s), 3.72(2H, brs), 5.50(1H, brs), 7.13(2H, s) |

TABLE 20

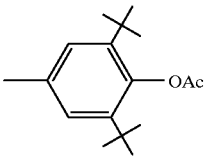

| Ref. Ex. No. | R¹ | n | Physical Properties ($^1$H-NMR (CDCl$_3$)) |
|---|---|---|---|
| 13 | 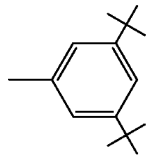 | 3 | 1.33(18H, s), 1.3–1.5(2H, m), 2.34(3H, s), 3.0–3.3(1H, m), 3.4–3.6(4H, m), 3.72 and 3.84(2H, ABq, J=16.0Hz), 5.60 (1H, s), 7.2–7.3(2H, m) |
| 14 | 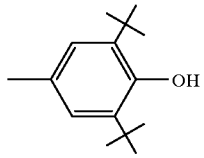 | 3 | 1.32(18H, s), 1.3–1.8(2H, m), 3.0–3.7 (5H, m), 3.74 and 3.87(2H, ABq, J=16.0Hz) 5.60(1H, s), 7.14(2H, s), 7.42(1H, s) |
| 15 |  | 3 | 1.42(18H, s), 1.2–1.6(2H, m), 3.0–3.2 (1H, m), 3.3–3.6(4H, m), 3.70 and 3.83 (2H, ABq, J–16.0Hz), 5.39(1H, s), 5.54 (1H, s), 7.11(2H, s) |

Reference Example 16

Preparation of 2-(3,5-Di-tert-butyl-4-hydroxyphenyl)-3-(3-hydroxypropyl)-1,3-thiazolidin-4-one In benzene (500 ml) were suspended 3,5-di-tert-butyl-4-hydroxybenzaldehyde (50.0 g) and β-alanine (20.0 g) under a nitrogen atmosphere. A Dean-Stark trap was fitted to the reactor, and the suspension was refluxed for 1 hour. After allowing the mixture to cool, α-mercaptoacetic acid (23.6 g) was added, then the mixture was further refluxed for 24 hours. After removal of benzene by evaporation, water (500 ml) was added to the residue, and the mixture was extracted with chloroform. The organic layer was dried over anhydrous sodium sulfate, and the solvent was removed under reduced pressure. The residue was purified by silica gel column chromatography (eluent; chloroform-methanol, 98:2) to afford 54.6 g (67%) of 2-(3,5-di-tert-butyl-4-hydroxyphenyl)-3-(2-carboxyethyl)-1,3-thiazolidin-4-one as colorless crystals. mp 164–165° C. NMR (CDCl$_3$, 200 MHz) δ: 1.42 (18H, s), 2.2–2.5 (1H, m), 2.5–2.8 (1H, m), 3.0–3.3 (1H, m), 3.5–4.0 (3H, m), 5.33 (1H, s), 5.64 (1H, s), 7.09 (2H, s), 8.5 (1H, brs)

To a solution of the resulting 2-(3,5-di-tert-butyl-4-hydroxyphenyl)-3-(2-carboxyethyl)-1,3-thiazolidin-4-one (100 mg) in tetrahydrofuran (3 ml) were added dropwise triethylamine (27 mg) and ethyl chloroformate (28 mg) at −10° C. under a nitrogen atmosphere, followed by stirring at −10 to −5° C. for 1 hour. To the mixture was added sodium borohydride (100 mg), the mixture was stirred at room temperature for 3 hours, then poured into ice-water and extracted with ethyl acetate. The organic layer was dried over anhydrous sodium sulfate, and the solvent was evaporated under reduced pressure. The residue was purified by silica gel column chromatography (eluent; chloroform-methanol, 98:2) to afford 70 mg (73%) of the product which was identical with that of Reference Example 15.

Reference Example 17

Preparation of 2-(3,5-Diisopropyl-4-hydroxyphenyl)-3-(3-chloropropyl)-1,3-thiazolidin-4-one To a dichloromethane (50 ml) solution of the 2-(3,5-diisopropyl-4-hydroxyphenyl)-3-(3-hydroxypropyl)-1,3-thiazolidin-4-one (1.97 g) obtained in Reference Example 1 was added thionyl chloride (1.04 g) under a nitrogen atmosphere, then the mixture was refluxed for 1 hour. The solvent was evaporated under reduced pressure, and to the residue were added brine and chloroform. The organic layer was separated and dried over anhydrous sodium sulfate, and the solvent was evaporated under reduced pressure. The residue was purified by silica gel column chromatography (eluent; dichloromethane) to afford 1.25 g (60%) of the title compound as pale yellow crystals. mp 105–106° C. NMR (CDCl$_3$, 60 MHz) δ: 1.23 (12H, d, J=6.6 Hz), 1.5–2.1 (2H, m), 2.6–3.8 (6H, m), 3.67 (2H, brs), 5.20 (1H, s), 5.50 (1H, brs), 6.88 (2H, s)

Reference Examples 18 to 28

Each compound shown in Tables 21 and 22 was prepared according to the procedure for Reference Example 17 using an appropriate alcohol in each case.

TABLE 21
| Ref. Ex. No. | R¹ | n | Physical Properties ($^1$H-NMR (CDCl$_3$)) |
|---|---|---|---|
| 18 | 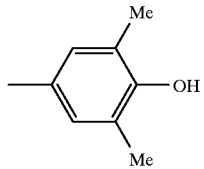 | 3 | 1.7–2.1(2H, m), 2.8–3.1(1H, m), 3.48 (2H, t, J=6.6Hz), 3.5–3.8(1H, m), 3.69 and 3.83(2H, ABq, J=16.0Hz), 5.59(2H, brs), 6.86(2H, d, J=8.0Hz), 7.22(2H, d, J=8.0Hz) |
| 19 | 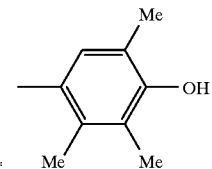 | 3 | 1.6–2.2(2H, m), 2.26(6H, s), 2.8–3.1 (1H, m), 3.47(2H, t, J=6.5Hz), 3.5–3.8 (1H, m), 3.67 and 3.82(2H, ABq, J=16.0Hz) 5.23(1H, brs), 5.53(1H, s), 6.91(1H, s) |
| 20 | 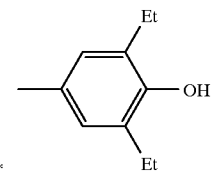 | 3 | 1.5–2.4(2H, m), 2.20(6H, s), 2.27(3H, s), 2.6–3.9(4H, m), 3.67(2H, brs), 5.20(1H, brs), 5.87(1H, brs), 6.77(1H, s) |
| 21 | 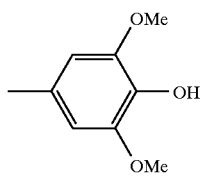 | 3 | 1.23(6H, t, J=7.5Hz), 1.7–2.2(2H, m), 2.4–3.2(5H, m), 3.3–3.6(3H, m), 3.70 (2H, brs), 5.20(1H, s), 5.50(1H, brs), 6.87(2H, s) |
| 22 | 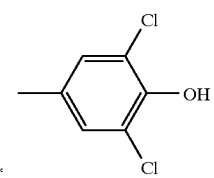 | 3 | 1.7–2.1(2H, m), 2.8–3.1(1H, m), 3.49 (2H, t, J=6.3Hz), 3.5–3.7(1H, m), 3.69 and 3.82(2H, ABq, J=16.0Hz), 3.90(6H, s), 5.58(1H, s), 5.82(1H, brs), 6.56 (2H, s) |
| 23 | 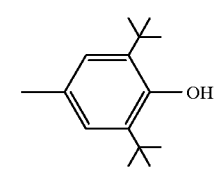 | 3 | 1.6–2.2(2H, m), 2.8–3.1(1H, m), 3.3– 3.6(3H, m), 3.68–3.82(2H, ABq, J=16.0 Hz), 5.51(1H, s), 6.37(1H, s), 7.24 (2H, s) |
| 24 |  | 4 | 1.40(18H, s), 1.2–2.0(4H, m), 2.6–3.0 (1H, m), 3.2–3.6(3H, m), 3.67(2H, brs), 5.27(1H, s), 5.50(1H, brs), 7.02(2H, s) |

TABLE 22

[Structure: thiazolidin-4-one with R¹ at 2-position and (CH₂)ₙ—Cl at N]

| Ref. Ex. No. | R¹ | n | Physical Properties ($^1$H-NMR (CDCl$_3$)) |
|---|---|---|---|
| 25 | 3,5-di-tert-butyl-4-hydroxyphenyl | 5 | 1.40(18H, s), 1.1–2.0(6H, m), 2.4–3.0 (1H, m), 3.2–3.8(3H, m), 3.67(2H, brs), 5.27(1H, s), 5.50(1H, brs), 7.00(2H, s) |
| 26 | 2,3,5-trimethyl-6-methoxyphenyl | 3 | 1.6–2.4(2H, m), 2.20(9H, s), 2.5–3.5 (2H, m), 3.48(2H, t, J=6.5Hz), 3.62(3H, s), 3.68(2H, brs), 5.83(1H, brs), 6.68(1H, s) |
| 27 | 3,5-di-tert-butyl-4-methoxyphenyl | 3 | 1.40(18H, s), 1.5–2.2(2H, m), 2.6–3.6 (2H, m), 3.40(2H, t, J=6.5Hz), 3.63(3H, s), 3.68(2H, brs), 5.52(1H, brs), 7.13 (2H, s) |
| 28 | 3,5-di-tert-butyl-4-hydroxyphenyl | 3 | 1.40(18H, s), 1.5–2.0(2H, m), 2.6–3.6 (2H, m), 3.40(2H, t, J=6.5Hz), 3.68(2H, brs), 5.27(1H, s), 5.50(1H, brs), 7.02 (2H, s) |

Reference Example 29

Preparation of 2-(3,5-Di-tert-butyl-4-hydroxyphenyl)-3-(3-bromopropyl)-1,3-thiazolidin-4-one To a solution of 2-(3,5-di-tert-butyl-4-hydroxyphenyl)-3-(3-hydroxypropyl)-1,3-thiazolidin-4-one (2.00 g) obtained in Reference Example 15 in diethyl ether (20 ml) was added phosphorus tribromide (0.74 g) under a nitrogen atmosphere, then the mixture was stirred at room temperature for 6 hours. After completion of the reaction, the mixture was poured into ice-water (100 ml), and the product was extracted with diethyl ether. The organic layer was washed with brine and dried over anhydrous sodium sulfate. The solvent was evaporated under reduced pressure, and the residue was purified by silica gel column chromatography (eluent; chloroform) to afford 1.31 g (56%) of the title compound as pale yellow crystals. mp 130–131° C. NMR (CDCl$_3$, 60 MHz) δ: 1.43 (18H, s), 1.6–2.2 (2H, m), 2.6–3.6 (2H, m), 3.28 (2H, t, J=6.5 Hz), 3.70 (2H, brs), 5.28 (1H, s), 5.53 (1H, brs), 7.05 (2H, s)

Each bromide shown in Table 23 was prepared according to the procedure for Reference Example 29, using an appropriate alcohol in each case.

TABLE 23

[Structure: thiazolidinone with R¹ at 2-position, N-(CH₂)ₙ-Br at 3-position]

| Ref. Ex. No. | R¹ | n | Physical Properties (¹H-NMR (CDCl₃)) |
|---|---|---|---|
| 30 | [2,6-dimethyl-4-methyl phenol with OH] Me | 3 | 1.38(9H, s), 1.5–2.2(2H, m), 2.23(3H, s), 2.5–3.7(4H, m), 3.70(2H, brs), 5.17(1H, s), 5.50(1H, brs), 6.8–7.2 (2H, m) |
| 31 | [3,5-di-tert-butyl-4-acetoxy phenyl] OAc | 3 | 1.34(18H, s), 1.7–2.1(2H, m), 2.35(3H, s), 2.9–3.1(1H, m), 3.30(2H, t, J=6.8 Hz), 3.4–3.7(1H, m), 3.68 and 3.76 (2H, ABq, J=16Hz), 5.61(1H, s), 7.27(2H, s) |
| 32 | [2,4-di-tert-butyl phenyl] | 3 | 1.31(18H, s), 1.7–2.2(2H, m), 2.8–3.1 (1H, m), 3.29(2H, t, J=6.3Hz), 3.4–3.7 (1H, m), 3.69 and 3.83(2H, ABq, J=16Hz), 5.61(1H, s), 7.13(2H, s), 7.40(1H, s) |

Example 1

Preparation of 2-(3,5-Diisopropyl-4-hydroxyphenyl)-3-[3-[N-methyl-N-[2-(3,4-methylenedioxyphenoxy)ethyl]amino]propyl]-1,3-thiazolidin-4-one To a solution of 2-(3,5-diisopropyl-4-hydroxyphenyl)-3-(3-chloropropyl)-1,3-thiazolidin-4-one (0.50 g) obtained in Reference Example 17 and N-methyl-N-[2-(3,4-methylenedioxy-phenoxy)ethyl]amine (0.30 g) in dimethylformamide (10 ml) were added sodium carbonate (0.29 g) and potassium iodide (0.30 g) under a nitrogen atmosphere, and the mixture was stirred at 80° C. for 24 hours. The solvent was removed by evaporation under reduced pressure, water (20 ml) was added to the residue, and the mixture was extracted with chloroform. The organic layer was washed successively with water and brine, then dried over anhydrous sodium sulfate. The solvent was evaporated under reduced pressure, and the residue was purified by silica gel column chromatography (eluent; chloroform-methanol, 97:3) to afford 0.26 g (36%) of the title compound as a pale brown oil. NMR (CDCl₃, 60 MHz) δ: 1.23 (12H, d, J=6.6 Hz), 1.4–1.9 (2H, m), 2.17 (3H, s), 2.3–3.8 (8H, m), 3.67 (2H, brs), 3.87 (2H, t, J=5.7 Hz), 5.00 (1H, brs), 5.57 (1H, s), 5.80 (2H, s), 6.0–6.7 (3H, m), 6.90 (2H, s)

Examples 2 to 25

Each compound shown in Tables 24 to 27 was prepared according to the procedure for Example 1, using a corresponding chloride and an appropriate amine in each case.

TABLE 24
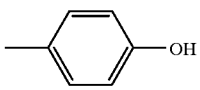
| Ex. No. | R¹ | n | R² | Physical Properties ($^1$H-NMR (CDCl$_3$)) |
|---|---|---|---|---|
| 2 | 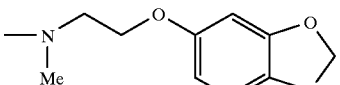 | 3 | 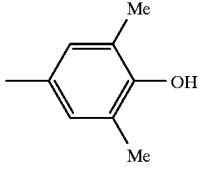 | 1.5–1.8(2H, m), 2.27(3H, s), 2.3–2.5(2H, m), 2.73(2H, t, J=5.7Hz), 2.6–3.1(1H, m), 3.5–3.7(1H, m), 3.66 and 3.80(2H, ABq, J=16Hz), 3.94 (2H, t, J=5.7Hz), 5.59(1H, s), 5.88 (2H, s), 6.2–7.2(8H, m) |
| 3 | 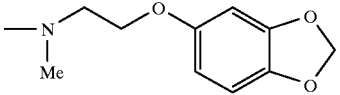 | 3 | 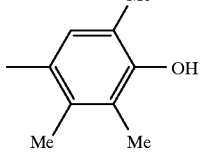 | 1.5–1.8(2H, m), 2.23(6H, s), 2.26 (3H, s), 2.3–2.5(2H, m), 2.68(2H, t, J=5.7Hz), 2.7–2.9(1H, m), 3.5–3.7(1H, m), 3.65 and 3.81(1H, ABq, J =16Hz), 3.91(2H, t, J=5.7Hz), 4.90 (1H, brs), 5.56(1H, s), 5.90(2H, s), 6.2–6.7(3H, m), 6.88(2H, s) |
| 4 | 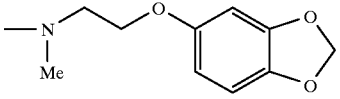 | 3 | 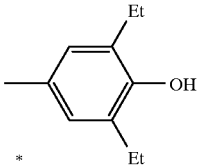 | 1.5–1.9(2H, m), 2.17(3H, s), 2.19 (3H, s), 2.21(3H, s), 2.29(3H, s), 2.3–2.5(2H, m), 2.70(2H, t, J=5.7 Hz), 2.6–2.9(1H, m), 3.4–3.8(1H, m), 3.61 and 3.76(2H, ABq, J=16Hz), 3.91(2H, t, J=5.7Hz), 5.87(3H, br s), 5.95(1H, s), 6.1–6.9(4H, m) |
| 5 | 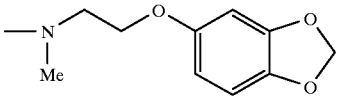 | 3 | 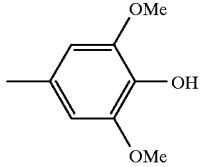 | 1.18(6H, t, J=7.2Hz), 1.4–1.8(2H, m), 2.17(3H, s), 2.3–3.1(9H, m), 3.3–3.8(1H, m), 3.65(2H, brs), 3.83 (2H, t, J=5.7Hz), 5.00(1H, brs), 5.52(1H, s), 5.78(2H, s), 6.0–6.7 (3H, m), 6.80(2H, s) |
| 6 | 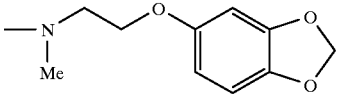 | 3 | 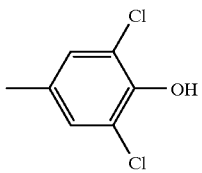 | 1.5–1.8(2H, m), 2.25(3H, s), 2.3–2.5(2H, m), 2.70(2H, t, J=5.7Hz), 2.7–2.9(1H, m), 3.6–3.8(1H, m), 3.67 and 3.79(2H, ABq, J=16Hz), 3.85 (6H, s), 3.93(2H, t, J=5.7Hz), 5.63 (1H, s), 5.89(2H, s), 6.2–6.7(6H, m) |
| 7 | 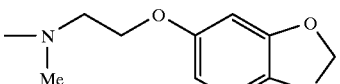 | 3 | | 1.5–2.0(2H, m), 2.37(3H, s), 2.3–2.9(3H, m), 2.86(2H, t, J=5.7Hz), 3.5–3.8(1H, m), 3.64 and 3.79(2H, ABq, J=16Hz), 4.02(2H, t, J=5.7Hz) 5.51(1H, s), 5.88(2H, s), 6.1–6.9 (4H, m), 7.14(2H, s) |

TABLE 25

General structure: 2-R¹-3-((CH₂)ₙ-R²)-thiazolidin-4-one

| Ex. No. | R¹ | n | R² | Physical Properties ($^1$H-NMR (CDCl$_3$)) |
|---|---|---|---|---|
| 8 | 3,5-di-tert-butyl-4-hydroxyphenyl (*) | 4 | -N(Me)-CH₂CH₂-O-(benzo[1,3]dioxol-5-yl) | 1.40(18H, s), 1.1–1.9(4H, m), 2.22 (3H, s), 2.2–2.8(3H, m), 2.65 (2H, t, J=5.7Hz), 3.2–3.8(1H, m) 3.65(2H, brs), 3.88(2H, t, J=5.7 Hz), 5.30(1H, brs), 5.52(1H, br s), 5.82(2H, s), 6.1–6.9(2H, m), 7.00(2H, s) |
| 9 | 3,5-di-tert-butyl-4-hydroxyphenyl (*) | 5 | -N(Me)-CH₂CH₂-O-(benzo[1,3]dioxol-5-yl) | 1.40(18H, s), 1.0–1.8(6H, m), 2.23 (3H, s), 2.1–3.0(3H, m), 2.67 (2H, t, J=5.7Hz), 3.2–3.8(1H, m) 3.67(2H, brs), 3.90(2H, t, J=5.7 Hz), 5.33(1H, brs), 5.50(1H, br s), 5.80(2H, s), 6.1–6.7(3H, m), 7.02(2H, s) |
| 10 | 2,3,5-trimethyl-4-methoxyphenyl | 3 | -N(Me)-CH₂CH₂-O-(benzo[1,3]dioxol-5-yl) | 1.5–1.9(2H, m), 2.18(3H, s), 2.20 (3H, s), 2.26(3H, s), 2.29(3H, s), 2.3–2.5(2H, m), 2.70(2H, t, J =5.7Hz), 2.6–3.0(1H, m), 3.5–4.0 (3H, m), 3.68(3H, s), 3.92(2H, t, J=5.7Hz), 5.89(2H, s), 5.94(1H, s), 6.1–6.9(4H, m) |
| 11 | 3,5-di-tert-butyl-4-methoxyphenyl | 3 | -N(Me)-CH₂CH₂-O-(benzo[1,3]dioxol-5-yl) | 1.41(18H, s), 1.2–1.8(2H, m), 2.20 (3H, s), 2.3–2.5(2H, m), 2.69 (2H, t, J=5.7Hz), 2.6–2.9(1H, m) 3.4–3.7(1H, m), 3.65(3H, s), 3.64 and 3.77(2H, ABq, J=16Hz), 3.80 (2H, t, J=5.7Hz), 5.57(1H, s), 5.89 (2H, s), 6.2–6.8(3H, m), 7.06 (2H, s) |
| 12 | 3,5-di-tert-butyl-4-hydroxyphenyl | 3 | -N(Et)-CH₂CH₂-O-(benzo[1,3]dioxol-5-yl) | 0.97(3H, t, J=6.8Hz), 1.43(18H, s), 1.2–1.8(2H, m), 2.4–2.6(4H, m), 2.7–3.0(1H, m), 2.74(2H, t, J=5.7Hz), 3.4–3.7(1H, m), 3.66 and 3.79(2H, ABq, J=16 Hz), 3.89(2H, t, J=5.7Hz), 5.33 (1H, s), 5.61(1H, s), 5.89(2H, s) 6.2–6.8(3H, m), 7.08(2H, s) |
| 13 | 3,5-di-tert-butyl-4-hydroxyphenyl | 3 | -N(Pr)-CH₂CH₂-O-(benzo[1,3]dioxol-5-yl) | 0.93(6H, d, J=6.3Hz), 1.43(18H, s), 1.2–1.7(2H, m), 2.41(2H, t, J =5.7Hz), 2.6–3.0(4H, m), 3.4–3.7 (1H, m), 3.62 and 3.75(2H, ABq, J =16Hz), 3.80(2H, t, J=5.7Hz), 5.33 (1H, s), 5.57(1H, s), 5.89(2H, s), 6.2–6.8(3H, m), 7.06(2H, s) |

TABLE 26

(structure: 2-R¹-3-((CH₂)ₙ-R²)-thiazolidin-4-one)

| Ex. No. | R¹ | n | R² | Physical Properties (¹H-NMR (CDCl₃)) |
|---|---|---|---|---|
| 14 | 2,6-di-tert-butyl-4-methylphenol (with OH) | 3 | -N(Me)-CH₂CH₂-O-C₆H₄-OMe (para) | 1.43(18H, s), 1.1–1.8(2H, m), 2.21 (3H, s), 2.3–2.5(2H, m), 2.70 (2H, t, J=5.7Hz), 2.6–3.0(1H, m) 3.4–3.9(3H, m), 3.76(3H, s), 3.96 (2H, t, J=5.7Hz), 5.30(1H, s), 5.64(1H, s), 6.79(4H, s), 7.09 (2H, s) |
| 15 | 2,6-di-tert-butyl-4-methylphenol (with OH) * | 3 | -N(Me)-CH₂CH₂-O-C₆H₃(OMe)₂ (3,4-diOMe) | 1.38(18H, s), 1.2–1.9(2H, m), 2.18(3H, s), 2.3–2.5(2H, m), 2.6–3.2(3H, m), 3.2–4.2(3H, m), 3.67 (2H, brs), 3.76(6H, s), 5.22 (1H, s), 5.57(1H, brs), 6.2–6.9 (3H, m), 7.00(2H, s) |
| 16 | 2,6-di-tert-butyl-4-methylphenol (with OH) | 3 | -N(Me)-CH₂CH₂-O-C₆H₂(OMe)₃ (3,4,5-triOMe) | 1.43(18H, s), 1.3–1.9(2H, m), 2.23 (3H, s), 2.3–2.5(2H, m), 2.71 (2H, t, J=5.7Hz), 2.6–3.0(1H, m) 3.4–3.9(3H, m), 3.77(3H, s), 3.83 (6H, s), 3.97(2H, t, J=5.7Hz), 5.30(1H, s), 5.63(1H, s), 6.12 (2H, s), 7.08(2H, s) |
| 17 | 2,6-di-tert-butyl-4-methylphenol (with OH) | 3 | -N(Me)-CH₂CH₂CH₂-O-(3,4-methylenedioxyphenyl) | 1.43(18H, s), 1.2–2.0(4H, m), 2.11 (3H, s), 2.2–2.4(2H, m), 2.40 (2H, t, J=7.1Hz), 2.7–2.9(1H, m) 3.4–3.6(1H, m), 3.66 and 3.80(2H, ABq, J=16Hz), 3.87(2H, t, J=5.7 Hz), 5.31(1H, s), 5.57(1H, s), 5.88 (2H, s), 6.2–6.8(3H, m), 7.07 (2H, s) |
| 18 | 2,6-di-tert-butyl-4-methylphenol (with OH) | 3 | -N(Me)-(CH₂)₄-O-(3,4-methylenedioxyphenyl) | 1.43(18H, s), 1.3–1.9 (6H, m), 2.07(3H, m), 2.1–2.5(4H, m), 2.6–3.0(1H, m), 3.4–3.7(1H, m), 3.67 and 3.80(2H, ABq, J= 16Hz), 3.86(2H, t, J=5.7Hz), 5.30 (1H, s), 5.58(1H, s), 5.88(2H, s), 6.1–6.8(3H, m), 7.07(2H, s) |
| 19 | 2,6-di-tert-butyl-4-methylphenol (with OH) | 3 | -N(Me)-CH₂-C₆H₃(OMe)₂ (3,4-diOMe) | 1.43(18H, s), 1.2–1.9(2H, m), 2.06 (3H, s), 2.1–2.4(2H, m), 2.6–3.0(1H, m), 3.34(2H, s), 3.4–3.7 (1H, m), 3.64 and 3.78(2H, ABq, J= 16Hz), 3.84(3H, s), 3.86(3H, s), 5.31(1H, s), 5.56(1H, s), 6.6–6.9 (3H, m), 7.06(2H, s) |

TABLE 27

| Ex. No. | R¹ | n | R² | Physical Properties ($^1$H-NMR (CDCl$_3$)) |
|---|---|---|---|---|
| 20 | 3,5-di-tert-butyl-4-hydroxyphenyl | 3 | -N(Me)CH$_2$CH$_2$-(3,4-dimethoxyphenyl) | 1.41(18H, s), 1.3–1.8(2H, m), 2.53(3H, s), 2.2–2.9(7H, m), 3.4–3.7(1H, m), 3.66 and 3.81(2H, Abq, J=16Hz), 3.83(3H, s), 3.84 (3H, s), 5.31(1H, s), 5.60(1H, s) 6.6–6.9(3H, m), 7.10(2H, s) |
| 21 | 3,5-di-tert-butyl-4-hydroxyphenyl | 3 | piperazinyl-CH$_2$-(2,3,4-trimethoxyphenyl) | 1.43(18H, s), 1.4–3.0(13H, m), 3.2–4.2(15H, m), 3.83(3H, s), 3.85(3H, s), 3.86(3H, s), 5.30 (1H, s), 5.61(1H, s), 6.60(1H, d, J=8.6Hz), 6.94(1H, s), 5.62(1H, s), 7.0–7.3(7H, m) |
| 22 | 3,5-di-tert-butyl-4-hydroxyphenyl | 3 | piperidinyl-CH$_2$Ph | 1.36(18H, s), 1.1–1.9(9H, m), 2.1–2.3(2H, m), 2.5(2H, d, J=6.6Hz), 2.7–2.9(3H, m), 3.4–3.6 (1H, m), 3.66 and 1.79(2H, Abq, J=16Hz), 5.32(1H, s), 5.62(1H, s), 7.0–7.3(7H, m) |
| 23 | 3,5-di-tert-butyl-4-hydroxyphenyl | 3 | piperazinyl-CHPh$_2$ | 1.40(18H, s), 1.2–1.8(2H, m) 2.1–2.5(10H, m), 2.7–2.9(1H, m) 3.4–3.6(1H, m), 3.65 and 3.77 (2H, ABq, J=16Hz), 4.16(1H, s), 5.27(1H, s), 5.58(1H, s), 7.04 (2H, s), 7.1–7.4(10H, m) |
| 24 | 3,5-di-tert-butyl-4-hydroxyphenyl* | 3 | 6,7-dimethoxy-1,2,3,4-tetrahydroisoquinolin-2-yl | 1.37(18H, s), 1.5–2.0(2H, m), 2.1–3.1(8H, m), 3.42(2H, s), 3.65(2H, brs), 3.75(6H, s), 5.39(1H, s), 5.57(1H, brs), 6.42 (1H, s), 6.50(1H, s), 7.02(2H, s) |
| 25 | 3,5-di-tert-butyl-4-hydroxyphenyl* | 3 | 1-methylpiperidin-4-yl-N(Me)-benzothiazol-2-yl | 1.43(18H, s), 1.0–3.2(15H, m), 3.00(3H, s), 3.67(2H, brs), 5.27(1H, s), 5.56(1H, brs), 6.7–8.0(6H, m) |

Examples 26-A

Preparation of 2-(3,5-Di-tert-butyl-4-hydroxyphenyl)-3-[3-[N-methyl-N-[2-(3,4-methylenedioxyphenoxy)ethyl]amino]propyl]-1,3-thiazolidin-4-one To a solution of the 2-(3,5-di-tert-butyl-4-hydroxyphenyl)-3-(3-bromopropyl)-1,3-thiazolidin-4-one (89.3 mg) obtained in Reference Example 29 and N-methyl-N-[2-(3,4-methylenedioxyphenoxy)ethyl]amine (48.8 mg) in acetone (5 ml) was added potassium carbonate (34.6 mg) under a nitrogen atmosphere, and the mixture was refluxed for 10 hours. After allowing the mixture to cool, inorganic matter was removed by filtration, and the filtrate was concentrated under reduced pressure. The residue was purified by silica gel column chromatography (eluent; chloroform-methanol, 97:3) to afford 67.4 mg (60%) of the title compound as colorless crystals. mp 70–71° C. NMR (CDCl$_3$, 200 MHz) δ: 1.42 (18H, s), 1.4–1.7 (2H, m), 2.20 (3H, s), 2.3–2.5 (2H, m), 2.68 (2H, t, J=5.9 Hz), 2.7–2.9 (1H, m), 3.5–3.6 (1H, m), 3.66 and 3.80 (2H, ABq, J=16.0 Hz), 3.92 (2H, t, J=5.9 Hz), 5.32 (1H, s), 5.66 (1H, s), 5.90 (2H, s), 6.2–6.7 (3H, m), 7.09 (2H, s)

Examples 27 to 34

Each compound shown in Tables 28 and 29 was prepared according to the procedure for Example 26-A, using a corresponding bromide and an appropriate amine in each case.

TABLE 28

| Ex. No. | R¹ | n | R² | Physical Properties ($^1$H-NMR (CDCl$_3$)) |
|---|---|---|---|---|
| 27 | 2,6-di-t-butyl-4-methylphenol derivative (with Me) | 3 | N(Me)CH$_2$CH$_2$O-benzodioxole | 1.39(9H, s), 1.2–1.8(2H, m), 2.21 (3H, s), 2.24(3H, s), 2.2–2.5(2H, m), 2.67(2H, t, J=5.7Hz), 2.6–2.9(1H, m), 3.5–3.8(1H, m), 3.67 and 3.80(2H, ABq, J=16Hz), 3.91 (2H, t, J=5.7Hz), 5.19(1H, brs), 5.58(1H, s), 5.88(2H, s), 6.1–7.1(5H, m) |
| 28 | 2,6-di-t-butyl-4-methylphenol | 3 | N(Me)CH$_2$-benzodioxole | 1.41(18H, s), 1.5–1.8(2H, m), 2.00(3H, s), 2.1–2.4 (2H, m), 2.6–3.0(1H, m), 3.27(2H, s), 3.4–3.7(1H, m), 3.63 and 3.77(2H, ABq, J=16Hz), 5.31(1H, s), 5.56(1H, s), 5.90(2H, s), 6.5–6.8(3H, m), 7.09(2H, s) |
| 29 | 3,5-di-t-butyl-4-methylphenyl | 3 | N(Me)CH$_2$CH$_2$O-benzodioxole | 1.31(18H, s), 1.4–1.8(2H, m), 2.20 (3H, s), 2.2–2.4(2H, m), 2.67 (2H, t, J=5.7Hz), 2.7–2.9(1H, m) 3.4–3.7(1H, m), 3.67 and 3.80(2H, ABq, J=16Hz), 3.91(2H, t, J=5.7 Hz), 5.63(1H, s), 5.89(2H, s), 6.1–6.8(3H, m), 7.10(2H, s), 7.37(1H, s) |
| 30 | 2,6-di-t-butyl-4-methylphenyl OAc | 3 | N(Me)CH$_2$CH$_2$O-benzodioxole | 1.27(18H, s), 1.4–1.8(2H, m), 2.16 (3H, s), 2.29(3H, s), 2.2–2.4 (2H, m), 2.64(2H, t, J=5.9Hz), 2.7–2.9(1H, m), 3.5–3.6(1H, m), 3.62 and 3.73(2H, ABq, J=16Hz), 3.89 (2H, t, J=5.9Hz), 5.61(1H, s), 5.80(2H, s), 6.2–7.2(5H, m) |
| 31 | 2,6-di-t-butyl-4-methylphenol | 3 | NH-CH$_2$CH$_2$O-benzodioxole | 1.42(18H, s), 1.5–1.7(3H, m), 2.61 (2H, t, J=6.9Hz), 2.8–2.9(1H, m), 2.89(2H, t, J=5.3Hz), 3.6–3.7(1H, m), 3.68 and 3.78(2H, ABq, J =16Hz), 3.95(2H, t, J=5.3Hz), 5.34 (1H, brs), 5.60(1H, s), 5.90(2H, s), 6.2–6.8(3H, m) 7.08(2H, s) |
| 32 | 2,6-di-t-butyl-4-methylphenol | 3 | N(Me)CH$_2$CH$_2$O-C$_6$H$_4$-F | 1.41(18H, s), 1.4–2.0(2H, m), 2.21 (3H, s), 2.2–2.6(2H, m), 2.72 (2H, t, J=5.7Hz), 2.7–3.0(1H, m) 3.4–3.7(1H, m), 3.68 and 3.81(2H, ABq, J=16Hz), 3.96(2H, t, J=5.7 Hz), 5.30(1H, s), 5.61(1H, s), 6.6–7.3(6H, m) |

TABLE 29

R¹—[thiazolidin-4-one ring]—(CH₂)ₙ—R²

| Ex. No. | R¹ | n | R² | Physical Properties (¹H-NMR (CDCl₃)) |
|---|---|---|---|---|
| 33 | 3,5-di-tert-butyl-4-hydroxyphenyl (with methyl) | 3 | 4-(4-chlorophenyl)-4-hydroxypiperidin-1-yl | 1.42(18H, s), 1.5–1.8(5H, m), 1.9–2.1(2H, m), 2.2–2.4(4H, m), 2.5–2.9(3H, m), 3.4–3.7(1H, m), 3.63 and 3.77(2H, ABq, J=16Hz), 5.32(1H, s), 5.60(1H, s), 7.05 (2H, s), 7.2–7.4(4H |
| 34 | 3,5-di-tert-butyl-4-hydroxyphenyl (with methyl) | 3 | 4-(benzo[d][1,3]dioxol-5-yloxy)piperidin-1-yl | 1.43(18H, s), 1.5–1.8(4H, m), 1.8–2.0(2H, m), 2.0–2.4(4H, m), 2.5–2.7(2H, m), 2.7–2.9(1H, m), 3.5–3.7(1H, m), 3.67 and 3.78(2H, ABq, J=16Hz), 4.0–4.2(1H, m), 5.31 (1H, s), 5.62(1H, s), 5.91(2H, s), 6.2–6.8(3H, m), 7.08(2H, s) |

Reference Example 33

Preparation of 2-(3,5-Di-tert-butyl-4-hydroxyphenyl)-3-[3-(N-methylamino)propyl]-1,3-thiazolidin-4-one Hydrobromide A mixture of 2-(3,5-di-tert-butyl-4-hydroxyphenyl)-3-(3-bromopropyl)-1,3-thiazolidin-4-one (1.10 g) obtained in Reference Example 29, 40% methanolic solution of methylamine (20 ml), and acetonitrile (15 ml) was stirred at room temperature for 15 hours under a nitrogen atmosphere. After completion of the reaction, the solvent and excess methylamine were removed under reduced pressure. The residue was purified by silica gel column chromatography (eluent; chloroform-methanol, 95:5) to afford 0.90 g (76%) of the title compound as pale orange crystals. mp 195–196° C. NMR (CDCl₃, 60 MHz) δ: 1.42 (18H, s), 1.6–2.2 (2H, m), 2.67 (3H, s), 2.6–3.6 (4H, m), 3.77 (2H, brs), 5.33 (1H, s), 5.63 (1H, brs), 7.08 (2H, s)

Each compound shown in Table 30 was prepared according to the procedure for Reference Example 33, using an appropriate amine instead of methylamine in each case.

In Reference Example 35, chromatographic purification was performed on a column of silica gel using chloroform-methanol, 95:5 containing 1% triethylamine as an eluent.

TABLE 30

R¹—[thiazolidin-4-one ring]—(CH₂)ₙ—R²

| Ref. Ex. No. | R¹ | n | R² | Physical Properties (¹H-NMR (CDCl₃)) |
|---|---|---|---|---|
| 34 | 3,5-di-tert-butyl-4-hydroxyphenyl | 3 | cyclopropyl-NH·HBr | 0.4–1.0(4H, m), 1.43(18H, s), 1.5–2.5(3H, m), 2.6–3.7(4H, m), 3.75(2H, brs), 5.33(1H, brs), 5.52(1H, brs), 7.07 (2H, s) |

TABLE 30-continued

[Structure: thiazolidin-4-one with R¹ at position 2, (CH₂)ₙ—R² at N]

| Ref. Ex. No. | R¹ | n | R² | Physical Properties ($^1$H-NMR (CDCl$_3$)) |
|---|---|---|---|---|
| 35 | 3,5-di-tert-butyl-4-hydroxyphenyl | 3 | —NH—CH₂CH₂—OH | 1.43(18H, s), 1.4–1.8(3H, m), 2.4–3.2(7H, m), 3.4–4.0(4H, m), 5.30(1H, s), 5.5(1H, s), 7.06(2H, s) |

Example 26-B

To a solution of the 2-(3,5-di-tert-butyl-4-hydroxyphenyl)-3-[3-(N-methylamino)propyl]-1,3-thiazolidin-4-one hydrobromide (380 mg) obtained in Reference Example 33 and 2-(3,4-methylenedioxyphenoxy) ethyl bromide (260 mg) in acetone (10 ml) was added potassium carbonate (300 mg) and the mixture was refluxed for 10 hours under a nitrogen atmosphere. After allowing the reaction mixture to cool, insoluble matter was removed by filtration, and the filtrate was concentrated under reduced pressure. The residue was purified by silica gel column chromatography (eluent; chloroform-methanol, 97:3) to afford 350 mg (64%) of the same compound as obtained in Example 26-A.

Examples 35 to 37

Each compound of Table 31 was prepared according to the procedure for Example 26-B, reacting each of the compounds shown in Table 30 with an appropriate bromide in each case.

TABLE 31

[Structure: thiazolidin-4-one with R¹ at position 2, (CH₂)ₙ—R² at N]

| Ex. No. | R¹ | n | R² | Physical Properties ($^1$H-NMR (CDCl$_3$)) |
|---|---|---|---|---|
| 35 | 3,5-di-tert-butyl-4-hydroxyphenyl * | 3 | —N(Me)—CH₂—C₆H₅ | 1.43(18H, s), 1.2–2.0(2H, m), 2.05(3H, s), 2.0–3.3(4H, m), 3.40(2H, s), 3.70(2H, brs), 5.30(1H, s), 5.57(1H, brs), 7.07(2H, s), 7.20(5H, s) |
| 36 | 3,5-di-tert-butyl-4-hydroxyphenyl * | 3 | —N(cyclopropyl)—CH₂—C₆H₅ | 0.2–0.6(4H, m), 1.40(18H, s), 1.2–2.1(2H, m), 2.2–3.5(5H, m), 3.57(2H, s), 3.63(2H, brs) 5.23(1H, s), 5.42(1H, brs), 6.97(2H, s), 7.12(5H, s) |
| 37 | 3,5-di-tert-butyl-4-hydroxyphenyl | 3 | —N(CH₂CH₂OH)—CH₂CH₂—O—(3,4-methylenedioxyphenyl) | 1.41(18H, s), 1.4–2.0(2H, m), 2.4–3.0(7H, m), 3.4–3.7(4H, m), 3.64 and 3.77(2H, ABq, J=16 Hz), 3.89(2H, t, J=5.7Hz), 5.30(1H, s), 5.54(1H, s), 5.89 (2H, s), 6.1–6.8(3H, m), 7.06 (2H, s) |

Example 38

Preparation of 2-(3,5-Di-tert-butyl-4-hydroxyphenyl)-3-[3-[N-methyl-N-[2-hydroxy-3-(3,4-methylenedioxyphenoxy)propyl]amino]propyl]-1,3-thiazolidin-4-one To a solution of the 2-(3,5-di-tert-butyl-4-hydroxyphenyl)-3-[3-(N-methylamino)propyl]-1,3-thiazolidin-4-one (0.50 g) obtained in Reference Example 33 in acetonitrile (10 ml) was added 2,3-epoxypropyl-3,4-methylenedioxyphenyl ether (0.26 g) at room temperature, and the mixture was refluxed for 8 hours. After allowing to cool, the mixture was poured into ice-water and extracted with ethyl acetate. The organic layer was washed with brine and dried over anhydrous sodium sulfate. The solvent was evaporated under reduced pressure, and the residue was purified by silica gel column chromatography (eluent; chloroform-methanol, 98:2) to afford 0.72 g (95%) of the title compound as a colorless oil. NMR (CDCl$_3$, 270 MHz) δ: 1.43 (18H, s), 1.4–1.8 (2H, m), 2.17 (3H, s), 2.2–2.6 (4H, m), 2.7–3.0 (1H, m), 3.4–3.7 (1H, m), 3.67 and 3.80 (2H, ABq, J=16.0 Hz), 3.8–4.1 (4H, m), 5.33 (1H, s), 5.57 (1H, s), 5.91 (2H, s), 6.2–6.8 (3H, m), 7.09 (2H, s)

Examples 39 and 40

Each compound shown in Table 32 was prepared according to the procedure for Example 38, using an appropriate epoxide in each case.

of N-[3-[N'-methyl-N'-[2-(3,4-methylenedioxy-phenoxy)ethyl]amino]propyl]phthalimide as a brown oil. NMR (CDCl$_3$, 60 MHz) δ: 1.5–2.2 (2H, m), 2.28 (3H, s), 2.3–2.9 (4H, m), 3.72 (2H, t, J=7.0 Hz), 3.90 (2H, t, J=6.0 Hz), 5.82 (2H, s), 6.0–6.8 (3H, m), 7.4–8.0 (4H, m)

The resulting N-[3-[N'-methyl-N'-[2-(3,4-methylenedioxyphenoxy)ethyl]amino]propyl]phthalimide (1.82 g) was dissolved in 40% methanolic solution of methylamine (10 ml), and the mixture was stirred at room temperature overnight. After completion of the reaction, the solvent and excess methylamine were removed under reduced pressure. The residue was purified by silica gel column chromatography (eluent; chloroform-methanol, 1:1 containing 1% triethylamine) to afford 0.74 g (62%) of the title compound as a pale brown oil. NMR (CDCl$_3$) (60 MHz) δ: 1.33 (2H, s), 1.1–2.1 (2H, m), 2.27 (3H, s), 2.2–3.0 (6H, m), 3.90 (2H, t, J=6.0 Hz), 5.77 (2H, s), 6.0–6.8 (3H, m)

Reference Example 37

Preparation of 2-[N-Methyl-N-[2-(3,4-methylenedioxyphenoxy)ethyl]amino]ethylamine The title compound was prepared according to the procedure for Reference Example 36, using N-(2-bromoethyl)phthalimide instead of N-(3-bromopropyl)phthalimide. NMR (CDCl$_3$) (60 MHz) δ: 2.34 (3H, s), 2.0–3.2 (8H, m), 3.90 (2H, t, J=6.0 Hz), 5.85 (2H, s), 6.0–6.9 (3H, m)

TABLE 32

| Ex. No. | R$^1$ | n | R$^2$ | Physical Properties ($^1$H-NMR (CDCl$_3$)) |
|---|---|---|---|---|
| 39 | 3,5-di-tert-butyl-4-hydroxyphenyl | 3 | —N(Me)CH$_2$CH(OH)CH$_2$O-phenyl | 1.43(18H, s), 1.4–1.8(2H, m), 2.19(3H, s), 2.2–3.0(6H, m), 3.3–3.7(1H, m), 3.66 and 3.79 (2H, ABq, J=16Hz), 3.8–4.2(3H, m), 5.31(1H, s), 5.54(1H, s) 6.7–7.0(3H, m), 7.06(2H, s), 7.1–7.5(2H, m) |
| 40 | 3,5-di-tert-butyl-4-hydroxyphenyl | 3 | —N(Me)CH$_2$CH(OH)CH$_2$O-(4-OMe-phenyl) | 1.43(18H, s), 1.4–1.9(2H, m), 2.16(3H,s), 2.2–3.0(6H, m), 3.3–4.2(6H, m), 3.74(3H, s), 5.31(1H, s), 5.54(1H, s), 6.81 (4H, s), 7.06(2H, s) |

Reference Example 36

Preparation of 3-[N-Methyl-N-[2-(3,4-methylenedioxyphenoxy)ethyl]amino]propylamine In acetone (20 ml) were suspended N-methyl-N-[2-(3,4-methylenedioxyphenoxy)ethyl]amine (1.0 g), N-(3-bromopropyl)phthalimide (1.51 g), and potassium carbonate (0.78 g), and the suspension was refluxed for 3 hours.

After allowing to cool, the mixture was filtered to remove inorganic matter, and the filtrate was concentrated. The residue was purified by silica gel column chromatography (eluent; chloroform-methanol, 10:1) to afford 1.82 g (93%)

Example 41 (Method-A)

Preparation of 2-(3,5-Di-tert-butyl-4-hydroxyphenyl)-3-[3-[N-methyl-N-[2-(3,4-methylenedioxyphenoxy)ethyl]amino]propyl]-5-methyl-1,3-thiazolidin-4-one The title compound was prepared according to the procedure for Reference Example 1, using 3-[N-methyl-N-[2-(3,4-methylenedioxyphenoxy)ethyl]amino]propylamine and 2-mercaptopropionic acid instead of 3-aminopropanol and α-mercaptoacetic acid. NMR (CDCl$_3$) (270 MHz) δ: 1.42 (18H, s), 1.2–1.8 (2H, m), 1.58 (3×2/5H, d, J=6.9 Hz), 1.65

(3×3/5H, d, J=6.9 Hz), 2.20 (3×3/5H, s), 2.23 (3×2/5H, s), 2.2–2.5 (2H, m), 2.6–2.9 (3H, m), 3.4–3.7 (1H, m), 3.8–4.1 (3H, m), 5.29 (2/5H, s), 5.30 (3/5H, s), 5.56 (3/5H, s), 5.57 (2/5H, brs), 5.90 (2H, s), 6.2–6.8 (3H, m), 7.05 (2×2/5H, s), 7.11 (2×3/5H, s)

Example 42

Preparation of 2-(3,5-Di-tert-butyl-4-hydroxyphenyl)-3-[2-[N-methyl-N-[2-(3,4-methylenedioxyphenoxy)ethyl]amino]ethyl]-1,3-thiazolidin-4-one The title compound was prepared according to the procedure for Reference Example 1, using 2-[N-methyl-N-[2-(3,4-methylenedioxyphenoxy)ethyl]amino]ethylamine instead of 3-aminopropanol. NMR (CDCl$_3$) (60 MHz) δ: 1.40 (18H, s), 2.20 (3H, s), 2.5–3.0 (5H, m), 3.3–4.1 (3H, m), 3.65 (2H, brs), 5.23 (1H, s), 5.73 (1H, s), 5.82 (2H, s), 6.0–6.8 (3H, m), 7.00 (2H, s)

Example 43

Preparation of 2-(3-tert-Butyl-4-hydroxyphenyl)-3-[3-[N-methyl-N-[2-(3,4-methylenedioxyphenoxy)ethyl]amino]propyl]-1,3-thiazolidin-4-one In acetic acid (5 ml) was dissolved 2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one (0.35 g), and 47% hydrobromic acid (5 ml) was added, then the mixture was stirred at room temperature for 7 days. After completion of the reaction, the mixture was poured into an ice-cooled 5% aqueous solution of sodium carbonate and extracted with chloroform. The organic layer was dried over anhydrous sodium sulfate, and the solvent was evaporated under reduced pressure. The residue was purified by silica gel column chromatography (eluent; chloroform-methanol, 98:2) to afford 0.05 g (16%) of the title compound as a pale brown oil. NMR (CDCl$_3$) (200 MHz) δ: 1.37 (9H, s), 1.2–1.9 (2H, m), 2.26 (3H, s), 2.1–2.5 (2H, m), 2.71 (2H, t, J=5.7 Hz), 2.6–3.0 (1H, m), 3.4–3.8 (1H, m), 3.67 and 3.80 (2H, ABq, J=16.0 Hz), 3.94 (2H, t, J=5.7 Hz), 5.60 (1H, s), 5.82 (1H, s), 5.88 (2H, s), 6.1–7.0 (5H, m), 7.14 (1H, s)

Reference Example 38

2-(3,5-Di-tert-butyl-4-hydroxyphenyl)-3-(3-hydroxypropyl)-5-methyl-1,3-thiazolidin-4-one was prepared according to the procedure for Reference Example 1, using 2-mercaptopropionic acid instead of α-mercaptoacetic acid. NMR (CDCl$_3$) (200 MHz) δ: 1.43 (18H, s), 1.1–1.7 (2H, m), 1.60 (3×1/4H, d, J=6.9 Hz), 1.67 (3×3/4H, d, J=6.9 Hz), 3.0–3.3 (1H, m), 3.3–3.7 (4H, m), 3.9–4.2 (1H, m), 5.34 (1/4H, s), 5.36 (3/4H, s), 5.49 (3/4H, s), 5.52 (1/4H, s), 7.07 (2×1/4H, s), 7.12 (2×3/4H, s)

Reference Examples 39 and 40

Each compound shown in Table 33 was prepared according to the procedure for Reference Example 38, using an appropriate α-mercaptocarboxylic acid instead of 2-mercaptopropionic acid in each case.

TABLE 33

| Ref. Ex. No. | R$^1$ | n | R$^5$ | Physical Properties ($^1$H-NMR (CDCl$_3$)) |
|---|---|---|---|---|
| 39 | 3,5-di-tert-butyl-4-hydroxyphenyl | 3 | phenyl | 1.40(18H, s), 1.2–1.8(2H, m), 2.56(1H, brs), 3.0–3.8(4H, m), 5.10(1H, s), 5.33(1H, s), 5.57(1H, s), 7.0–7.7(7H, m) |
| 40 | 3,5-di-tert-butyl-4-hydroxyphenyl | 3 | 4-methoxyphenyl | 1.43(18H, s), 1.1–1.8(2H, m), 3.0–3.7(5H, m), 3.81(3H, s), 5.08(1H, s), 5.37(1H, s), 5.58(1H, s), 6.91(2H, d, J=8.7Hz), 7.20(2H, s), 7.44(2H, d, J=8.7Hz) |

Reference Example 41

Preparation of 2-(3,5-Di-tert-butyl-4-hydroxyphenyl)-3-(3-hydroxypropyl)-5-carboxymethyl-1,3-thiazolidin-4-one In benzene (200 ml) were suspended 3,5-di-tert-butyl-4-hydroxybenzaldehyde (23.4 g) and 3-aminopropanol (9.01 g) under a nitrogen atmosphere. After fitting a Dean-Stark trap to the reactor, the suspension was refluxed for 2 hours. After allowing the mixture to cool, thiomalic acid (19.52 g) was added thereto, then the mixture was refluxed for an additional period of 3 hours. Benzene was removed by evaporation, and the resulting white solid was recrystallized from aqueous methanol to afford 10.5 g (25%) of the title compound as colorless crystals. mp 227–228° C. NMR ($d_6$-DMSO) (200 MHz) d: 1.37 (18H, s), 1.2–1.8 (2H, m), 2.3–2.8 (1H, m), 3.0–3.6 (5H, m), 4.0–4.2 (1H, m), 4.37 (1H, brs), 5.73 (1H, s), 7.10 (2H, s), 7.13 (1H, s)

Reference Example 42

2-(3,5-Di-tert-butyl-4-hydroxyphenyl)-3-(3-chloropropyl)-5-methyl-1,3-thiazolidin-4-one was prepared from 2-(3,5-di-tert-butyl-4-hydroxyphenyl)-3-(3-hydroxypropyl)-5-methyl-1,3-thiazolidin-4-one according to the procedure for Reference Example 17. NMR ($CDCl_3$) (60 MHz) δ: 1.42 (18H, s), 1.1–2.2 (5H, m), 2.7–4.2 (5H, m), 5.23 (1H, s), 5.43 (1H, brs), 6.97 (2H, brs)

Reference Examples 43 and 44

Each compound shown in Table 34 was prepared from each of the compounds prepared in Reference Examples 39 and 40, respectively, according to the procedure for Reference Example 29.

Reference Example 45

Preparation of 2-(3,5-Di-tert-butyl-4-hydroxyphenyl)-3-(3-bromopropyl)-5-ethoxycarbonylmethyl-1,3-thiazolidin-4-one To a suspension of 2-(3,5-di-tert-butyl-4-hydroxyphenyl)-3-(3-hydroxypropyl)-5-carboxymethyl-1,3-thiazolidin-4-one (2.45 g) in diethyl ether (30 ml) was added phosphorus tribromide (3.45 g), and the mixture was stirred at room temperature for 3 hours. To the mixture was added dropwise ethanol (30 ml) under cooling with ice, the mixture was stirred at room temperature overnight. After completion of the reaction, the reaction mixture was poured into 100 ml of ice-water, and the product was extracted with ethyl acetate. The organic layer was washed with brine and dried over anhydrous sodium sulfate. The solvent was removed by evaporation under reduced pressure, and the residue was purified by silica gel column chromatography (eluent; ethyl acetate:n-hexane, 20:80) and then recrystallized from chloroform/n-hexane to afford 1.50 g (51%) of the title compound as colorless crystals. mp 154–155° C. NMR ($CDCl_3$) (200 MHz) δ: 1.26 (3H, t, J7.1 Hz), 1.43 (18H, s), 1.6–2.2 (2H, m), 2.6–3.1 (2H, m), 3.2–3.6 (4H, m), 4.17 (2H, q, J=7.1 Hz), 4.1–4.4 (1H, m), 5.33 (1H, s), 5.53 (1H, s), 7.14 (2H, s)

Reference Example 46

2-(3,5-Di-tert-butyl-4-hydroxyphenyl)-3-(3-bromopropyl-5-isopropoxycarbonylmethyl-1,3-thiazolidin-4-one was prepared as colorless crystals according to the procedure for Reference Example 45, using isopropyl alcohol instead of ethanol. mp 170–171+ C. NMR ($CDCl_3$) (200 MHz) δ: 1.24 (6H, d, J=5.7 Hz), 1.43 (18H, s), 1.6–2.2 (2H, m), 2.6–3.7 (6H, m), 4.1–4.4 (1H, m), 4.8–5.2 (1H, m), 5.33 (1H, s), 5.53 (1H, s), 7.14 (2H, s)

TABLE 34

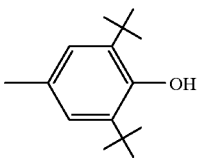

| Ex. No. | $R^1$ | n | $R^5$ | Physical Properties ($^1$H-NMR ($CDCl_3$)) |
|---|---|---|---|---|
| 43 | 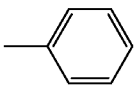 | 3 | 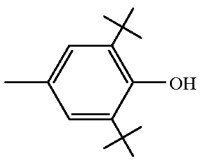 | 1.43(18H, s), 1.7–2.3(2H, m), 2.8–3.7(4H, m), 5.04(1H, s), 5.32(1H, s), 5.60(1H, s), 7.0–7.7(7H, m) |
| 44 | 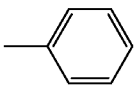 | 3 | 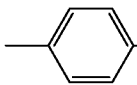 | 1.43(18H, s), 1.7–2.3(2H, m), 2.9–9.7(4H, m), 3.81(3H, s), 5.03(1H, s), 5.35(1H, s), 5.61(1H, s), 6.91(2H, d, J=8.7Hz), 7.21(2H, s), 7.43 (2H, d, J=8.7Hz) |

Example 41 (Method-B)

Preparation of 2-(3,5-Di-tert-butyl-4-hydroxyphenyl)-3-[3-[N-methyl-N-[2-(3,4-methylenedioxyphenoxy)ethyl]amino]propyl]-5-methyl-1,3-thiazolidin-4-one The title compound was prepared according to the procedure for Example 1, using 2-(3,5-di-tert-butyl-4-hydroxyphenyl)-3-(3-chloropropyl)-5-methyl-1,3-thiazolidin-4-one prepared in Reference Example 42. The data of instrumental analyses on the resulting compound were identical with those of the compound prepared in Example 41-A.

Examples 44 and 45

Each compound shown in Table 35 was prepared according to the procedure for Examples 26-A, using respective compounds obtained in Reference Examples 43 and 44, instead of 2-(3,5-di-tert-butyl-4-hydroxyphenyl)-3-(3-bromopropyl)-1,3-thiazolidin-4-one.

(2H, m), 3.91 (2H, t, J=5.7 Hz), 4.17 (2H, q, J=7.1 Hz), 4.1–4.4 (1H, m), 5.29 (1H, s), 5.58 (1H, s), 5.89 (2H, s), 6.1–6.8 (3H, m), 7.09 (2H, s)

Example 47

According to the procedure for Example 46, using 2-(3,5-di-tert-butyl-4-hydroxyphenyl)-3-(3-bromopropyl)-5-isopropoxycarbonylmethyl-1,3-thiazolidin-4-one instead of 2-(3,5-di-tert-butyl-4-hydroxyphenyl)-3-(3-bromopropyl)-5-ethoxycarbonylmethyl-1,3-thiazolidin-4-one, 2-(3,5-di-tert-butyl-4-hydroxyphenyl)-3-[3-[N-methyl-N-[2-(3,4-methylenedioxyphenoxy)ethyl]amino]propyl]-5-isopropoxycarbonylmethyl-1,3-thiazolidin-4-one was prepared as colorless crystals. mp 81–82° C. NMR (CDCl$_3$) (200 MHz) δ: 1.23 (6H, d, J=5.7 Hz), 1.41 (18H, s), 1.4–2.0 (2H, m), 2.20 (3H, s), 2.2–2.5 (2H, m), 2.5–3.0 (4H, m), 3.1–3.7 (2H, m), 3.93 (2H, t, J=5.7 Hz), 4.1–4.4 (1H, m), 4.8–5.2 (1H, m), 5.30 (1H, s), 5.57 (1H, s), 5.89 (2H, s), 6.1–6.8 (3H, m), 7.10 (2H, s)

TABLE 35

| Ex. No. | R$^1$ | n | R$^5$ | Physical Properties ($^1$H-NMR (CDCl$_3$)) |
|---|---|---|---|---|
| 44 | 3,5-di-tert-butyl-4-hydroxyphenyl | 3 | phenyl | 1.41(18H, s), 1.4–1.9(2H, m), 2.20(3H, s), 2.2–2.5(2H, m), 2.67(2H, t, J=5.7Hz), 2.7–3.0(1H, m), 3.3–3.8(1H, m), 3.92(2H, t, J=5.7Hz), 5.03 (1H,s), 5.29(1H, s), 5.65 (1H,s), 5.86(2H,s), 6.1–6.8(3H, m), 6.9–7.7(7H, m) |
| 45 | 3,5-di-tert-butyl-4-hydroxyphenyl | 3 | 4-methoxyphenyl | 1.42(18H, s), 1.4–1.9(2H, m), 2.20(3H, s), 2.2–2.5(2H, m), 2.64(2H, t, J=5.7Hz), 2.7–3.0 (1H, m), 3.4–3.7(1H, m), 3.79 (3H,s), 3.92(2H, t, J=5.7Hz) 4.98(1H, s), 5.30(1H, s), 5.64(1H, s), 5.88(2H, s), 6.1 –6.8(3H,m), 6.85(2H, d, J= 8.7Hz), 7.15(2H, s), 7.41 (2H, d, J=8.7Hz) |

Example 46

Preparation of 2-(3, 5-Di-tert-butyl-4-hydroxyphenyl)-3-[3-[N-methyl-N-[2-(3,4-methylenedioxyphenoxy)ethyl]amino]-propyl]-5-ethoxycarbonylmethyl-1,3-thiazolidin-4-one According to the procedure for Example 26-A, using 2-(3,5-di-tert-butyl-4-hydroxyphenyl)-3-(3-bromopropyl)-5-ethoxycarbonylmethyl-1,3-thiazolidin-4-one obtained in Reference Example 45 instead of 2-(3,5-di-tert-butyl-4-hydroxyphenyl)-3-(3-bromopropyl)-1,3-thiazolidin-4-one, the title compound was prepared as. colorless crystals. mp 88–89° C. NMR (CDCl$_3$) (200 MHz) δ: 1.26 (3H, t, J=7.1 Hz), 1.41 (18H, s), 1.4–1.9 (2H, m), 2.19 (3H, s), 2.3–2.5 (2H, m), 2.67 (2H, t, J=5.7 Hz), 2.7–3.0 (2H, m), 3.2–3.7

Example 48

Preparation of 2-(3,5-Di-tert-butyl-4-hydroxyphenyl)-3-[3-[N-methyl-N-[2-(3,4-methylenedioxyphenoxy)ethyl]-amino]propyl]-5-carboxymethyl-1,3-thiazolidin-4-one In ethanol (5 ml) was dissolved 2-(3,5-di-tert-butyl-4-hydroxyphenyl)-3-[3-[N-methyl-N-[2-(3,4-methylenedioxyphenoxy)ethyl]amino]propyl]-5-ethoxycarbonylmethyl-1,3thiazolidin-4-one (100 mg) prepared in Example 46, and a solution of sodium hydroxide (200 mg) in 20% water-containing ethanol was added, then the mixture was stirred at room temperature overnight. After completion of the reaction, the mixture was neutralized with 1N hydrochloric acid and concentrated under reduced pressure. To the residue was added a mixture of water (50 ml) and chloroform (50 ml), and the mixture was stirred. The organic layer was separated, washed with brine, and dried over anhydrous sodium sulfate. The solvent was evaporated under reduced pressure, and the residue was triturated with n-hexane to afford 80 mg (84%) of the title compound as a pale yellow solid. NMR (CDCl$_3$) (200 MHz) δ: 1.41 (18/2H, s), 1.42 (18/2H, s), 1.4–2.4 (2H, m), 2.85 (3/2H, s), 2.90 (3/2H, s), 2.7–3.8 (8H, m), 4.1–4.7 (3H, m), 5.2–5.4 (1H, m), 5.66 (1/2H, brs), 5.81 (1/2H, brs), 5.89 (2H, s), 6.2–6.7 (3H, m), 7.13 (2/2H, s), 7.14 (2/2H, s)

Example 49

Preparation of 2-(3,5-Di-tert-butyl-4-hydroxyphenyl)-3-[3-[N-methyl-N-[2-(3,4-methylenedioxyphenoxy)ethyl]-amino]propyl]-5-(2-hydroxyethyl)-1,3-thiazolidin-4-one To a solution of 2-(3,5-di-tert-butyl-4-hydroxyphenyl)-3-[3-[N-methyl-N-[2-(3,4-methylenedioxy-phenoxy)ethyl]amino]propyl]-5-ethoxycarbonylmethyl-1,3-thiazolidin-4-one (80 mg) prepared in Example 46 in dry tetrahydrofuran (5 ml) was added lithium aluminum hydride (20 mg) at −78° C., and the mixture was stirred at 0° C. for 3 hours. To the mixture was added water-containing tetrahydrofuran (5 ml), followed by stirring at that temperature for 1 hour. The mixture was neutralized with 1N hydrochloric acid, concentrated under reduced pressure. The residue was purified by silica gel column chromatography (eluent; chloroform-methanol, 95:5) to afford 68 mg (86%) of the title compound as a colorless oil. NMR (CDCl$_3$) (200 MHz) δ: 1.41 (18H, s), 1.3–1.8 (4H, m), 2.19 (3H, s), 2.2–2.5 (3H, m), 2.67 (2H, t, J=5.7 Hz), 2.7–2.9 (1H, m), 3.4–3.6 (1H, m), 3.8–4.0 (2H, m), 3.91 (2H, t, J=5.7 Hz), 4.04 (1H, t, J=5.7 Hz), 5.33 (1H, s), 5.60 (1H, s), 5.90 (2H, s), 6.2–6.7 (3H, m), 7.12 (2H, s)

Reference Example 47

Preparation of 2-(3,5-Di-tert-butyl-4-hydroxyphenyl)-3-(3-chloropropyl)-5-(1-pyrrolidinecarbonylmethyl)-1,3-thiazolidin-4-one To a suspension of 2-(3,5-di-tert-butyl-4-hydroxyphenyl)-3-(3-hydroxypropyl)-5-carboxymethyl-1,3-thiazolidin-4-one (0.61 g) obtained in Reference Example 41 in dichloromethane (20 ml) were added thionyl chloride (0.38 g) and a catalytic amount of dimethylformamide, and the mixture was refluxed for 2 hours. After allowing to cool, the mixture was added dropwise to a solution of pyrrolidine (1.02 g) in dichloromethane (20 ml) under cooling with ice, and stirred at that temperature for 1 hour. After completion of the reaction, the reaction mixture was poured into ice-water and extracted with chloroform. The organic layer was washed successively with 1N hydrochloric acid and brine, and dried over anhydrous sodium sulfate. The solvent was evaporated under reduced pressure, and the residue was purified by silica gel column chromatography (eluent; chloroform-methanol, 97:3) and then recrystallized from chloroform/n-hexane to yield 0.65 g (92%) of the title compound as colorless crystals. mp 193–194° C. NMR (CDCl$_3$) (200 MHz) δ: 1.43 (18H, s), 1.4–2.2 (6H, m), 2.5–3.1 (2H, m), 3.2–3.7 (8H, m), 4.2–4.5 (1H, m), 5.29 (1H, s), 5.53 (1H, s), 7.08 (2H, s)

Reference Examples 48 to 50

Each compound shown in Table 36 was prepared according to the procedure for Reference Example 47, using an appropriate amine in each case.

TABLE 36

[Structure: thiazolidinone ring with R$^1$ at 2-position, R$^5$ at 5-position, and (CH$_2$)$_n$—Cl on N]

| Ref. Ex. No. | R$^1$ | n | R$^5$ | Physical Properties ($^1$H-NMR (CDCl$_3$)) |
|---|---|---|---|---|
| 48 | [3,5-di-tert-butyl-4-hydroxyphenyl] | 3 | [—CH$_2$C(O)NMe$_2$ type group] | 1.43(18H, s), 1.4–2.2(2H, m), 2.5–3.2(2H, m), 2.95(3H, s), 3.00(3H, s), 3.3–3.8(4H, m), 4.1–4.5(1H, m), 5.29(1H, s), 5.53(1H, s), 7.09(2H, s) |
| 49 | [3,5-di-tert-butyl-4-hydroxyphenyl] | 3 | [—CH$_2$C(O)-morpholinyl] | 1.42(18H, s), 1.6–2.1(2H, m), 2.6–3.2(2H, m), 3.3–3.8 (12H, m), 4.2–4.5(1H, m), 5.30(1H, s), 5.53(1H, s), 7.08(2H, s) |

TABLE 36-continued

| Ref. Ex. No. | R¹ | n | R⁵ | Physical Properties (¹H-NMR (CDCl₃)) |
|---|---|---|---|---|
| 50 | (3,5-di-tert-butyl-4-hydroxy-... with additional methyl) phenol group | 3 | CH₃CH₂-C(=O)-N(Me)-CH₂CH₂-NMe₂ | 1.41(18H, s), 1.6–2.1(2H, m), 2.24(6H, s), 2.3–2.6(2H, m), 2.6–3.1(2H, m), 2.94(3 × 2/5H, s), 3.01(3 × 3/5H, s), 3.2–3.8(7H, m), 4.1–4.5(1H, m), 5.28(1H, s), 5.52(1H, s), 7.08 (2H, s) |

Example 50

Preparation of 2-(3,5-Di-tert-butyl-4-hydroxyphenyl)-3-[3-[N-methyl-N-[2-(3,4-methylenedioxyphenoxy)ethyl]amino]propyl]-5-(1-pyrrolidinecarbonylmethyl)-1,3-thiazolidin-4-one The title compound was obtained as a pale brown oil according to the procedure for Example 1, using 2-(3,5-di-tert-butyl-4-hydroxyphenyl)-3-(3-chloropropyl)-5-(1-pyrrolidinecarbonylmethyl)-1,3-thiazolidin-4-one obtained in Reference Example 47 instead of 2-(3,5-diisopropyl-4-hydroxyphenyl)-3-(3-chloropropyl)-1,3-thiazolidin-4-one.

NMR (CDCl₃) (200 MHz) δ: 1.41 (18H, s), 1.4–2.1 (6H, m), 2.20 (3H, s), 2.2–2.5 (2H, m), 2.5–3.1 (4H, m), 3.2–3.8 (6H, m), 3.93 (2H, t, J=5.7 Hz), 4.2–4.5 (1H, m), 5.29 (1H, s), 5.57 (1H, s), 5.88 (2H, s), 6.1–6.8 (3H, m), 6.9–7.2 (2H, m)

Examples 51 to 53

Each compound shown in Table 37 was prepared according to the procedure for Example 50, using each of the compounds prepared in Reference Examples 48 to 50 instead of 2-(3,5-di-tert-butyl-4-hydroxyphenyl)-3-(3-chloropropyl)-5-(1-pyrrolidinecarbonylmethyl)-1,3-thiazolidin-4-one.

TABLE 37

| Ref. Ex. No. | R¹ | n | R⁵ | Physical Properties (¹H-NMR (CDCl₃)) |
|---|---|---|---|---|
| 51 | 3,5-di-tert-butyl-4-hydroxy-(with methyl) phenyl | 3 | CH₃CH₂-C(=O)-NMe₂ | 1.41(18H, s), 1.4–1.9(2H, m), 2.20(3H, s), 2.2–2.5(2H, m), 2.5–3.1(4H, m), 2.94(3H, s), 2.98(3H, s), 3.2–3.8(2H, m), 3.92(2H, t, J=5.7Hz), 4.1–4.5 (1H, m), 5.25(1H, s), 5.56(1 H, s), 5.88(2H, s), 6.1–6.8 (3H,m), 6.9–7.29(2H, m) |

TABLE 37-continued

| Ref. Ex. No. | R¹ | n | R⁵ | Physical Properties ($^1$H-NMR (CDCl$_3$)) |
|---|---|---|---|---|
| 52 | 3,5-di-tert-butyl-4-hydroxyphenyl | 3 | -C(O)-morpholine (propanoyl morpholine) | 1.41(18H, s), 1.4–2.0(2H, m), 2.20(3H, s), 2.2–3.0(5H, m), 3.1–3.8(11H, m), 3.92(2H, t, J=5.7Hz), 4.1–4.5(1H, m), 5.28(1H, s), 5.57(1H, s), 5.88(2H, s), 6.1–6.8 (3H, m), 6.9–7.29(2H, m) |
| 53 | 3,5-di-tert-butyl-4-hydroxyphenyl | 3 | -C(O)-N(Me)-CH$_2$CH$_2$-NMe$_2$ | 1.41(18H, s), 2.0–3.1(7H, m), 2.20(3H, s), 2.31(6H, s), 2.94 (3 × 2/5H, s), 3.01(3 × 3/5H, s), 3.2–3.8(5H, m), 3.92(2H, t, J=5.7Hz), 4.1–4.5(H, m), 5.28(1H, s), 5.56(1H, s), 5.88(2H, s), 6.1–6.8(3H, m), 7.0–7.2(2H, m) |

Reference Example 51

Preparation of 2-(3,5-Di-tert-butyl-4-hydroxyphenyl)-3-(3-bromopropyl)-5-methoxy-1,3-thiazolidin-4-one To a solution of 2-(3,5-di-tert-butyl-4-hydroxyphenyl)-3-(3-bromopropyl)-1,3-thiazolidin-4-one (1.0 g) prepared in Reference Example 29 in dichloromethane (15 ml) was added dropwise sulfuryl chloride (0.36 g) under cooling with ice-water, and the mixture was stirred at room temperature for 1.5 hours. The solvent was evaporated under reduced pressure, and methanol (10 ml) was added to the residue, and the mixture was stirred at room temperature overnight. The mixture was concentrated under reduced pressure, and the residue was purified by silica gel column chromatography (eluent; chloroform) to afford 0.59 g (48%) of the title compound as a pale brown oil. NMR (CDCl$_3$) (200 MHz) δ: 1.42 (18H, s), 1.5–2.3 (2H, m), 2.8–3.6 (4H, m), 3.46 (3×2/5H, s), 3.52 (3×3/5H, s), 5.2–6.1 (3H, m), 7.08 (2×2/5H, s), 7.12 (2×3/5H, s)

Reference Examples 52 and 53

Each compound shown in Table 38 was prepared according to the procedure for Reference Example 51, using ethylene glycol instead of methanol.

TABLE 38

[Structure: thiazolidinone with R¹ at 2-position, R⁵ at 5-position, N-(CH₂)ₙ-Br]

| Ref. Ex. No. | R¹ | n | R⁵ | Physical Properties ($^1$H-NMR (CDCl$_3$)) |
|---|---|---|---|---|
| 52 | 3,5-di-tert-butyl-4-hydroxyphenyl | 3 | —O—CH₂CH₂—OH | 1.43(18H, s), 1.7–2.4(2H, m), 2.8–4.1(9H, m), 5.2–5.9(3H, m), 7.12(2 × 1/2H, s), 7.2(2 × 1/2H, s) |
| 53 | 3,5-di-tert-butyl-4-hydroxyphenyl | 3 | 1,3-dioxolan-2-yl (spiro) | 1.43(18H, s), 1.7–2.3(2H, m), 2.9–3.7(4H, m), 4.1–4.5(4H, m), 5.35(1H, s), 5.53(1H, s) 7.22(2H, s) |

Example 54

Preparation of 2-(3,5-Di-tert-butyl-4-hydroxyphenyl)-3-[3-[N-methyl-N-[2-(3,4-methylenedioxyphenoxy)ethyl]amino]propyl]-5-methoxy-1,3-thiazolidin-4-one

The title compound was obtained as a pale yellow oil according to the procedure for Example 26-A, using 2-(3,5-di-tert-butyl-4-hydroxyphenyl)-3-(3-bromopropyl)-5-methoxy-1,3-thiazolidin-4-one prepared in Reference Example 51 instead of 2-(3,5-di-tert-butyl-4-hydroxyphenyl)-3-(3-bromopropyl)-1,3-thiazolidin-4-one.

NMR (CDCl$_3$) (270 MHz) δ: 1.41 (18H, s), 1.4–1.9 (2H, m), 2.18 (3×2/5H, s), 2.22 (3×3/5H, s), 2.2–3.1 (5H, m), 3.46 (3×2/5H, s), 3.51 (3×3/5H; s), 3.5–3.7 (1H, m), 3.8–4.1 (2H, m), 5.2–5.8 (3H, m), 5.90 (2H, s), 6.1–6.8 (3H, m), 7.21 (2×2/5H, s), 7.26 (2×3/5H, s)

Examples 55 and 56

Each compound shown in Table 39 was prepared according to the procedure for Example 54, using each of the compounds prepared in Reference Examples 52 and 53 instead of 2-(3,5-di-tert-butyl-4-hydroxyphenyl)-3-(3-bromopropyl)-5-methoxy-1,3-thiazolidin-4-one.

TABLE 39

![Structure with R⁵, S, R¹, N, (CH₂)ₙ, N-Me, O, and benzodioxole group]

| Ex. No. | R¹ | n | R⁵ | Physical Properties (¹H-NMR (CDCl₃)) |
|---------|----|----|----|--------------------------------------|
| 55 | [3,5-di-tert-butyl-4-hydroxyphenyl] | 3 | —O—CH₂CH₂OH | 1.41(18H, s), 1.4–2.0(2H, m), 2.18(3 × 2/5H, s), 2.22 (3 × 3/5H, s), 2.2–3.0(5H, m) 3.4–4.1(8H, m), 5.2–5.9(3H, m), 5.90(2H, s), 6.1–6.8(3H, m), 7.09(2 × 2/5H, s), 7.18(2 × 3/5H, s) |
| 56 | [3,5-di-tert-butyl-4-hydroxyphenyl] | 3 | [2-methyl-1,3-dioxolan-2-yl] | 1.41(18H, s), 1.4–2.0(2H, m), 2.21(3H, s), 2.2–2.6(2H, m), 2.68(2H, t, J=5.9Hz), 2.7–3.0(1H, m), 3.4–3.7(1H, m), 3.93(2H, t, J=5.9Hz), 4.0–4.5(4H, m), 5.31(1H, s), 5.60(1H, s), 5.90(2H, s), 6.1–6.8(3H, m), 7.18(2H, s) |

Example 57

Preparation of 2-(3,5-Di-tert-butyl-4-hydroxyphenyl)-3-[3-[N-methyl-N-[2-(3,4-methylenedioxyphenoxy)ethyl]amino]propyl]-1,3-thiazolidin-4-thione In THF (5 ml) were suspended 2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one (217 mg) obtained in Reference Example 26-A and Lawesson's reagent (194 mg), and the suspension was stirred at room temperature for 5 hours. The solvent was evaporated under reduced pressure, and to the residue was added water (20 ml), then the mixture was extracted with chloroform. The organic layer was washed successively with water and brine, and dried over anhydrous sodium sulfate. The solvent was removed by evaporation under reduced pressure, and the residue was purified by silica gel column chromatography (eluent; chloroform-methanol, 99:1) to afford 181 mg (81%) of the title compound as a pale yellow oil. NMR (CDCl₃) (200 MHz) δ: 1.41 (18H, s), 1.3–1.8 (2H, m), 2.20 (3H, s), 2.3–2.5 (2H, m), 2.70 (2H, t, J=5.7 Hz), 3.1–3.3 (1H, m), 3.93 (2H, t, J=5.7 Hz), 3.9–4.1 (1H, m), 4.26 and 4.40 (2H, ABq, J=16.0 Hz), 5.34 (1H, s), 6.18 (2H, s), 6.04 (1H, s), 6.2–7.0 (3H, m), 7.07 (2H, s)

Example 58

Preparation of N-[3-[N-Methyl-N-[2-(3,4-methylenedioxyphenoxy)ethyl]amino]-propyl]-3,5-di-tert-butyl-4-hydroxybenzamide To a suspension of 3,5-di-tert-butyl-4-hydroxybenzoic acid (1.00 g) in tetrahydrofuran (17 ml) were added oxalyl chloride (0.76 g) and a catalytic amount of dimethylformamide at 0° C., the mixture was stirred at room temperature for 1 hour. The solvent and excess oxalyl chloride were removed under reduced pressure, and tetrahydrofuran (8 ml) was added to the residue. The resultant solution was added dropwise to a solution of 3-[N-methyl-N-[2-(3,4-methylenedioxyphenoxy)ethyl]amino]propylamine (1.01 g) and triethylamine (0.41 g) in tetrahydrofuran (13 ml) at 0° C., and the mixture was stirred at room temperature for 6 hours. The reaction mixture was poured into cold water, and the product was extracted with chloroform. The organic layer was washed with brine and dried over anhydrous sodium sulfate. The solvent was evaporated under reduced pressure, and the residue was purified by silica gel column chromatography (eluent; chloroform-methanol, 97:3) to afford 1.35 g (70%) of the title compound as a pale brown oil. NMR (CDCl₃) δ: 1.34 (18×1/3H, s),, 1.43 (18×2/3H, s), 1.7–1.9 (2H, m), 2.41 (3H, s), 2.6–2.7 (2H, m), 2.8–2.9 (2H, m), 3.5–3.6 (2H, m), 3.9–4.1 (2H, m), 5.48 (1H, s), 5.86 (2×2/3H, s), 5.88 (2×1/3H, s), 6.1–6.7 (3H, m), 7.64 (2×2/3H, s), 7.79 (2×1/3H, s), 7.8–8.0 (1H, brs)

Example 59

According to the procedure for Example 58, 3,5-di-tert-butyl-4-hydroxybenzenesulfonyl chloride was prepared from 3,5-di-tert-butyl-4-hydroxybenzenesulfonic acid and thionyl chloride instead of 3,5-di-tert-butyl-4-hydroxybenzoic acid and oxalyl chloride, and then converted to N-[3-[N-methyl-N-[2-(3,4-methylenedioxyphenoxy)-ethyl]amino]propyl]-3,5-di-tert-butyl-4-hydroxybenzenesulfonamide to afford a colorless oil. NMR (CDCl₃) (200 MHz) δ: 1.43 (18H, s), 1.3–1.8 (2H, m), 2.25 (3H, s), 2.51 (2H, t, J=6.3 Hz), 2.72 (2H, t, J=6.3 Hz), 3.07 (2H, t, J=6.3 Hz), 3.97 (2H, t, J=6.3 Hz), 5.66 (1H, s), 5.90 (2H, s), 6.2–6.7 (3H, m), 7.67 (2H, s)

Example 60

Preparation of N-[3-[N-Methyl-N-[2-(3,4-methylenedioxyphenoxy)ethyl]amino]propyl]-3,5-di-tert-butyl-4-hydroxybenzothioamide The title compound was obtained as pale yellow crystals according to the procedure for Example 57, using N-[3-[N- methyl-N-[2-(3,4-methylenedioxyphenoxy)ethyl]-amino]propyl]-3,5-di-tert-butyl-4-hydroxybenzamide prepared in Example 58 instead of 2-(3,5-di-tert-butyl-4-hydroxyphenyl)-3-[3-[N-methyl-N-[2-(3,4-methylenedioxyphenoxy)-ethyl]amino]propyl]-1,3-thiazolidin-4-one. mp 114–115° C. NMR (CDCl$_3$) (200 MHz) δ: 1.42 (18H, s), 1.6–2.1 (2H, m), 2.21 (3H, s), 2.5–2.9 (4H, m), 3.80 (2H, t, J=5.7 Hz), 3.8–4.1 (2H, m), 5.44 (1H, s), 5.82 (2H, s), 5.8–6.7 (3H, m), 7.5–7.8 (3H, m)

Example 61

Preparation of N-Cyano-N'-[3-[N-methyl-N-[2-(3,4-methylenedioxyphenoxy)ethyl]amino]-propyl]-3,5-di-tert-butyl-4-hydroxybenzamidine To a solution of N-[3-[N-methyl-N-[2-(3,4-methylenedioxyphenoxy)ethyl]amino]propyl]-3,5-di-tert-butyl-4-hydroxybenzothioamide (1.0 g) obtained in Example 60 in dry tetrahydrofuran was added sodium hydride (0.16 g) at 0° C. under a nitrogen atmosphere, and the mixture was stirred at the same temperature for 1 hour. To the mixture was added ethyl iodide (0.31 g), followed by stirring at room temperature for 2 hours. The mixture was again cooled to 0° C., and cyanamide (0.84 g) was added thereto, followed by stirring at room temperature for 15 hours. After completion of the reaction, the mixture was poured into ice-water, and the product was extracted with chloroform. The organic layer was washed with brine and dried over anhydrous sodium sulfate. The solvent was removed by evaporation under reduced pressure, and the residue was purified by silica gel column chromatography (eluent; chloroform-methanol, 99:1) to afford 0.70 g (69%) of the title compound as pale yellow crystals. mp 129–130° C. NMR (CDCl$_3$) (200 MHz) δ: 1.45 (18H, s), 1.6–2.1 (2H, m), 2.20 (3H, s), 2.6–3.0 (4H, m), 3.6–3.8 (2H, m), 3.83 (2H, t, J=5.7 Hz), 5.56 (1H, s), 5.84 (2H, s), 5.8–6.8 (3H, m), 7.48 (2H, s), 8.44 (1H, brs)

Reference Example 54

Preparation of 3-(3-Bromopropyl)-5-(3,5-di-tert-butyl-4-hydroxyphenyl)-1,3,4-oxadiazol-2(3H)-one To a solution of 5-(3,5-di-tert-butyl-4-hydroxyphenyl)-1,3,4-oxadiazol-2(3H)-one (0.50 g) in dimethylformamide (8 ml) were added sodium carbonate (0.36 g) and 1,3-dibromopropane (1.74 g), followed by stirring at room temperature for 5 hours. After completion of the reaction, the reaction mixture was poured into ice-water, and the product was extracted with ethyl acetate. The organic layer was dried over anhydrous sodium sulfate, and the solvent was evaporated under reduced pressure. The residue was purified by silica gel column chromatography (eluent; chloroform) and then recrystallized from chloroform/n-hexane to afford 0.45 g (63%) of the title compound as colorless crystals. mp 130–131° C. NMR (CDCl$_3$) (200 MHz) δ: 1.46 (18H, s), 2.1–2.6 (2H, m), 3.46 (2H, t, J=6.6 Hz), 3.93 (2H, t,J=6.6 Hz), 5.60 (1H, s), 7.63 (2H, s)

Reference Examples 55 to 58

Each compound shown in Table 40 was prepared according to the procedure for Reference Example 54, using an appropriate 5-membered heterocyclic compound instead of 5-(3,5-di-tert-butyl-4-hydroxyphenyl)-1,3,4-oxadiazol-2(3H)-one in each case.

TABLE 40

Structure: HO-[3,5-di-tert-butylphenyl]-A-(CH$_2$)$_n$-Br (* marks attachment to phenyl, ** marks attachment to (CH$_2$)$_n$)

| Ref Ex. No. | A | n | Physical Properties ($^1$H-NMR (CDCl$_3$)) |
|---|---|---|---|
| 55 | 1,3,4-thiadiazol-2(3H)-one (S, N–N, C=O; * at C-5, ** at N-3) | 3 | 1.47(18H, s), 2.3–2.5(2H, m), 3.47(2H, t, J=6.6Hz), 4.12(2H, t, J=6.6Hz), 5.55(1H, s), 7.47(2H, s) |
| 56 | 4-ethyl-1,2,4-triazol-3(2H)-one (N-Et, N–N, C=O; * at C-5, ** at N-2) | 3 | 1.32(3H, t, J=7.2Hz), 1.46 (18H, s), 2.2–2.6(2H, m), 3.49(2H, t, J=6.6Hz), 3.77(2H, q, J=7.2Hz), 4.01(2H, t, J=6.6Hz), 5.50(1H, s), 7.33(2H, s) |
| 57 | 1,3,4-oxadiazol-2-yl (N–O, N, O; * at C-5, ** at O) | 3 | 1.43(18H, s), 2.0–2.7(2H, m), 3.50(2H, t, J=6.6Hz), 3.70(2H, t, J=6.6Hz), 5.06(1H, s), 6.93(2H, s) |
| 58 | 1,3,4-thiadiazol-2-oxide (N–O, N, S=O; * at C-5, ** at N) | 3 | 1.44(18H, s), 2.2–2.6(2H, m), 3.54(2H, t, J=6.6Hz), 3.73(2H, t, J=6.6Hz), 5.23(1H, s), 7.10(2H, s) |

Example 62

Preparation of 5-(3,5-Di-tert-butyl-4-hydroxyphenyl)-3-[3-[N-methyl-N-[2-(3,4-methylenedioxyphenoxy)-ethyl]amino]propyl]-1.34-oxadiazol-2(3H)-one The title compound was obtained as a colorless oil according to the procedure for Example 26-A, using 3-(3-bromopropyl)- 5-(3,5-di-tert-butyl-4-hydroxyphenyl)-1,3,4-oxadiazol-2(3H)-one obtained in Reference Example 54 instead of 2-(3,5-di-tert-butyl-4-hydroxyphenyl)-3-(3-bromopropyl)-1,3-thiazolidin-4-one. NMR (CDCl$_3$) (270 MHz) δ: 1.45 (18H, s), 1.8–2.2 (2H, m), 2.35 (3H, s), 2.4–3.0 (4H, m), 3.7–4.2 (4H, m), 5.60 (1H, s), 5.88 (2H, s), 6.1–6.8 (3H, m), 7.65 (2H, s)

Examples 63 to 66

Each compound shown. in Table 41 was prepared according to the procedure for Example 62, using each of the compounds shown in Table 40 instead of 3-(3-bromopropyl)-5-(3,5-ditert-butyl-4-hydroxyphenyl)-1,3,4-oxadiazol-2(3H)-one.

TABLE 41

HO—[3,5-di-tert-butyl phenyl]—A—(CH₂)ₙ—N(Me)—CH₂CH₂—O—[benzodioxole]

| Ex. No. | A | n | Physical Properties (¹H-NMR (CDCl₃)) |
|---|---|---|---|
| 63 | *—[thiadiazolone ring with S, N—N, =O; ** on N] | 3 | 1.46(18H, s), 1.9–2.1(2H, m), 2.36(3H, s), 2.58(2H, t, J=7.2Hz), 2.79(2H, t, J=6.6Hz), 3.99(2H, t, J=6.6Hz), 4.02 (2H, t, J=7.2Hz), 5.53(1H, s), 5.89(2H, s), 6.1–6.8(3H, m), 7.46(2H, s) |
| 64 | *—[imidazolone with Et, N—N, =O; ** on N] | 3 | 1.32(3H, t, J=7.2Hz), 1.46 (18H, s), 1.8–2.2(2H, m), 2.34(3H, s), 2.56(2H, t, J=6.6Hz), 2.78(2H, t, J=5.7Hz), 3.76(2H, q, J=7.2Hz), 3.88 (2H, t, J=6.6Hz), 3.98(2H, t, J=5.7Hz), 5.51(1H, s), 5.87(2H, s), 6.1–6.8(3H, m), 7.32(2H, s) |
| 65 | *—[oxadiazole ring N—O, N, O—**] | 3 | 1.42(18H, s), 1.7–2.2(2H, m), 2.32(3H, s), 2.59(2H, t, J=6.6Hz), 2.77(2H, t, J=5.7Hz), 3.60(2H, t, J=6.6Hz), 3.96 (2H, t, J=5.7Hz), 5.05(1H, s), 5.88 (2H, s), 6.1–6.8(3H, m), 6.95 (2H, s) |
| 66 | *—[oxadiazolone N—O, N—**, =O] | 3 | 1.41(18H, s), 1.7–2.2(2H, m), 2.32(3H, s), 2.58(2H, t, J=6.6Hz), 2.77(2H, t, J=5.7Hz), 3.60(2H, t, J=6.6Hz), 3.95 (2H, t, J=5.7Hz), 5.05(1H, s), 5.85(2H, s), 6.1–6.8(3H, m), 6.94(2H, s) |

Reference Example 59

Preparation of 5-(3,5-Di-tert-butyl-4-hydroxyphenyl)-1-(3-hydroxypropyl)imidazole To a solution of 3-hydroxy-N-(3,5-di-tert-butyl-4-hydroxybenzylidene)propylamine (1.50 g) in methanol (50 ml) were added tosylmethyl isocyanide (1.68 g) and potassium carbonate (1.43 g), and the mixture was stirred at room temperature for 16 hours. After completion of the reaction, the reaction mixture was poured into ice-water and extracted with dichloromethane. The organic layer was dried over anhydrous sodium sulfate, and the solvent was evaporated under reduced pressure. The resulting crude crystals were recrystallized from a chloroform/diethyl ether to afford 1.41 g (82%) of the title compound as pale yellow crystals. mp 166–167° C. NMR (CDCl₃) δ: 1.43 (18H, s), 1.5–2.3 (3H, m), 3.53 (2H, t,J=6.6 Hz), 4.08 (2H, t, J=6.6 Hz), 5.30 (1H, brs), 6.92 (1H, brs), 7.10 (2H, s), 7.50 (1H, s)

Reference Example 60

Preparation of 5-(3,5-Di-tert-butyl-4-hydroxyphenyl)-1-(3-chloropropyl)imidazole To a solution of 5-(3,5-di-tert-butyl-4-hydroxyphenyl)-1-(3-hydroxypropyl)imidazole (1.20 g) obtained in Reference Example 59 in dichloromethane (30 ml) were added thionyl chloride (0.65 g) and a catalytic amount of dimethylformamide, and the mixture was refluxed for 2 hours. After allowing to cool, the reaction mixture was poured into a 5% aqueous solution of sodium carbonate cooled with ice-water, and the product was extracted with dichloromethane. The organic layer was dried over anhydrous sodium sulfate, and the solvent was evaporated under reduced pressure. The resulting crude product was recrystallized from a dichloromethane/diethyl ether to afford 1.09 g (86%) of the title compound as pale yellow crystals. mp 178–179° C. NMR (CDCl₃) (60 MHz) δ: 1.43 (18H, s), 1.6–2.8 (2H, m), 3.35 (2H, t,J=6.6 Hz), 4.15 (2H, t, J=6.6 Hz), 5.45 (1H, brs), 6.90 (1H, s), 7.05 (2H, s), 7.43 (1H, s)

Example 67

Preparation of 5-(3,5-Di-tert-butyl-4-hydroxyphenyl)-1-[3-[N-methyl-N-[2-(3,4-methylenedioxyphenoxy)ethyl]amino]1propyl] imidazole The title compound was obtained as a colorless oil according to the procedure for Example 1, using 5-(3,5-di-tert-butyl-4-hydroxyphenyl)-1-(3-chloropropyl)imidazole obtained in Reference Example 60 instead of 2-(3,5-diisopropyl-4-hydroxyphenyl)-3-(3-chloropropyl)-1,3-thiazolidin-4-one. NMR (CDCl₃) (200 MHz) δ: 1.43 (18H, s), 1.5–2.0 (2H, m), 2.16 (3H, s), 2.32 (2H, t, J=6.6 Hz), 2.64 (2H, t,J=5.7 Hz), 3.88 (2H, t, J=5.7 Hz), 3.98 (2H, t, J=6.6 Hz), 5.35 (1H, brs), 5.87 (2H, s), 6.1–6.8 (3H, m), 6.96 (1H, s), 7.12 (2H, s), 7.52 (1H, s)

Example 68

Preparation of 2-(3,5-Di-tert-butyl-4-hydroxyphenyl)-3-[3-[N-methyl-N-[2-(3,4-methylenedioxyphenoxy)-ethyl]amino]propyl]-1,3-thiazolidin-4-one-1-oxide To a solution of 2-(3,5-di-tert-butyl-4-hydroxyphenyl)-3-[3-[N-methyl-N-[2-(3,4-methylenedioxy-phenoxy)-ethyl]amino]propyl]-1,3-thiazolidin-4-one (0.30 g) obtained in Example 26-A or 26-B in acetic acid (5 ml) was added 35% aqueous solution of hydrogen peroxide (0.20 g), and the mixture was stirred at room temperature overnight. After completion of the reaction, the reaction mixture was added to a mixture of ethyl acetate and a 5% aqueous solution of sodium carbonate and stirred. The organic layer was separated, dried over anhydrous sodium sulfate. The solvent was evaporated under reduced pressure, and the residue was purified by silica gel column chromatography (eluent; chloroform-methanol, 98:2) to afford 0.12 g (39%) of the title compound as a colorless oil. MS (m/z): 558 (M⁺) NMR (CDCl₃) (200 MHz) δ: 1.41 (18H, s), 1.4–2.0 (2H, m), 2.28 (3H, s), 2.3–2.7 (2H, m), 2.72 (2H, t, J=5.7 Hz), 2.9–3.2 (1H, m), 3.37 and 3.69 (2H, ABq, J=16 Hz), 3.8–4.2 (3H, m), 5.40 (1H, s), 5.61 (1H, s), 5.87 (2H, s), 6.1–6.8 (3H, m), 6.94 (2H, s)

Reference Example 61

Preparation of 2-(3,5-Di-tert-butyl-4-hydroxyphenyl)-1,3-thiazolidine Hydrochloride In a mixed solvent of methanol (100 ml) and tetrahydrofuran (100 ml) was dissolved 5.0 g of 3,5-di-tert-butyl-4-hydroxybenzaldehyde (5.0 g), and solution of 2-aminoethanethiol (1.73 g) in methanol (10 ml) was added. Then the mixture was stirred at room temperature for 2 hours. After completion of the reaction, the solvent was evaporated under reduced pressure, and 200 ml of ice-water was added to the residue. The product was extracted with chloroform, and the organic layer was dried over anhydrous sodium sulfate. The solvent was evaporated under reduced pressure, and methanol-hydrochloric acid (5 ml) was added to the residue. The mixture was triturated with diethyl ether to yield 5.81 g (82%) of the title compound as a white powder. NMR (CDCl$_3$) (200 MHz) δ: 1.43 (18H, s), 2.9–3.2 (2H, m), 3.6–3.8 (1H, m), 3.8–4.0 (1H, m), 5.20 (1H, s), 5.46 (1H, s), 7.2–7.4 (2H, m)

Reference Example 62

Preparation of 2-(3,5-Di-tert-butyl-4-hydroxyphenyl)-3-acryloyl-1,3-thiazolidine To a suspension of 2-(3,5-di-tert-butyl-4-hydroxyphenyl)-1,3-thiazolidine hydrochloride (1.65 g) obtained in Reference Example 61 in tetrahydrofuran (20 ml) was added triethylamine (1.52 g), and acryloyl chloride (0.63 g) was added thereto at 0° C. The mixture was stirred at that temperature for 3 hours. After completion of the reaction, the reaction mixture was poured into ice-water; and the product was extracted with chloroform. The organic layer was washed successively with 1N hydrochloric acid, a saturated aqueous solution of sodium hydrogencarbonate, and brine, then dried over anhydrous sodium sulfate. The solvent was evaporated under reduced pressure, and the residue was purified by silica gel column chromatography (eluent; chloroform-methanol, 98:2) to afford 0.93 g (54%) of the title compound as colorless crystals. mp 147–149° C. NMR (CDCl$_3$) (200 MHz) δ: 1.40 (18H, s), 3.0–3.2 (2H, m), 3.8–4.0 (1H, m), 4.2–4.5 (1H, m), 5.20 (1H, brs), 5.5–5.8 (1H, m), 5.9–6.6 (3H, m), 6.98 (2H, brs)

Example 69

Preparation of 2-(3,5-Di-tert-butyl-4-hydroxyphenyl)-3-[3-[N-methyl-N-[2-(3,4-methylenedioxyphenoxy)ethyl]amino]propionyl]-1,3-thiazolidine To a solution of 2-(3,5-di-tert-butyl-4-hydroxyphenyl)-3-acryloyl-1,3-thiazolidine (0.35 g) obtained in Reference Example 62 in chloroform (5 ml) was added N-methyl-2-(3,4-methylenedioxyphenoxy)ethylamine (0.20 g), and the mixture was refluxed for 3 hours. After completion of the reaction, the solvent was evaporated under reduced pressure, and the residue was purified by silica gel column chromatography (eluent; chloroform-methanol, 98:2) to afford 0.41 g (76%) of the title compound as a colorless oil. NMR (CDCl$_3$) (200 MHz) δ: 1.41 (18H, s), 2.14 (3H, s), 2.2–2.7 (4H, m), 2.7–2.9 (2H, m), 2.9–3.2 (2H, m), 3.8–4.1 (3H, m), 4.2–4.4 (1H, m), 5.1–5.3 (1H, m), 5.89 (2H, s), 6.02 (1H, brs), 6.2–7.1 (5H, m)

Example 70

Preparation of (+)-2-(3,5-Di-tert-butyl-4-hydroxyphenyl)-3-[3-[N-methyl-N-[2-(3,4-methylenedioxyphenoxy)ethyl]amino]propyl]-1,3-thiazolidin-4-one The compound obtained in Example 26-A or 26-B and weighing 400 mg was subjected to HPLC using a column for optical resolution (CHIRALCEL OD; 2 cm (diameter)×25 cm) in several tens of divided fractions under conditions of a mobile phase of n-hexane-isopropyl alcohol, (80:20), a flow rate of 16 ml/min, and a detection wavelength of 280 nm to recover 180 mg of the title compound. The specific rotation of the hydrochloride of the resulting compound is as follows.

[α]$_D$=+36.14 (EtOH, c=0.332)

Example 71

Preparation of (−)-2-(3,5-Di-tert-butyl-4-hydroxyphenyl)-3-[3-[N-methyl-N-[2-(3,4-methylenedioxyphenoxy)ethyl]amino]propyl]-1,3-thiazolidin-4-one The compound obtained in Examples 26-A or 26-B and weighing 400 mg was subjected to HPLC in several tens of divided fractions under the same conditions as in Example 70 to obtain 170 mg of the title compound. The hydrochloride of the resulting compound had the following specific rotation.

[α]$_D$=−36.72 (EtOH, c=0.610)

Example 72

Preparation of 2,5-Trans-2-(3,5-di-tert-butyl-4-hydroxyphenyl)-3-[3-[N-methyl-[2-(3,4-methylenedioxyphenoxy)-ethyl]amino]propyl]-5-methyl-1,3-thiazolidin-4-one The compound obtained in Example 41-A or 41-B and weighing 500 mg was subjected to HPLC using a silica gel column (YMC-PackSIL SH-043-5, 2 cm (diameter)×25 cm) in several tens of divided fractions under conditions of a mobile phase of chloroform-isopropanol, (97:3), a flow rate of 12 ml/min, and a detection wavelength of 280 nm to recover 150 mg of the title compound. The stereochemistry was assumed from the $^1$H-NMR data of M. R. Johnson, et al. (M. R. Johnson, et al., *J. Org. Chem.*, 48, 494 (1983)). NMR (CDCl$_3$) (270 MHz) δ: 1.41 (18H, s), 1.5–1.9 (2H, m), 1.58 (3H, d, J=6.9 Hz), 2.23 (3H, s), 2.3–2.5 (2H, m), 2.69 (2H, t, J=5.6 Hz), 2.7–2.9 (1H, m), 3.5–3.7 (1H, m), 3.94 (2H, t, J=5.6 Hz), 4.02 (1H, dq, J=1.7, 6.9 Hz), 5.28 (1H, s), 5.57 (1H, d, J=1.7 Hz), 5.90 (2H, s), 6.2–6.8 (3H, m), 7.05 (2H, s)

Example 73

Preparation of 2,5-Cis-2-(3,5-di-tert-butyl-4-hydroxyphenyl)-3-[3-[N-methyl-N-[2-(3,4-methylenedioxyphenoxy)-ethyl]amino]propyl]-5-methyl-1,3-thiazolidin-4-one The compound obtained in Example 41-A or 41-B and weighing 500 mg was subjected to HPLC in several tens of divided fractions under the same conditions as in Example 72 to obtain 140 mg of the title compound. The stereochemistry was assumed from the $^1$H-NMR data of M. R. Johnson, et al. (M. R. Johnson, et al., *J. Org. Chem.*, 48, 494 (1983)). NMR (CDCl$_3$) (270 MHz) δ: 1.43 (18H, s), 1.2–2.0 (2H, m), 1.65 (3H, d, J=6.9 Hz), 2.20 (3H, m), 2.2–2.5 (2H, m), 2.67 (2H, t, J=5.6 Hz), 2.7–3.0 (1H, m), 3.4–3.8 (1H, m), 3.92 (2H, t, J=5.6 Hz), 4.02 (1H, q, J=6.9 Hz), 5.30 (1H, s), 5.55 (1H, s), 5.91 (2H, s), 6.2–6.8 (3H, m), 7.12 (2H, s)

Example 74

Preparation of (+)-2,5-Cis-2-[3,5-di-tert-butyl-4-hydroxyphenyl)-3-[3-[N-methyl-N-[2-(3,4-methylenedioxyphenoxy)-ethyl]amino]propyl]-5-methyl-1,3-thiazolidin-4-one The compound obtained in Example 73 was subjected to HPLC in several tens of divided fractions under the same conditions as in Example 70 to recover the title compound. The resulting compound had the following specific rotation.

[α]$_D$=+27.59 (CHCl$_3$, C=1.000)

Example 75

Preparation of (−)-2,5-Cis-2-[3,5-di-tert-butyl-4-hydroxyphenyl)-3-[3-[N-methyl-N-[2-(3,4-methylenedioxyphenoxy)ethyl]amino]propyl]-5-methyl-1,3-thiazolidin-4-one The compound obtained in Example 73 was subjected to HPLC in several tens of divided fractions under the same conditions as in Example 70 to recover the title compound. The resulting compound had the following specific rotation.

$[\alpha]_D = -28.39$ (CHCl$_3$, c=1.000)

Test Examples are described below in order to demonstrate that the compounds having formula (I) according to the present invention exhibit the three actions, i.e., an innibitory action on lipid peroxidation, a vasorelaxing action, and an inhibition of calcium overload.

Test Example 1

Inhibitory action on lipid peroxidation in vitro

Method A

A test compound was added to rabbit LDL prepared according to the method of Havel, et al. (Havel R. J. et al., *J. Clin. Invest.*, 34, 1345 (1955)), and then a soybean lipoxygenase type-IS (SLO) was added to a final concentration of 40 μg/ml. Oxidation of LDL was carried out at 37° C. in a CO$_2$ incubator for 24 hours. The oxidized LDL solution was separated by gel-permeation chromatography, and the fluorescence intensity of the LDL fraction was measured at an excitation wavelength of 360 nm and an emission wavelength of 430 nm. The results of measurement expressed as a percentage of control, are shown in Table 42.

TABLE 42

| Compound | Percent (%) of Control | |
|---|---|---|
| (Example No.) | $5 \times 10^{-6}$ M | $5 \times 10^{-7}$ M |
| None (Control) | 100 | 100 |
| Compound (9) | 5.9 | 13.5 |
| Compound (12) | 6.4 | 16.8 |
| Compound (17) | 3.9 | 16.4 |
| Compound (20) | 0.6 | 8.7 |
| Compound (41) | 6.2 | 18.3 |
| Compound (57) | 11.3 | 22.8 |
| Compound (70) | 5.1 | 15.2 |
| Compound (71) | 2.8 | 12.7 |
| Diltiazem | 110.7 | 109.1 |

Method B

A test compound was added to rabbit LDL prepared according to the method of Havel, et al. (Havel R. J., et al., *J. Clin. Invest.*, 34, 1345 (1955)), and then CuSO$_4$ was added to a final concentration of 1 μM. Oxidation of LDL was performed by shaking at 37° C. for 24 hours. The generated TBARS was measured by the method of Yagi utilizing fluorometry (Yagi, K., *Biochem. Med.*, 15, 212 (1976)). The results of measurement expressed as a percentage of control, are shown in Table 43.

TABLE 43

| Compound (Example No.) | % of Control $1 \times 10^{-5}$ M |
|---|---|
| None (Control) | 100 |
| Compound (9) | 26.4 |
| Compound (12) | 25.9 |
| Compound (17) | 21.0 |
| Compound (20) | 21.3 |
| Compound (41) | 26.3 |
| Compound (57) | 23.0 |
| Compound (70) | 21.1 |
| Compound (71) | 23.8 |
| Compound (46) | 20.4 |
| Compound (49) | 15.7 |
| Compound (34) | 20.5 |
| Compound (55) | 20.0 |
| Compound (51) | 16.6 |
| Diltiazem | 96.9 |

Test Example 2

Vasorelaxing action in vitro

Method

The thoracic aorta was excised from a Sprague-Dawley (Crj) male rat weighing between 350 and 550 g, and dissected free from surrounding connective tissue. The vessel was cut into a ring having a width of 2 to 3 mm. The resulting preparation was mounted for isometric tension recording in an organ bath filled with 10 ml of a Krebs-Henseleit solution (K-H solution, pH 7.4, 37° C.), which was bubbled with 95% O$_2$/5% CO$_2$. Isometric tension changes were monitored with an isometric tranducer (TB-611T, manufactured by Nihon Kohden Corp.). Before starting the experiment, the preparation was given a stretched tension of 2 g and allowed to equilibrate for 30 minutes (the K-H solution was exchanged for a fresh one every 15 minutes). At first, the preparation was precontracted by changing the solution in the bath to one containing 30 mM K$^+$. After the contraction was maintained for 20 minutes, the preparation was washed with K-H solution. Sixty minutes thereafter (the K-H solution was exchanged with a fresh one every 20 minutes), contraction was again induced in the same manner as described above. After the contraction stabilized, a test compound or diltiazem was added to the system in a cumulative manner in half log-unit increments to obtain a concentration-response curve.

Taking the contraction at 30 mM K$^+$ as 100%, the concentration of the drug at which the contraction is relaxed to 50% was obtained as IC$_{50}$. The results obtained are shown in Table 44.

TABLE 44

| Compound (Example No.) | Vasorelaxing Activity, IC$_{50}$ (μM) |
|---|---|
| Compound (26) | 0.037 |
| Compound (1) | 0.17 |
| Compound (8) | 0.17 |
| Compound (9) | 0.028 |
| Compound (11) | 0.021 |
| Compound (12) | 0.063 |
| Compound (17) | 0.028 |
| Compound (19) | 0.11 |
| Compound (41) | 0.056 |
| Compound (72) | 0.098 |
| Compound (73) | 0.049 |
| Compound (70) | 0.30 |
| Compound (71) | 0.027 |
| Compound (55) | 0.021 |
| Compound (49) | 0.023 |
| Compound (74) | 0.141 |
| Compound (75) | 0.022 |
| Diltiazem | 0.11 |

Test Example 3

Inhibitory action on calcium overload in vitro

Method A

Isolated ventricular myocytes were prepared from the heart of male Sprague-Dawley rat weighing 300 to 500 g, using an enzyme-perfusion method. Thus obtained rod-shaped normal myocytes were treated with a test compound or diltiazem for 30 minutes, and then 100 μg/ml of veratrine was added. Five minutes later, the shape of the cells was observed to obtain a survival rate thereby to evaluate the efficacy of the compound. The results obtained are shown in Table 45.

TABLE 45

| Compound (Example No.) | Survival Rate of Cells |
|---|---|
| Compound (26) | ++ |
| Compound (8) | ++ |
| Compound (9) | ++ |
| Compound (12) | ++ |
| Compound (20) | + |
| Diltiazem | − |

Note:
++: The cells survived almost completely at $10^{-7}$ M.
+: The cells survived almost completely at $10^{-8}$ M.
−: The cells died almost completely at $10^{-8}$ M.

Method B

The efficacy was evaluated in the same manner as in Method A, except for using 50 μg/ml of veratridine in place of veratrine (100 μg/ml). The results obtained are shown in Table 46.

TABLE 46

| Compound (Example No.) | Concentration at Which Cells Survived Almost Completely (μM) |
|---|---|
| Compound (17) | 0.32 |
| Compound (34) | 0.32 |
| Compound (70) | 0.32 |
| Compound (71) | 0.32 |
| Compound (72) | 0.32 |
| Compound (73) | 0.32 |
| Compound (74) | 0.32 |
| Compound (75) | 0.32 |
| Diltiazem | — |

Note: *: The cells died almost completely at 1 μM.

The compounds of the foregoing Examples are shown in Tables 47 through 54 below.

TABLE 47

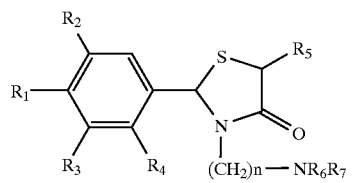

| Ex. Comp. | $R_1$ | $R_2$ | $R_3$ | $R_4$ | $R_5$ | n | —$NR_6R_7$ |
|---|---|---|---|---|---|---|---|
| 1 | OH | $^i$Pr | $^i$Pr | H | H | 3 | Me-N(Me)-CH2CH2-O-(3,4-methylenedioxyphenyl) |
| 2 | OH | H | H | H | H | 3 | " |
| 3 | OH | Me | Me | H | H | 3 | " |
| 4 | OH | Me | Me | Me | H | 3 | " |
| 5 | OH | Et | Et | H | H | 3 | " |
| 6 | OH | OMe | OMe | H | H | 3 | " |
| 7 | OH | Cl | Cl | H | H | 3 | " |
| 8 | OH | $^t$Bu | $^t$Bu | H | H | 4 | " |
| 9 | OH | $^t$Bu | $^t$Bu | H | H | 4 | " |
| 10 | OMe | Me | Me | Me | H | 3 | " |
| 11 | OMe | $^t$Bu | $^t$Bu | H | H | 3 | " |
| 12 | OH | $^t$Bu | $^t$Bu | H | H | 3 | Me-N(Et)-CH2CH2-O-(3,4-methylenedioxyphenyl) |
| 13 | OH | $^t$Bu | $^t$Bu | H | H | 3 | Me-N(iPr)-CH2CH2-O-(3,4-methylenedioxyphenyl) |
| 14 | OH | $^t$Bu | $^t$Bu | H | H | 3 | Me-N(Me)-CH2CH2-O-(4-methoxyphenyl) |

TABLE 47-continued

| Ex. Comp. | R₁ | R₂ | R₃ | R₄ | R₅ | n | —NR₆R₇ |
|---|---|---|---|---|---|---|---|
| 15 | OH | ᵗBu | ᵗBu | H | H | 3 | N,N-dimethyl-2-(3,4-dimethoxyphenoxy)ethylamine |
| 16 | OH | ᵗBu | ᵗBu | H | H | 3 | N,N-dimethyl-2-(3,4,5-trimethoxyphenoxy)ethylamine |
| 17 | OH | ᵗBu | ᵗBu | H | H | 3 | N,N-dimethyl-3-(3,4-methylenedioxyphenoxy)propylamine |

TABLE 48

| Ex. Comp. | R₁ | R₂ | R₃ | R₄ | R₅ | n | —NR₆R₇ |
|---|---|---|---|---|---|---|---|
| 18 | OH | ᵗBu | ᵗBu | H | H | 3 | N-methyl-N-[4-(benzo[1,3]dioxol-5-yloxy)butyl]amino |
| 19 | OH | ᵗBu | ᵗBu | H | H | 3 | N-methyl-N-(3,4-dimethoxybenzyl)amino |
| 20 | OH | ᵗBu | ᵗBu | H | H | 3 | N,N-dimethyl-N-[2-(3,4-dimethoxyphenyl)ethyl]amino |
| 21 | OH | ᵗBu | ᵗBu | H | H | 3 | 4-methyl-1-(2,3,4-trimethoxybenzyl)piperazinyl |
| 22 | OH | ᵗBu | ᵗBu | H | H | 3 | 4-benzyl-1-methylpiperidinyl |
| 23 | OH | ᵗBu | ᵗBu | H | H | 3 | 4-methyl-1-(diphenylmethyl)piperazinyl |
| 24 | OH | ᵗBu | ᵗBu | H | H | 3 | 2-methyl-6,7-dimethoxy-1,2,3,4-tetrahydroisoquinolinyl |

TABLE 48-continued

| Ex. Comp. | R₁ | R₂ | R₃ | R₄ | R₅ | n | —NR₆R₇ |
|---|---|---|---|---|---|---|---|
| 25 | OH | ᵗBu | ᵗBu | H | H | 3 | (1-methylpiperidin-4-yl)(benzothiazol-2-yl)methylamino |
| 26 | OH | ᵗBu | ᵗBu | H | H | 3 | N,N-dimethyl-2-(benzo[d][1,3]dioxol-5-yloxy)ethylamino |
| 27 | OH | ᵗBu | Me | H | H | 3 | " |
| 28 | OH | ᵗBu | ᵗBu | H | H | 3 | N,N-dimethyl-(benzo[d][1,3]dioxol-5-yl)methylamino |

TABLE 49

| Ex. Comp. | R₁ | R₂ | R₃ | R₄ | R₅ | n | —NR₆R₇ |
|---|---|---|---|---|---|---|---|
| 29 | H | ᵗBu | ᵗBu | H | H | 3 | N-methyl-2-(benzo[d][1,3]dioxol-5-yloxy)ethylamino |
| 30 | OAc | ᵗBu | ᵗBu | H | H | 3 | " |
| 31 | OH | ᵗBu | ᵗBu | H | H | 3 | 2-(benzo[d][1,3]dioxol-5-yloxy)ethylamino |

TABLE 49-continued
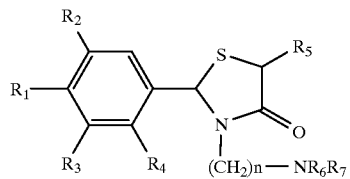
| Ex. Comp. | R₁ | R₂ | R₃ | R₄ | R₅ | n | —NR₆R₇ |
|---|---|---|---|---|---|---|---|
| 32 | OH | ᵗBu | ᵗBu | H | H | 3 | 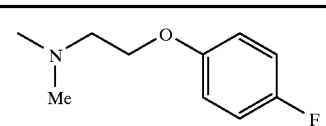 |
| 33 | OH | ᵗBu | ᵗBu | H | H | 3 | 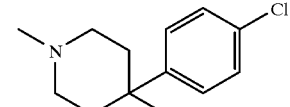 |
| 34 | OH | ᵗBu | ᵗBu | H | H | 3 | 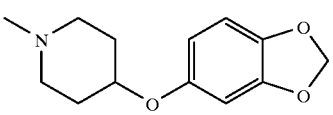 |
| 35 | OH | ᵗBu | ᵗBu | H | H | 3 | 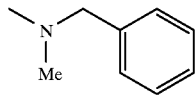 |
| 36 | OH | ᵗBu | ᵗBu | H | H | 3 | 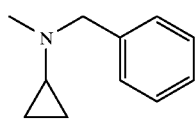 |
| 37 | OH | ᵗBu | ᵗBu | H | H | 3 | 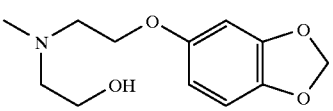 |
| 38 | OH | ᵗBu | ᵗBu | H | H | 3 | 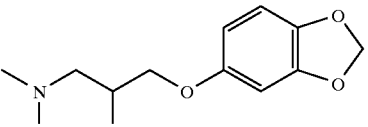 |
| 39 | OH | ᵗBu | ᵗBu | H | H | 3 | 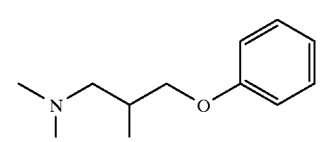 |

TABLE 49-continued
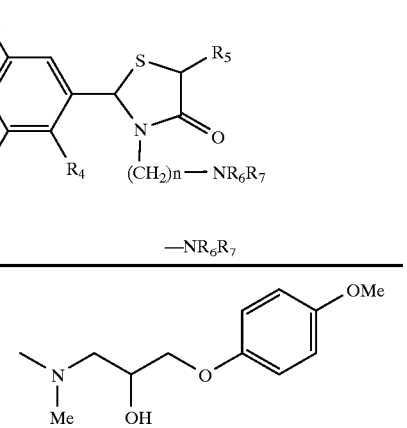
| Ex. Comp. | R₁ | R₂ | R₃ | R₄ | R₅ | n | —NR₆R₇ |
|---|---|---|---|---|---|---|---|
| 40 | OH | ᵗBu | ᵗBu | H | H | 3 | ![](structure: MeN(Me)CH₂CH(OH)CH₂O-C₆H₄-OMe) |
TABLE 50
| Ex. Comp. | R₁ | R₂ | R₃ | R₄ | R₅ | n | —NR₆R₇ |
|---|---|---|---|---|---|---|---|
| 41 | OH | ᵗBu | ᵗBu | H | Me | 3 | MeN(Me)CH₂CH₂O-(benzo[1,3]dioxol-5-yl) |
| 42 | OH | ᵗBu | ᵗBu | H | H | 2 | " |
| 43 | OH | ᵗBu | H | H | H | 3 | " |
| 44 | OH | ᵗBu | ᵗBu | H | CH₂-C₆H₅ | 3 | " |
| 45 | OH | ᵗBu | ᵗBu | H | CH₂-C₆H₄-OMe | 3 | " |
| 46 | OH | ᵗBu | ᵗBu | H | CH₂C(O)OEt | 3 | " |
| 47 | OH | ᵗBu | ᵗBu | H | CH₂C(O)OiPr | 3 | " |

TABLE 50-continued
| Ex. Comp. | R₁ | R₂ | R₃ | R₄ | R₅ | n | —NR₆R₇ |
|---|---|---|---|---|---|---|---|
| 48 | OH | ᵗBu | ᵗBu | H |  | 3 | " |
| 49 | OH | ᵗBu | ᵗBu | H | 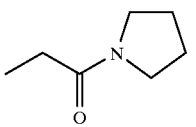 | 3 | " |
| 50 | OH | ᵗBu | ᵗBu | H | 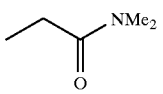 | 3 | " |
| 51 | OH | ᵗBu | ᵗBu | H | 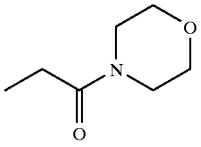 | 3 | " |
TABLE 51
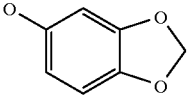
| Ex. Comp. | R₁ | R₂ | R₃ | R₄ | R₅ | n | —NR₆R₇ |
|---|---|---|---|---|---|---|---|
| 52 | OH | ᵗBu | ᵗBu | H | 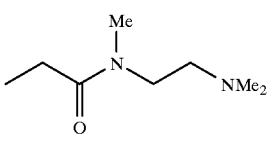 | 3 |  |
| 53 | OH | ᵗBu | ᵗBu | H |  | 3 | " |
| 54 | OH | ᵗBu | ᵗBu | H | OMe | 3 | " |

TABLE 51-continued
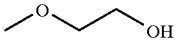
| Ex. Comp. | R₁ | R₂ | R₃ | R₄ | R₅ | n | —NR₆R₇ |
|---|---|---|---|---|---|---|---|
| 55 | OH | ᵗBu | ᵗBu | H |  | 3 | " |
| 56 | OH | ᵗBu | ᵗBu | H | 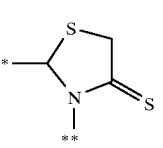 | 3 | " |
TABLE 52
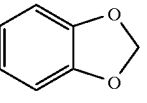
| Ex. Comp. | R₁ | R₂ | R₃ | R₄ | A | n | —NR₆R₇ |
|---|---|---|---|---|---|---|---|
| 57 | OH | ᵗBu | ᵗBu | H | 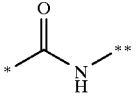 | 3 | 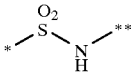 |
| 58 | OH | ᵗBu | ᵗBu | H | 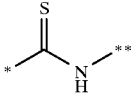 | 3 | " |
| 59 | OH | ᵗBu | ᵗBu | H | (see below) | 3 | " |
| 60 | OH | ᵗBu | ᵗBu | H | (see below) | 3 | " |

TABLE 52-continued
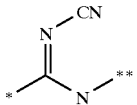
| Ex. Comp. | $R_1$ | $R_2$ | $R_3$ | $R_4$ | A | n | $-NR_6R_7$ |
|---|---|---|---|---|---|---|---|
| 61 | OH | $^tBu$ | $^tBu$ | H | ![](cyano amidine) | 3 | " |
TABLE 53
| Ex. Comp. | $R_1$ | $R_2$ | $R_3$ | $R_4$ | A | n | $-NR_6R_7$ |
|---|---|---|---|---|---|---|---|
| 62 | OH | $^tBu$ | $^tBu$ | H | oxadiazolone | 3 | N(Me)CH₂CH₂O-benzodioxole |
| 63 | OH | $^tBu$ | $^tBu$ | H | thiadiazolone | 3 | " |
| 64 | OH | $^tBu$ | $^tBu$ | H | N-Et triazolone | 3 | " |
| 65 | OH | $^tBu$ | $^tBu$ | H | oxadiazole-O | 3 | " |
| 66 | OH | $^tBu$ | $^tBu$ | H | thiadiazole S-oxide | 3 | " |

TABLE 53-continued

Structure: R1, R2, R3, R4-substituted phenyl—A—(CH2)n—NR6R7 (* on phenyl, ** on CH2)

| Ex. Comp. | R1 | R2 | R3 | R4 | A | n | —NR6R7 |
|---|---|---|---|---|---|---|---|
| 67 | OH | tBu | tBu | H | 5-imidazolyl (*-C, **-N) | 3 | " |
| 68 | OH | tBu | tBu | H | 1-oxo-thiazolidin-4-one (*-C2, **-N3) | 3 | " |
| 69 | OH | tBu | tBu | H | thiazolidine with N-acyl (*-C2, **-C(O)-) | 2 | " |

TABLE 54

Structure: R1–R4-substituted phenyl attached to 2-position of thiazolidin-4-one, with R5 at 5-position, and N-(CH2)n—NR6R7

| Ex. Comp. | R1 | R2 | R3 | R4 | R5 | n | —NR6R7 |
|---|---|---|---|---|---|---|---|
| 70 | OH | tBu | tBu | H | H | 3 | Me2N-CH2CH2-O-(benzo[1,3]dioxol-5-yl) |
| 71 | OH | tBu | tBu | H | H | 3 | " |
| 72 | OH | tBu | tBu | H | Me | 3 | " |
| 73 | OH | tBu | tBu | H | Me | 3 | " |
| 74 | OH | tBu | tBu | H | Me | 3 | " |
| 75 | OH | tBu | tBu | H | Me | 3 | " |

Test Example 4

Vasorelaxing action in vitro

Effect on $CaCl_2$

Figure 1B:
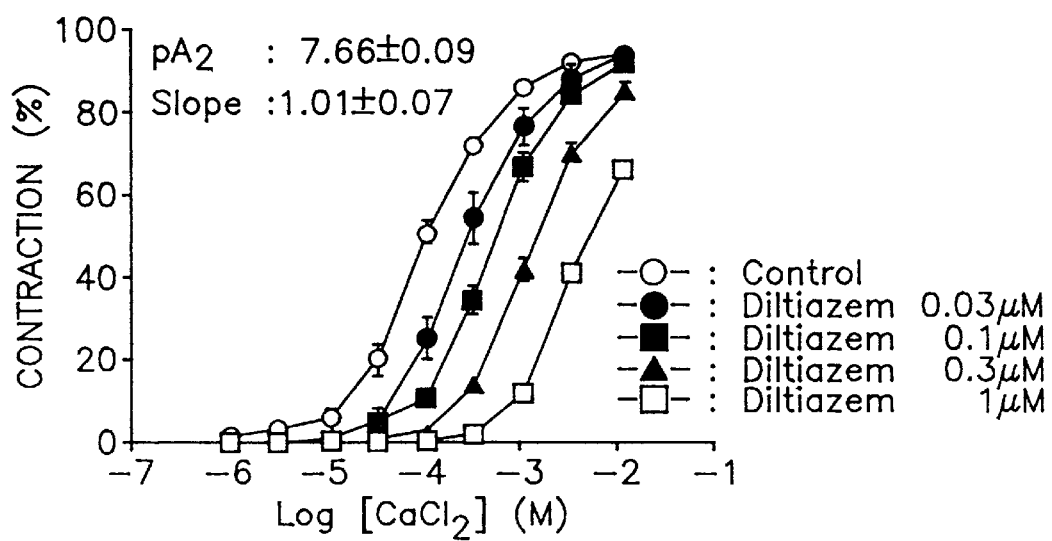

Thoracic aorta preparations from rats were stabilized In normal physiological salt solution (PSS) for at least 30 min, contracted with 60 mM KCl and, thereafter, relaxed with normal PSS. Twenty minutes later, the preparations were exposed to $Ca^{2+}$-free 60 mM $K^+$ PSS (containing 0.1 mM EGTA) for 20 min, then to nominally $Ca^{2+}$-free 60 mM $K^+$ PSS which is free of EGTA for 20 min, followed by cumulative application of $CaCl_2$ (0.01–10 mM) to construct a dose-response curve. The preparations were washed with normal PSS and left to stand for 20 min; thereafter, the preparations were treated with normal PSS containing a drug for 200 min (in the case of the compound of Example 71) or 20 min (in the case of diltiazem); thereafter, the preparations were exposed to $Ca^{2+}$-free 60 mM $K^+$ PSS which contains a drug and 0.1 mM EGTA for 20 min and to nominally $Ca^{2+}$-free 60 mM $K^+$ PSS which contains a drug for 20 min (total pretreatment time=240 min in the case of the compound of Example 71; 60 min in the case of diltiazem) to construct another dose-response curve. The response was converted to percent contraction, with the contraction caused by 10 mM $CaCl_2$ being taken as 100%. The results are shown in FIG. 1. The data in FIG. 1 are expressed by the mean of 5 cases±standard error. According to FIG. 1, the compound of the present invention need be applied in a by far smaller amount than diltiazem to exhibit an outstanding inhibitory action against the contraction caused by $CaCl_2$.

Test Example 5

Antispasmodic action in vitro

Figure 2:
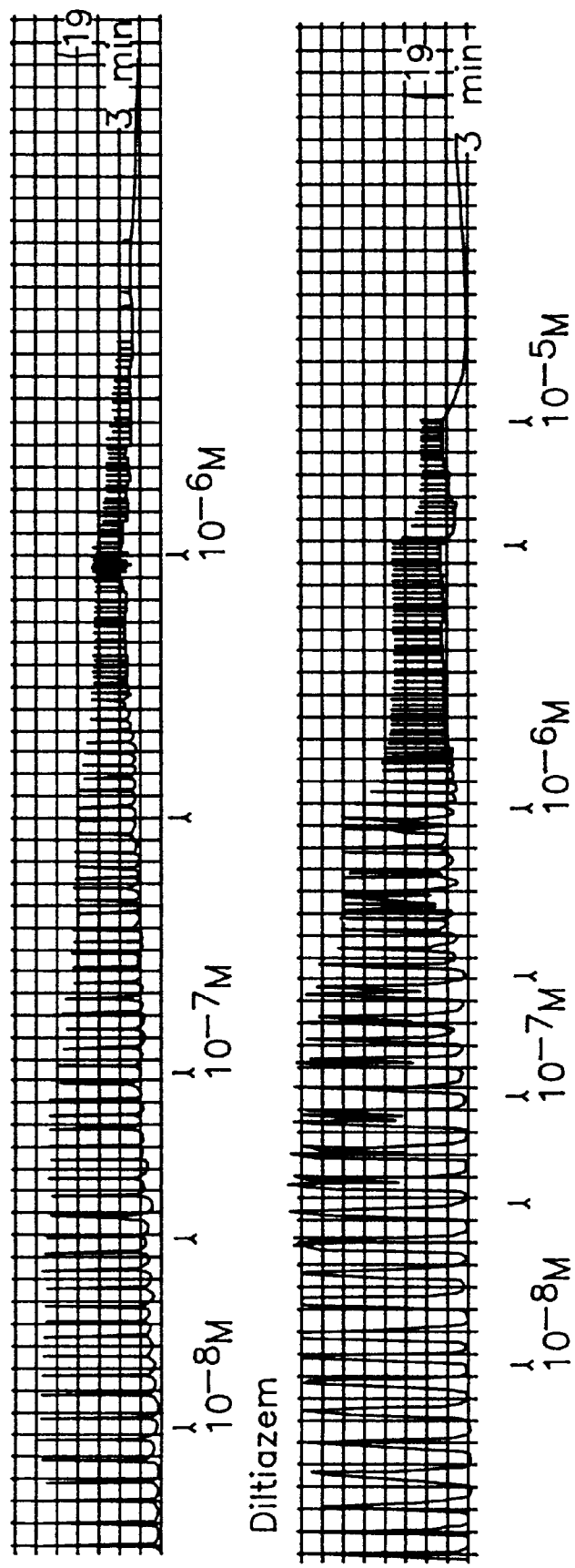
FIG. 2 is a set of charts which illustrate the actions of the compound of Example 71 and diltiazem on 3,4-diaminopyridine-induced rhythmic contractions in isolated dog coronary arteries.

Effect on rhythmic contractions induced by 3,4-diaminopyridine (hereunder abbreviated as 3,4-DAP) in coronary preparations from dogs Following repeated replacements of PSS in an organ bath at 15-min intervals, the tension on each of the coronary preparations from dogs stabilized at 2 g; then, PSS was replaced by a 30 mM $K^+$ PSS to contract the preparations. The 30 mM $K^+$ PSS was replaced by normal PSS in an organ bath to relax the preparations, followed by replacements with PSS at 20-min intervals to stabilize the tension for about 1 h, followed by the addition of 3,4-DAP (10 mM) to induce rhythmic contractions. When the appearance of the rhythmic contraction stabilized, the compound of Example 71 or diltiazem was added to the organ bath in a cumulative manner in half log-unit increments. The drug concentration allowing for complete suppression of the amplitude of the 3,4-DAP-induced rhythmic contractions may be designated "elimination dose". The results are shown in FIG. 2, according to which one can see that the compound of the present invention is capable of suppressing the 3,4-DAP-induced rhythmic contractions at a lower concentration than diltiazem.

Test Example 6

Action on the cardiovascular system

Effect on coronary blood flow

Male beagles (9–10 kg) were anesthetized by intravenous administration of sodium pentobarbital (35 mg/kg). After tracheotomy, the dogs were artificially ventilated (16–18 times per minute; 22 ml/kg) with room air by an respirator (Harvard Model 607). Blood pressure was measured by means of a cannula inserted into the right femoral artery attached to a pressure transducer (TP-200TL of Nihon Kohden Corp.). Heart rate was measured using a cardiotachometer (AT-610G of Nihon Kohden Corp.) tiggered by the femoral artery pressure pulse. Sodium pentobarbital for maintenance of anesthesia (3–5 mg/kg/h) was infused through a forefoot venous cannula. A microtip catheter (SPC-350 of Miller) was inserted into the left ventricle through the left femoral artery to measure left ventricle pressure. Maximal first derivative of left ventricle pressure (max. LVdP/dt) was calculated with a differentiator (EQ-601G of Nihon Koden Corp.). Each dog was incised between the fourth and fifth ribs on the left side and had the phrenic nerve cut off; thereafter, the pericardium was incised and fixed to the chest to expose the heart. A portion of the left coronary artery which was several centimeters distant from the beginning of the ramus circumflexus was peeled by about one centimeter and after attaching a probe for the measurement of blood flow, the quantity of coronary blood flow was measured with an electromagnetic instrument (MFV-2100 of Nihon Kohden Corp.). The data of coronary blood flow and mean blood pressure were processed with an operational amplifier (EO-601G of Nihon Kohden Corp.) to calculate the resistance of coronary blood vessel. Blood gas pressures ($pO_2$ and $pCO_2$) and the pH of blood were measured as required (ABL-520 of Radiometer) to confirm that they were within physiological ranges. Throughout the experiment, a heat insulating mat and illumination were employed to prevent the body temperature of the animals from dropping.

Following a recuperation period of about 60 min after the surgical operation, the compound of Example 71 (10–300 μg/kg) or diltiazem (10–300 μg/kg) was administered intravenously in progressively increasing amounts through a cannula inserted into the forefoot vein; such that the next dose of each drug was administered when all parameters reverted to the initial levels.

The compound of Example 71 was formulated as a drug solution by first dissolving it in DMSO and subsequently diluting the solution with distilled water for injection that had been made acidic with hydrochloric acid (1% DMSO, $10^{-3}$M HCl, pH≅5).

Diltiazem (Sigma) was dissolved in physiological saline.

The results are all represented in terms of the mean of four cases±standard error and shown in FIG. 3, in which MBP represents mean blood pressure, HR heart rate, CBF coronary blood flow, CVR coronary vessel resistance, and max. LVdp/dt maximal first derivative of left ventride pressure. As can be seen from FIG. 3, the compound of the invention exhibits an outstanding action in increasing the coronary blood flow.

Test Example 7

Action on the cardiovascular system

Preventive effect on the occurrence of ventricular arrhythmia caused by the occlusion and reperfusion of the coronary artery in the heart of rats Male Sprague-Dawley rats (450–600 g) were anethetized with pentobarbital, subjected to thoracotomy under artificial respiration, had the arterior descending branch of the left coronary artery occluded with a silk ligature for 5 min, had the occlusion removed to permit reperfusion and examined for 10 min. A standard limb lead II electrocardiogram was recorded to check for the occurrence of ventricular arrythmia. The drug (compound of Example 26 or diltiazem) was administered through an indwelling catheter in the femoral vein as an aqueous solution 10 min before the occlusion of the coronary artery; the compound of Example 26 was varied in dose at 0.5, 1 and 3 mg/kg whereas diltiazem varied at 1 and 3 mg/kg. The results are shown in FIG. 4. The parethesized numeral at the bottom of each bar in FIG. 4 represents the number of cases. As can be seen from FIG. 4, the compound of the present invention exhibits a by far superior effect to diltiazem in decreasing the incidnece of arrhythmia.

Example 76

Preparation of 2-(3,5-di-tert-butyl-4-hydroxyphenyl)-3-[3-[N-methyl-N-[3-(2-benzimidazolyl)propyl]amino]propyl]-1,3-thiazolidin-4-one The title compound was obtained according to the procedure for Example 26-A, using N-methyl-N-[3-(2-benzimidazolyl)propyl]amine instead of N-methyl-N-[2-(3, 4-methylenedioxyphenoxy)ethyl]amine. NMR (CDCl$_3$) (200 MHz) δ: 1.40 (18H, s), 1.4–1.8 (2H, m), 1.8–2.2 (2H, m), 2.22 (3H, s), 2.3–2.7 (4H, m), 2.7–3.2 (3H, m), 3.5–4.3 (4H, m), 5.57 (1H, s), 7.07 (2H, s), 7.1–7.4 (2H, m), 7.24(1H, s), 7.4–7.7 (2H, m)

Examples 77 to 78

Each compound shown in Table 55 was prepared according to the procedure for Example 26-B, using an appropriate bromide in each case.

obtained in Reference Example 33 and 3-(3-chloropropyl)-1,3-thiazolidin-4-one (0.19 g) in DMF (5 ml) were added potassium carbonate (0.44 g) and sodium iodide (0.79 g) under a nitrogen atmosphere, the mixture was stirred at 60° C. for 3 days. After cooling, the mixture was poured into ice-water, and the product was extracted with ethyl acetate. The extract was washed with water then brine. The organic layer was dried over anhydrous sodium sulfate, and evaporated under reduced pressure. The residue was purified by silica gel column chromatography (eluent; chloroform-methanol, 98:2) to afford 0.32 g (59%) of the title compound as a brown oil. NMR (CDCl$_3$) (200 MHz) δ: 1.43(18H, s), 1.5–2.0 (4H, m), 2.06 (3H, s), 2.1–2.4 (4H, m), 2.6–3.0 (1H, m), 3.31 (2H, t, J=7.1 Hz), 3.4–3.7 (1H, m), 3.53 (2H, s), 3.64 and 3.79 (2H, ABq, J=16 Hz), 4.36 (2H, s), 5.32(1H, s), 5.56(1H, s), 7.07 (2H, s)

Examples 80 to 84

Each compound shown in Table 56 was prepared according to the procedure for Example 79, using an appropriate chloride in each case.

TABLE 55

| Ex. No. | R$^1$ | R$^2$ | Physical Properties ($^1$H-NMR (CDCl$_3$)) |
|---|---|---|---|
| 77 | 3,5-di-tert-butyl-4-hydroxyphenyl with N-Me linker | 4-hydroxyphenyl | 1.41(18H, s), 1.4–1.8(2H, m), 2.20(3H, s), 2.2–2.9(7H, m), 3.4–3.7(1H, m), 3.68 and 3.80 (2H, ABq, J=16Hz), 5.32(1H, s), 5.59(1H, s), 6.70(2H, d, J=8.6Hz), 6.95 (2H, d, J=8.6Hz), 7.08(2H, s), 7.26(1H, s) |
| 78 | 3,5-di-tert-butyl-4-hydroxyphenyl with N-Me linker | 2,2-dimethyl-2,3-dihydrobenzofuran-7-yloxy | 1.1–1.8(2H, m), 1.43(18H, s), 1.47(6H, s), 2.20(3H, s), 2.2–2.6(2H, m), 2.70(2H, t, J=6.3Hz), 2.7–3.0(1H, m), 3.00(2H, s), 3.4–3.7(1H, m), 3.64 and 3.79 (2H, ABq, J=16Hz), 4.07(2H, t, J=6.3Hz), 5.31(1H, s), 5.60(1H, s), 6.6–6.9(3H, m), 7.09(2H, s) |

Example 79

Preparation of 2-(3,5-di-tert-butyl-4-hydroxyphenyl)-3-[3-[N-methyl-N-[3-(4-oxo-1,3-thiazolidin-3-yl)propyl]amino]propyl]-1,3-thiazolidin-4-one To a solution of 2-(3,5-di-tert-butyl-4-hydroxyphenyl)-3-[3-(N-methylamino)propyl]-1,3-thiazolidin-4-one (0.40 g)

TABLE 56

Structure: 2-R¹-3-(3-R²-propyl)-1,3-thiazolidin-4-one

| Ex. No. | R¹ | R² | Physcial Properties (¹H-NMR (CDCl₃)) |
|---|---|---|---|
| 80 | 3,5-di-tert-butyl-4-hydroxyphenyl | —N(Me)—CH₂CH₂CH₂—S—(2-methoxyphenyl) | 1.42(18H, s), 1.4–1.8(4H, m), 2.05(3H, s), 2.1–2.3(2H, m), 2.38 (2H, t, J=7.3Hz), 2.7–2.9(1H, m), 2.86(2H, t, J=7.3Hz), 3.4–3.6(1H, m), 3.66 and 3.78(2H, ABq, J=16Hz), 3.88(3H, s), 5.31(1H, s), 5.59(1H, s), 6.8–7.0(2H, m), 7.09 (2H, s), 7.1–7.3(2H, m) |
| 81 | 3,5-di-tert-butyl-4-hydroxyphenyl | —N(Me)—CH₂—C(=O)—NH—(3,4-methylenedioxyphenyl) | 1.42(18H, s), 1.4–1.7(2H, m), 2.24 (3H, s), 2.41(2H, t, J=6.3Hz), 2.8–3.0(1H, m), 2.98 and 3.05(2H, ABq, J=16Hz), 3.68 and 3.82(2H, ABq, J=16Hz), 3.7–3.9(1H, m), 5.34 (1H, s), 5.56(1H, s), 5.93(2H, s), 6.75(1H, d, J=8.3Hz), 6.99(1H, d, J=8.3Hz), 7.09(2H, s), 7.40(1H, s) 9.24(1H, brs) |
| 82 | 3,5-di-tert-butyl-4-hydroxyphenyl | —N(Me)—CH₂CH₂CH₂—N(2,4-dioxothiazolidin-3-yl) | 1.41(18H, s), 1.5–1.9(4H, m), 2.03 (3H, s), 2.1–2.5(4H, m), 2.6–3.0 (1H, m), 3.4–3.8(1H, m), 3.61(2H, t, J=7.1Hz), 3.64 and 3.78(2H, ABq, J=16Hz), 3.90(2H, s), 5.32 (1H, s), 5.57(1H, s), 7.07(2H, s) |
| 83 | 3,5-di-tert-butyl-4-hydroxyphenyl | —N(Me)—CH₂—C(=O)—NH—CH₂—(3,4-methylenedioxyphenyl) | 1.1–1.8(2H, m), 1.43(18H, s), 2.14 (3H, s), 2.33(2H, t, J=6.3Hz), 2.6–2.9(1H, m), 2.94(2H, s), 3.4–3.7 (1H, m), 3.63 and 3.77(2H, ABq, J=16Hz), 4.34(2H, d, J=5.7Hz), 5.34 (1H, s), 5.49(1H, s), 5.91(2H, s), 6.6–6.9(3H, m), 7.06(2H, s), 7.4–7.8(1H, m) |
| 84 | 3,5-di-tert-butyl-4-hydroxyphenyl | —N(Me)—CH₂CH₂—N(imidazolyl substituted with 3,4-methylenedioxyphenyl) | 1.1–1.8(2H, m), 1.41(18H, s), 1.98 (3H, s), 2.19(2H, t, J=7.1Hz), 2.44 (2H, t, J=7.1Hz), 2.6–3.0(1H, m), 3.2–3.6(1H, m), 3.65 and 3.79 (2H, ABq, J=16Hz), 3.91(2H, t, J=7.1Hz), 5.52(1H, s), 6.00(2H, s), 6.6–6.9(3H, m), 7.09(2H, s), 7.26 (1H, s), 7.49(1H, s) |

Reference Example 63

Preparation of 2-(3,5-di-tert-butyl-4-hydroxyphenyl)-3-[3-[N-methyl-N-(2 3-epoxypropyl)amino]propyl]-1,3-thiazolidin-4-one To a solution of 2-(3,5-di-tert-butyl-4-hydroxyphenyl)-3-[3-(N-methylamino)propyl]-1,3-thiazolidin-4-one (0.90 g) obtained in Reference Example 33 and epibromohydrin (0.36 g) in acetone (5 ml) was added potassium carbonate (0.66 g), and the mixture was stirred at room temperature for 15 hours.

The reaction mixture was poured into ice-water (50 ml), and the product was extracted with ethyl acetate. After washing with brine, the extract was dried over anhydrous sodium sulfate and evaporated under reduced pressure. The residue was purified by silica gel column chromatography (eluent; chloroform-methanol, 98:2) to afford 0.53 g (51%) of the title compound as a yellow oil. NMR (CDCl₃) (200 MHz) δ: 1.43 (18H, s), 1.2–1.9 (2H, m), 2.20 (3H, s), 2.1–2.5 (4H, m), 2.5–3.2 (4H, m), 3.4–3.7(1H, m), 3.66 and 3.79 (2H, ABq J=16 Hz), 5.28 (1H, brs), 5.60(1H, s), 7.09 (2H, s)

Example 85

Preparation of 2-(3,5-di-tert-butyl-4-hydroxyphenyl)-3-[3-[N-methyl-N-[2-hydroxy-3-(2-methoxyphenylthio)propyl]amino]propyl]-1,3-thiazolidin-4-one To a solution of 2-(3,5-di-tert-butyl-4-hydroxyphenyl)-3-[3-[N-methyl-N-(2,3-epoxypropyl)amino]propyl]-1,3-thiazolidin-4-one (0.50 g) obtained in Reference Example 63 in ethanol (10 ml) was added 2-methoxythiophenol (0.64 g), and the mixture was stirred at room temperature for 15 hours. The reaction mixture was poured into 5% aqueous sodium hydroxide (100 ml), and the product was extracted with diethyl ether. After washing with brine, the extract was dried over anhydrous sodium sulfate and evaporated under reduced pressure. The residue was purified by silica gel column chromatography (eluent; chloroform-methanol, 98:2) to afford 0.64 g (97%) of the title compound as a colorless oil. NMR (CDCl$_3$) (200 MHz) δ: 1.0–1.8 (2H, m), 1.43 (18H, s), 2.10 (3H, s), 2.1–2.6 (4H, m), 2.6–3.2 (3H, m), 3.3–3.9(3H, m), 3.66 and 3.79 (2H, ABq J=16 Hz), 3.89 (3H, s), 5.31(1H, s), 5.53 (1H, s), 6.7–7.0 (2H, m), 7.06 (2H, s), 7.1–7.5 (2H, m)

The names of the compounds prepared in Examples 76 to 85 are as follows:

Example 76

2-(3,5-di-tert-butyl-4-hydroxyphenyl)-3-[3-[N-methyl-N-[3-(2-benzimidazolyl)propyl]amino]propyl]-1,3-thiazolidin-4-one.

Example 77

2-(3,5-di-tert-butyl-4-hydroxyphenyl)-3-[3-[N-methyl-N-[2-(4-hydroxyphenyl)ethyl]amino]propyl]-1,3-thiazolidin-4-one.

Example 78

2-(3,5-di-tert-butyl-4-hydroxyphenyl)-3-[3-[N-methyl-N-[2-(2,3-dihydro-2,2-dimethylbenzofuran-7-yl)oxyethyl]amino]propyl]-1,3-thiazolidin-4-one.

Example 79

2-(3,5-di-tert-butyl-4-hydroxyphenyl)-3-[3-[N-methyl-N-[3-(4-oxo-1,3-thiazolidin-3-yl)propyl]amino]propyl]-1,3-thiazolidin-4-one.

Example 80

2-(3,5-di-tert-butyl-4-hydroxyphenyl)-3-[3-[N-methyl-N-[3-(2-methoxyphenylthio)propyl]amino]propyl]-1,3-thiazolidin-4-one.

Example 81

2-(3,5-di-tert-butyl-4-hydroxyphenyl)-3-[3-[N-methyl-N[(3,4-methylenedioxyphenyl)aminocarbonylmethyl]-amino]propyl]-1,3-thiazolidin-4-one.

Example 82

2-(3,5-di-tert-butyl-4-hydroxyphenyl)-3-[3-[N-methyl-N-[3-(2,4-dioxo-1,3-thiazolidin-3-yl)propyl]amino]-propyl]-1,3-thiazolidin-4-one.

Example 83

2-(3,5-di-tert-butyl-4-hydroxyphenyl)-3-[3-[N-methyl-N[(3,4-methylenedioxyphenylmethyl)aminocarbonylmethyl] amino2propyl]-1,3-thiazolidin-4-one.

Example 84

2-(3,5-di-tert-butyl-4-hydroxyphenyl)-3-[3-[N-methyl-N-[2-[5-(3,4-methylenedioxyphenyl)-1H-imidazol-1-yl] ethyl]amino]propyl]-1,3-thiazolidin-4-one.

Example 85

2-(3,5-di-tert-butyl-4-hydroxyphenyl)-3-[3-[N-methyl-N-[2-hydroxy-3-(2-methoxyphenylthio)propyl]amino] propyl]-1,3-thiazolidin-4-one.

The compounds of Examples 76 to 85 are shown in Table 57.

TABLE 57

| Ex. Comp. | R$_1$ | R$_2$ | R$_3$ | R$_4$ | R$_5$ | n | —NR$_6$R$_7$ |
|---|---|---|---|---|---|---|---|
| 76 | OH | $^t$Bu | $^t$Bu | H | H | 3 | |
| 77 | OH | $^t$Bu | $^t$Bu | H | H | 3 | |

TABLE 57-continued
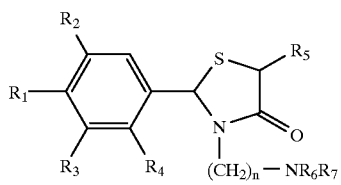
| Ex. Comp. | R₁ | R₂ | R₃ | R₄ | R₅ | n | —NR₆R₇ |
|---|---|---|---|---|---|---|---|
| 78 | OH | ᵗBu | ᵗBu | H | H | 3 | 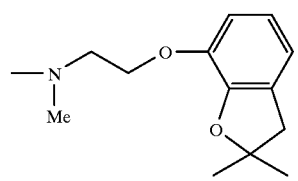 |
| 79 | OH | ᵗBu | ᵗBu | H | H | 3 | 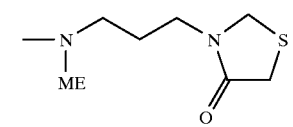 |
| 80 | OH | ᵗBu | ᵗBu | H | H | 3 | 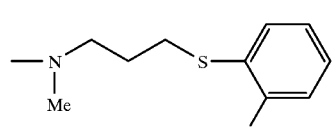 |
| 81 | OH | ᵗBu | ᵗBu | H | H | 3 | 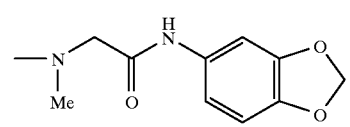 |
| 82 | OH | ᵗBu | ᵗBu | H | H | 3 | 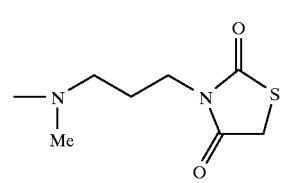 |
| 83 | OH | ᵗBu | ᵗBu | H | H | 3 | 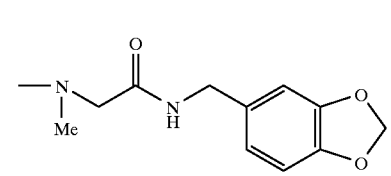 |
| 84 | OH | ᵗBu | ᵗBu | H | H | 3 | 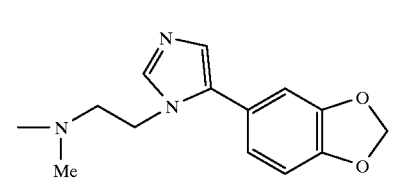 |

TABLE 57-continued

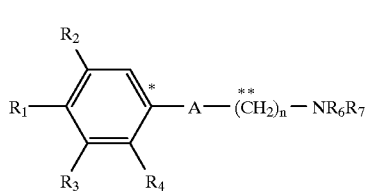

| Ex. Comp. | R₁ | R₂ | R₃ | R₄ | R₅ | n | —NR₆R₇ |
|---|---|---|---|---|---|---|---|
| 85 | OH | ᵗBu | ᵗBu | H | H | 3 | 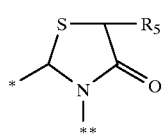 |

Industrial Applicability

As has been described, the compound according to the present invention concurrently exhibits an inhibitory action on lipid peroxidation, a vasorelaxing action, and an inhibitory action on calcium overload and could therefore be used as a preventive or therapeutic agent for ischemic diseases and an antihypertensive agent.

What is claimed is:

1. A compound represented by formula (I):

(I)

$$R_1 \cdots R_2 \cdots R_3 \cdots R_4 \text{—A—(CH}_2)_n\text{—NR}_6R_7$$

wherein $R_1$ represents a hydrogen atom, a hydroxyl group, an acyloxy group having 1 to 9 carbon atoms or a lower alkoxy group having 1 to 6 carbon atoms;

$R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms;

$R_4$ represents a hydrogen atom, a lower alkyl group having 1 to 6 carbon atoms; A represents a fragment represented by formula (II):

(II)

[structure]

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B         (III)

wherein B represents a fragment selected from the following group of fragments represented by formulae (IV), (V), (VI), (VII), (VIII), (X), (XI), (XII), (XIII), (XIV), (XV), and (XVI):

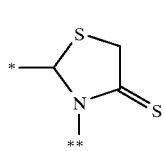 (IV)

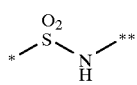 (V)

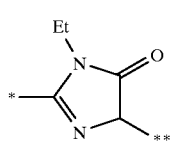 (VI)

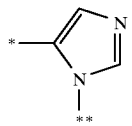 (VII)

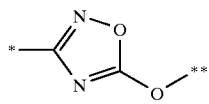 (VIII)

-continued

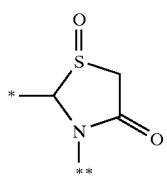
(X)

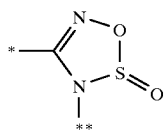
(XI)

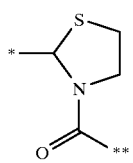
(XII)

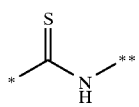
(XIII)

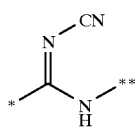
(XIV)

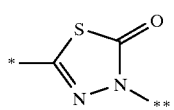
(XV)

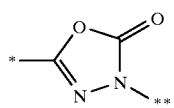
(XVI)

$R_6$ and $R_7$, which may be the same or different, each represents a hydrogen atom, a substituted or unsubstituted lower alkyl group having 1 to 6 carbon atoms, an unsubstituted lower alkenyl group having 1 to 6 carbon atoms, a substituted or unsubstituted aryl group or an unsubstituted heterocyclic ring, provided that $R_6$ and $R_7$ do not both represent a methyl group or $R_6$ and $R_7$ are taken together to form a substituted or unsubstituted ring which may be a condensed ring; and n represents an integer of 2, 3, 4, 5 or 6, or a stereoisomer or optical isomer thereof and a pharmaceutically acceptable salt thereof with the proviso that said compound is not 1,2-Bis(2-phenylthiazolidin-4-on-3-yl)ethane.

2. A compound represented by formula (I):

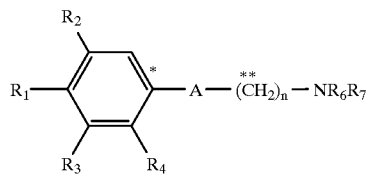
(I)

wherein $R_1$ represents a hydroxyl group, an acyloxy group having 1 to 9 carbon atoms or a lower alkoxy group having 1 to 6 carbon atoms;

$R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms;

$R_4$ represents a hydrogen atom, a lower alkyl group having 1 to 6 carbon atoms; A represents a fragment represented by formula (II):

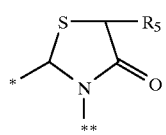
(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B   (III)

wherein B represents a fragment selected from the following group of fragments represented by formulae (IV), (V), (VI), (VII), (VIII), (X), (XI), (XII), (XIII), (XIV), (XV), and (XVI):

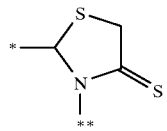
(IV)

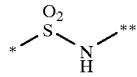
(V)

-continued

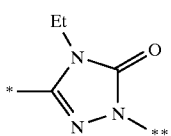
(VI)

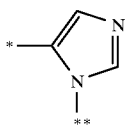
(VII)

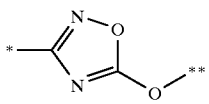
(VIII)

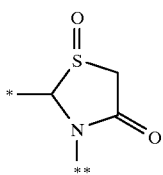
(X)

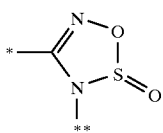
(XI)

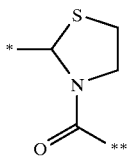
(XII)

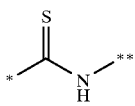
(XIII)

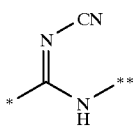
(XIV)

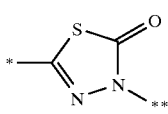
(XV)

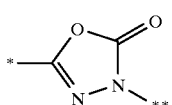
(XVI)

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl ring or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4, 5 or 6, or a stereoisomer or optical isomer thereof and a pharmaceutically acceptable salt thereof.

3. A compound according to claim 1, which is represented by formula (I):

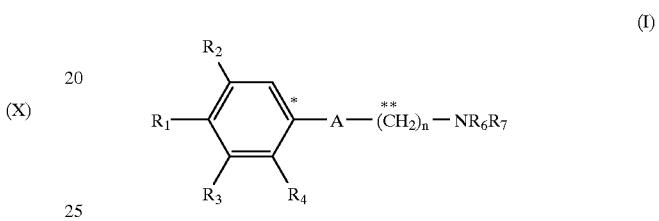
(I)

wherein $R_1$ represents a hydroxyl group, an acyloxy group having 1 to 9 carbon atoms or a lower alkoxy group having 1 to 6 carbon atoms;

$R_2$ and $R_3$, which may be the same or different, each represents a hydrogen atom or a lower alkyl group having 1 to 4 carbon atoms; $R_4$ represents a hydrogen atom or a methyl group; and A represents a fragment represented by formula (II):

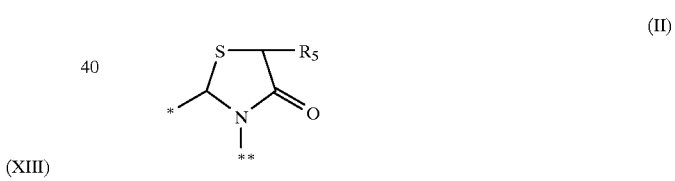
(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B       (III)

wherein B represents a fragment selected from the following group of fragments represented by formulae (IV), (V), (VI), (VII), and (VIII):

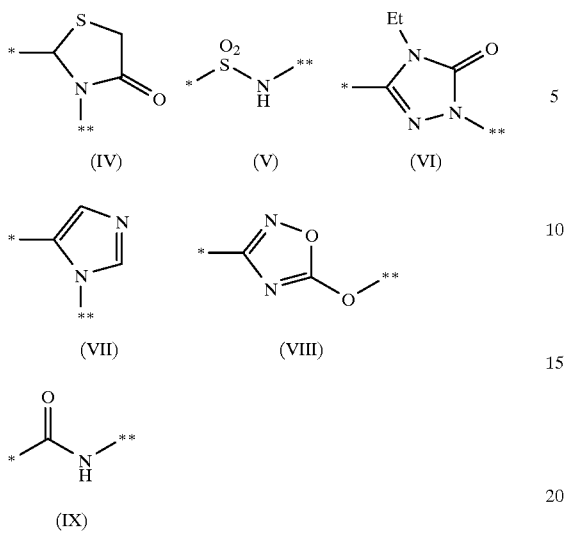

(IV)  (V)  (VI)

(VII)  (VIII)

(IX)

R₆ and R₇, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic ring, provided that R₆ and R₇ do not both represent a methyl group or R₆ and R₇ are taken together to form a substituted or unsubstituted ring which may be a condensed ring; and n represents an integer of 2, 3, 4 or 5, or a stereoisomer or optical isomer thereof and a pharmaceutically acceptable salt thereof.

4. A compound according to claim 1, which is represented by formula (I):

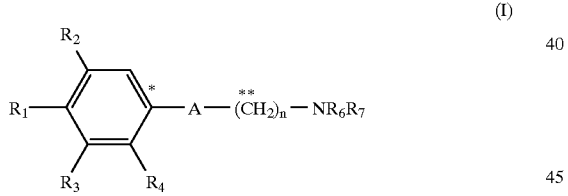

(I)

wherein R₁ represents a hydroxyl group, an acyloxy group having 1 to 9 carbon atoms or a lower alkoxy group having 1 to 6 carbon atoms;

R₂ and R₃, which may be the same or different, each represents a methyl group, an ethyl group, an isopropyl group or a t-butyl group;

R₄ represents a hydrogen atom or a methyl group; A represents a fragment represented by formula (II):

(II)

wherein R₅ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B  (III)

wherein B represents a fragment represented by formula (IV):

(IV)

R₆ and R₇, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that R₆ and R₇ do not both represent a methyl group or R₆ and R₇ are taken together to form a substituted or unsubstituted ring which may be a condensed ring; and n represents an integer of 2, 3, 4 or 5, or a stereoisomer or optical isomer thereof and a pharmaceutically acceptable salt thereof.

5. A compound according to claim 1, which is represented by formula (I):

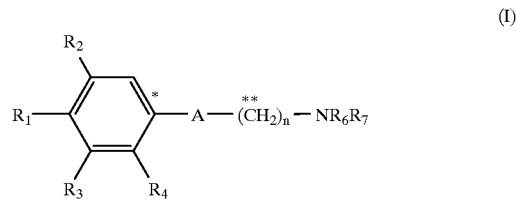

(I)

wherein R₁ represents a hydroxyl group, an acyloxy group having 1 to 9 carbon atoms or a lower alkoxy group having 1 to 6 carbon atoms;

R₂ represents a t-butyl group;
R₃ represents a t-butyl group;
R₄ represents a hydrogen atom; and
A represents a fragment represented by formula (II):

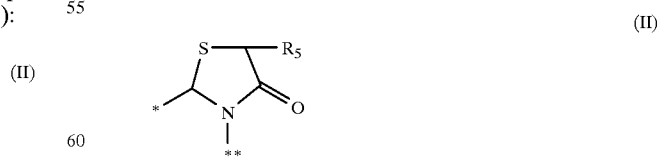

(II)

wherein R₅ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

6. A compound according to claim 1, which is represented by formula (I):

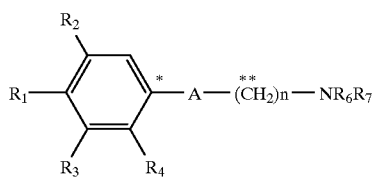

wherein $R_1$ represents a hydroxyl group or a methoxy group;

$R_2$ represents a t-butyl group;

$R_3$ represents a t-butyl group;

$R_4$ represents a hydrogen atom; and

A represents a fragment represented by formula (II):

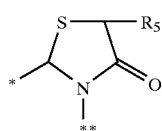

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

7. A compound according to claim 1, which is represented by formula (I):

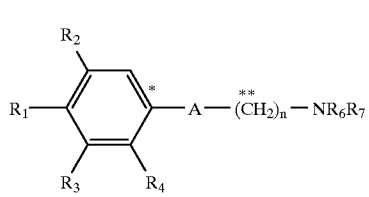

wherein $R_1$ represents a hydroxyl group;

$R_2$ represents a t-butyl group;

$R_3$ represents a t-butyl group;

$R_4$ represents a hydrogen atom; and

A represents a fragment represented by formula (II):

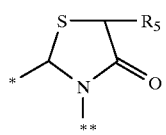

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

8. A compound according to claim 1, which is represented by formula (I):

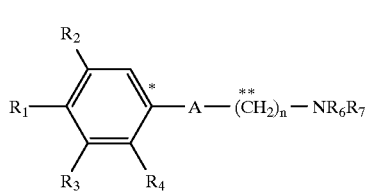

wherein $R_1$ represents a hydroxyl group;

$R_2$ represents a t-butyl group;

$R_3$ represents a t-butyl group;

$R_4$ represents a hydrogen atom; and

A represents a fragment represented by formula (II):

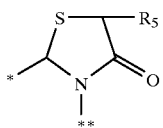
(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 3, or a stereoisomer or optical isomer thereof and a pharmaceutically acceptable salt thereof.

9. A compound according to claim 1, which is represented by formula (I):

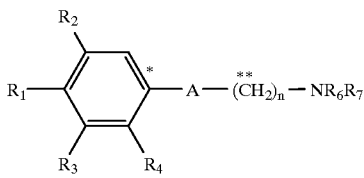
(I)

wherein $R_1$ represents an acyloxy group having 1 to 9 carbon atoms;
$R_2$ represents a t-butyl group;
$R_3$ represents a t-butyl group;
$R_4$ represents a hydrogen atom; and
A represents a fragment represented by formula (II):

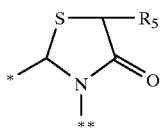
(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

10. A compound according to claim 1, which is represented by formula (I):

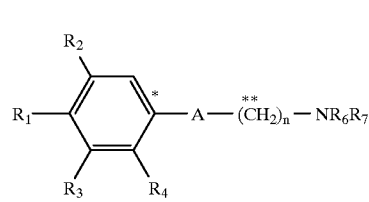
(I)

wherein $R_1$ represents a lower alkoxy group having 1 to 6 carbon atoms;
$R_2$ represents a t-butyl group;
$R_3$ represents a t-butyl group;
$R_4$ represents a hydrogen atom; and
A represents a fragment represented by formula (II):

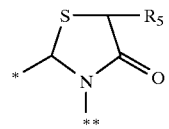
(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

11. A compound according to claim 1, which is represented by formula (I):

117

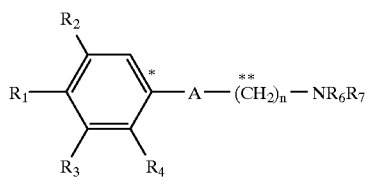
(I)

wherein R$_1$ represents a methoxy group;
R$_2$ represents a t-butyl group;
R$_3$ represents a t-butyl group;
R$_4$ represents a hydrogen atom; and
A represents a fragment represented by formula (II):

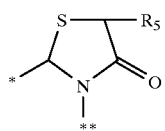
(II)

wherein R$_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted lower alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom;

R$_6$ and R$_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or an unsubstituted heterocyclic group, provided that R$_6$ and R$_7$ do not both represent a methyl group or R$_6$ and R$_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

12. A compound according to claim 1, which is represented by formula (I):

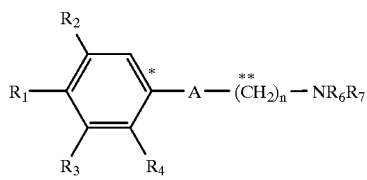
(I)

wherein R$_1$ represents a hydroxyl group, an acyloxy group having 1 to 9 carbon atoms or a lower alkoxy group having 1 to 6 carbon atoms;
R$_2$ represents a t-butyl group;
R$_3$ represents a t-butyl group;
R$_4$ represents a hydrogen atom; and

118

A represents a fragment represented by formula (II):

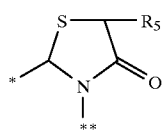
(II)

wherein R$_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom; R$_6$ and R$_7$, which may be the same or different, each represents a hydrogen atom or a substituted or unsubstituted lower alkyl group having 1 to 6 carbon atoms, provided that R$_6$ and R$_7$ do not both represent a methyl group or R$_6$ and R$_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

13. A compound according to claim 1, which is represented by formula (I):

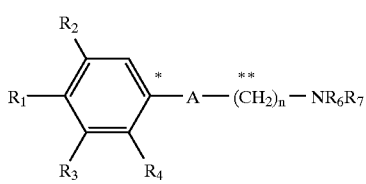
(I)

wherein R$_1$ represents a hydroxyl group, an acyloxy group having 1 to 9 carbon atoms or a lower alkoxy group having 1 to 6 carbon atoms;
R$_2$ represents a t-butyl group;
R$_3$ represents a t-butyl group;
R$_4$ represents a hydrogen atom; and
A represents a fragment represented by formula (II):

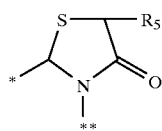
(II)

wherein R$_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;
R$_6$ and R$_7$, which may be the same or different, each represents a hydrogen atom or a substituted or unsubstituted lower alkyl group having 1 to 6 carbon atoms, provided that R$_6$ and R$_7$ do not both represent a methyl group or $R_6$ and $R_7$ are taken together to form a substituted or unsubstituted ring which may be a condensed ring; and n represents an integer of 3, or a stereoisomer or optical isomer thereof and a pharmaceutically acceptable salt thereof.

14. A compound according to claim 1, which is represented by formula (I):

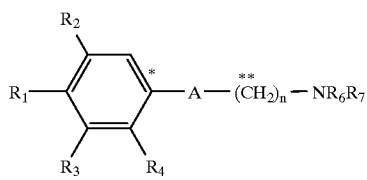
(I)

wherein $R_1$ represents a hydroxyl group, an acyloxy group having 1 to 9 carbon atoms or a lower alkoxy group having 1 to 6 carbon atoms;

$R_2$ represents a t-butyl group;

$R_3$ represents a t-butyl group;

$R_4$ represents a hydrogen atom; and

A represents a fragment represented by formula (II):

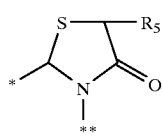
(II)

wherein $R_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

$R_6$ and $R_7$, which may be the same or different, each represents a substituted or unsubstituted lower alkyl group having 1 to 6 carbon atoms, provided that $R_6$ and $R_7$ do not both represent a methyl group or $R_6$ and $R_7$ are taken together to form a substituted or unsubstituted ring which may be a condensed ring; and n represents an integer of 2, 3, 4 or 5, or a stereoisomer or optical isomer thereof and a pharmaceutically acceptable salt thereof.

15. A compound according to claim 1, which is represented by formula (I):

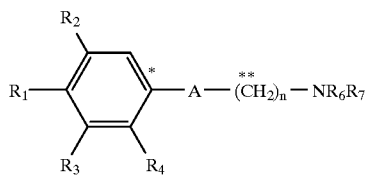
(I)

wherein $R_1$ represents a hydroxyl group, an acyloxy group having 1 to 9 carbon atoms or a lower alkoxy group having 1 to 6 carbon atoms;

$R_2$ represents a t-butyl group;

$R_3$ represents a t-butyl group;

$R_4$ represents a hydrogen atom; and

A represents a fragment represented by formula (II):

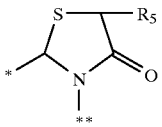
(II)

wherein $R_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

$R_6$ and $R_7$, which may be the same or different, each represents a substituted or unsubstituted lower alkyl group having 1 to 6 carbon atoms, provided that $R_6$ and $R_7$ do not both represent a methyl group or $R_6$ and $R_7$ are taken together to form a substituted or unsubstituted ring which may be a condensed ring; and n represents an integer of 3, or a stereoisomer or optical isomer thereof and a pharmaceutically acceptable salt thereof.

16. A compound according to claim 1, which is represented by formula (I):

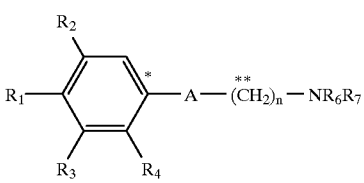
(I)

wherein $R_1$ represents a hydroxyl group, an acyloxy group having 1 to 9 carbon atoms or a lower alkoxy group having 1 to 6 carbon atoms;

$R_2$ represents a t-butyl group;

$R_3$ represents a t-butyl group;

$R_4$ represents a hydrogen atom; and

A represents a fragment represented by formula (II):

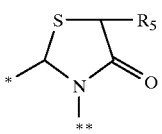
(II)

wherein $R_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

$R_6$, which may be the same or different, represents a substituted or unsubstituted lower alkyl group having 1 to 3 carbon atoms;

R_7 represents a group selected from the set of groups consisting of a 2-(3,4-methylenedioxyphenoxy)ethyl group, a 3-(3,4-methylenedioxyphenoxy)propyl group, a 4-(3,4-methylenedioxy-phenoxy)-n-butyl group, and a 3,4-dimethoxyphenylmethyl group; or —NR_6R_7 represents a group selected from the set of groups consisting of a 4-(N-2-benzothiazolyl-N-methyl-amino)piperidyl group, a 4-phenylmethylpiperidyl group, a 4-(3,4-methylenedioxyphenoxy)piperidyl group, and a 4-(2,3,4-trimethoxyphenylmethyl)piperazinyl group, and n represents an integer of 2, 3, 4 or 5, or a stereoisomer or optical isomer thereof and a pharmaceutically acceptable salt thereof.

17. A compound according to claim 1, which is represented by formula (I):

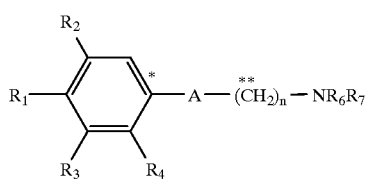

(I)

wherein R_1 represents a hydroxyl group, an acyloxy group having 1 to 9 carbon atoms or a lower alkoxy group having 1 to 6 carbon atoms;

R_2 represents a t-butyl group;

R_3 represents a t-butyl group;

R_4 represents a hydrogen atom; and

A represents a fragment represented by formula (II):

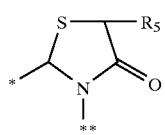

(II)

wherein R_5 represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

R_6, which may be the same or different, represents a substituted or unsubstituted lower alkyl group having 1 to 3 carbon atoms;

R_7 represents a group selected from the set of groups consisting of a 2-(3,4-methylenedioxyphenoxy)ethyl group, a 3-(3,4-methylenedioxyphenoxy)propyl group, a 4-(3,4-methylenedioxy-phenoxy)-n-butyl group, and a 3,4-dimethoxyphenylmethyl group; or —NR_6R_7 represents a group selected from the set of groups consisting of a 4-(N-2-benzothiazolyl-N-methyl-amino)piperidyl group, a 4-phenylmethylpiperidyl group, a 4-(3,4-methylenedioxyphenoxy)piperidyl group, and a 4-(2,3,4-trimethoxyphenylmethyl)piperazinyl group, and n represents an integer of 3, or a stereoisomer or optical isomer thereof and a pharmaceutically acceptable salt thereof.

18. A compound according to claim 1, which is represented by formula (I):

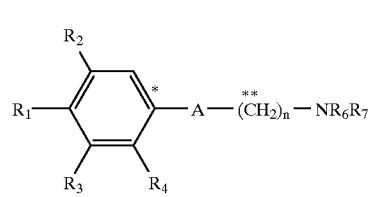

(I)

wherein R_1 represents a hydroxyl group, an acyloxy group having 1 to 9 carbon atoms or a lower alkoxy group having 1 to 6 carbon atoms; R_2 represents a t-butyl group;

R_3 represents a t-butyl group;

R_4 represents a hydrogen atom; and

A represents a fragment represented by formula (II):

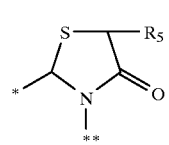

(II)

wherein R_5 represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

R_6 represents a methyl group or an ethyl group;

R_7 represents a group selected from the set of groups consisting of a 2-(3,4-methylenedioxyphenoxy)ethyl group, a 3-(3,4-methylenedioxyphenoxy)propyl group, a 4-(3,4-methylenedioxyphenoxy)-n-butyl group, and a 3,4-dimethoxyphenylmethyl group; or —NR_6R_7 represents a group selected from the set of groups consisting of a 4-(N-2-benzothiazolyl-N-methylamino)piperidyl group, a 4-phenylmethylpiperidyl group, a 4-(3,4-methylenedioxy-phenoxy)piperidyl group, and a 4-(2,3,4-trimethoxyphenyl-methyl)piperazinyl group, and n represents an integer of 2, 3, 4 or 5, or a stereoisomer or optical isomer thereof and a pharmaceutically acceptable salt thereof.

19. A compound according to claim 1, which is represented by formula (I):

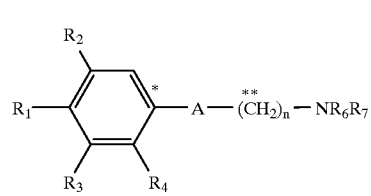

(I)

wherein R_1 represents a hydroxyl group, an acyloxy group having 1 to 9 carbon atoms or a lower alkoxy group having 1 to 6 carbon atoms; R_2 represents a t-butyl group; $R_3$ represents a t-butyl group; $R_4$ represents a hydrogen atom;

A represents a fragment represented by formula (II):

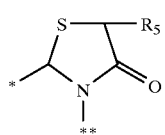

(II)

wherein $R_5$ represents a hydrogen atom, a substituted or unsubstituted lower alkyl group having 1 to 6 carbon atoms, a substituted or unsubstituted lower alkoxy group having 1 to 6 carbon atoms or a substituted or unsubstituted aryl group, or a 5- or 6-membered ring containing two or more oxygen atoms or sulfur atoms, in which case the carbon atom to which it is bonded is a spiro atom;

$R_6$ represents a methyl group or an ethyl group;

$R_7$ represents a group selected from the set of groups consisting of a 2-(3,4-methylenedioxyphen-oxy)ethyl group, a 3-(3,4-methylenedioxyphenoxy)propyl group, a 4-(3,4-methylenedioxyphenoxy)-n-butyl group, and a 3,4-dimethoxyphenylmethyl group; or —$NR_6R_7$ represents a group selected from the set of groups consisting of a 4-(N-2-benzothiazolyl-N-methylamino)piperidyl group, a 4-phenylmethylpiperidyl group, a 4-(3,4-methylenedioxy-phenoxy)piperidyl group, and a 4-(2,3,4-trimethoxyphenyl-methyl)piperazinyl group, and n represents an integer of 3, or a stereoisomer or optical isomer thereof and a pharmaceutically acceptable salt thereof.

20. A compound according to claim 1, which is represented by formula (I):

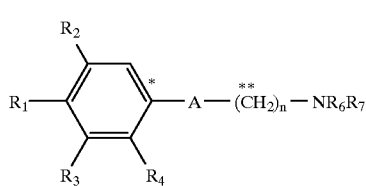

(I)

wherein $R_1$ represents a hydroxyl group, an acyloxy group having 1 to 9 carbon atoms or a lower alkoxy group having 1 to 6 carbon atoms;

$R_2$ represents a t-butyl group;

$R_3$ represents a t-butyl group;

$R_4$ represents a hydrogen atom; and

A represents a fragment represented by formula (II):

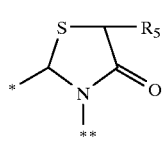

(II)

wherein $R_5$ represents a hydrogen atom, a substituted or unsubstituted lower alkyl group having 1 to 6 carbon atoms, a substituted or unsubstituted lower alkoxy group having 1 to 6 carbon atoms, or a 5- or 6-membered ring containing two or more oxygen atoms or sulfur atoms, in which case the carbon atom to which it is bonded is a spiro atom;

$R_6$ represents a methyl group; $R_7$ represents a group selected from the set of groups consisting of a 2-(3,4-methylene-dioxyphenoxy)ethyl group, a 3-(3,4-methylenedioxyphenoxy)propyl group, a 4-(3,4-methylenedioxyphenoxy)-n-butyl group, and a 3,4-dimethoxyphenylmethyl group; or —$NR_6R_7$ represents a group selected from the set of groups consisting of a 4-(N-2-benzothiazolyl-N-methylamino)piperidyl group, a 4-phenylmethylpiperidyl group, a 4-(3,4-methylenedioxyphenoxy)piperidyl group, and a 4-(2,3,4-trimethoxyphenylmethyl)piperazinyl group, and n represents an integer of 2, 3, 4 or 5, or a stereoisomer or optical isomer thereof and a pharmaceutically acceptable salt thereof.

21. A compound according to claim 1, which is represented by formula (I):

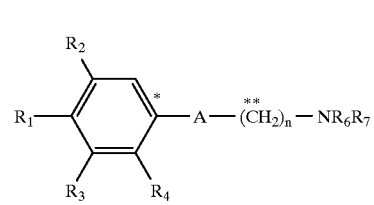

(I)

wherein $R_1$ represents a hydroxyl group, an acyloxy group having 1 to 9 carbon atoms or a lower alkoxy group having 1 to 6 carbon atoms; $R_2$ represents a t-butyl group;

$R_3$ represents a t-butyl group; $R_4$ represents a hydrogen atom; A represents a fragment represented by formula (II):

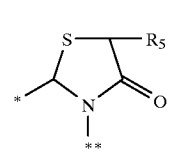

(II)

wherein $R_5$ represents a hydrogen atom, a substituted or unsubstituted lower alkyl group having 1 to 6 carbon atoms or a substituted or unsubstituted lower alkoxy group having 1 to 6 carbon atoms, or a 5- or 6-membered ring containing two or more oxygen atoms or sulfur atoms, in which case the carbon atom to which it is bonded is a spiro atom;

$R_6$ represents a methyl group; $R_7$ represents a group selected from the set of groups consisting of a 2-(3,4-methylenedioxyphenoxy)ethyl group, a 3-(3,4-methylenedioxyphenoxy)propyl group, a 4-(3,4-methylenedioxyphenoxy)n-butyl group, and a 3,4-dimethoxyphenylmethyl group; or —$NR_6R_7$ represents a group selected from the set of groups consisting of a 4-(N-2-benzothiazolyl-N-methylamino)piperidyl group, a 4-phenylmethylpiperidyl group, a 4-(3,4-methylenedioxyphenoxy)piperidyl group, and a 4-(2,3,4-trimethoxyphenylmethyl)piperazinyl group, and n represents an integer of 3, or a stereoisomer or optical isomer thereof and a pharmaceutically acceptable salt thereof.

22. A compound according to claim 1, which is selected from the group of compounds consisting of 2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, (+)-2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, (−)-2-(3,5-di-t-butyl-4-hydroxy-phenyl)-3-[3-[N-methyl-N[2-(3,4-methylenedioxy-phenoxy)ethyl]amino]propyl]-1,3-thiazolidin-4-one, 2-(3,5-di-t-butyl-4-hydroxyphenyl)-3-[3-[N-ethyl-N-[2-(3,4-methylenedioxy-phenoxy)ethyl]amino]propyl]-1,3-thiazolidin-4-one, 2-(3,5-di-t-butyl-4-hydroxyphenyl)-3-[4-[N-methyl-N-[2-(3,4-methylenedioxyphenoxy)ethyl]amino]butyl]-1,3-thiazolidin-4-one, 2-(3,5-di-t-butyl-4-hydroxyphenyl)-3-[5-[N-methyl-N-[2-(3,4-methylenedioxyphenoxy)ethyl]amino]pentyl]-1,3-thiazolidin-4-one, 2-(3,5-di-t-butyl-4-hydroxyphenyl)-3-[3-(3,4-methylenedioxyphenoxy)propyl]amino]propyl]-1,3-thiazolidin-4-one, 2-(3,5-diisopropyl-4-hydroxyphenyl)-3-[3-[N-methyl-N-[2-(3,4-methylenedioxyphenoxy)ethyl]amino]propyl]-1,3-thiazolidin-4-one, 2-(3,5-di-t-butyl-4-hydroxyphenyl)-3-[3-[1-[4-(2,3,4-trimethoxybenzyl)piperazinyl]]propyl]-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (−)-2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (+)-2,5-cis-2-(3,5-di-t-butyl 4-hydroxyphenyl)-3-[3-[N-methyl-N-[2-(3,4-methylenedioxyphenoxy)ethyl]amino]propyl]-5-methyl-1,3-thiazolidin-4-one, 2,5-trans-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 2-(3,5-di-t-butyl-4-hydroxyphenyl)-3-[3-[N-methyl-N-[4-(3,4-methylenedioxyphenoxy)butyl]amino]propyl]-1,3-thiazolidin-4-one, 5-(3,5-di-t-butyl-4-hydroxyphenyl)-1-[3-[N-methyl-N-[2-(3,4-methylenedioxyphenoxy)ethyl]amino]propyl]imidazole, 2-(3,5-di-t-butyl-4-hydroxyphenyl)-3-[3-[N-methyl-N-[2-(3,4-methylenedioxyphenoxy)ethyl]amino]propyl]-1,3-thiazolidin-4-thione, 5-(3,5-di-t-butyl-4-hydroxy-phenyl)-4-ethyl-2-[3-[N-methyl-N-[2-(3,4-methylenedioxyphenoxy)ethyl]amino]propyl]-1,2,4-triazol-3-one, 3-(3,5-di-t-butyl-4-hydroxyphenyl)-5-[3-[N-methyl-N-[2(3,4-methylenedioxyphenoxy)ethyl]amino]propoxy]-1,2,4-oxadiazole, 2-(3,5-di-t-butyl-4-hydroxyphenyl)-3-[3-[N-methyl-N-[2-(3,4-methylenedioxyphenoxy)ethyl]amino]propyl]-5-(2-hydroxy-ethyl)-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-ethoxycarbonylmethyl-1,3-thiazolidin-4-one, N-[3-[N-methyl-N-[2-(3,4-methylenedioxyphenoxy)ethyl]amino]propyl]-3,5-di-t-butyl-4-hydroxybenzenesulfonamide, 2-(3,5-di-t-butyl-4-hydroxyphenyl)-3-[3-[N-methyl-N-[2-(3,4-methylenedioxyphenoxy)ethyl]amino]propyl]-5-methoxy-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-isopropoxycarbonylmethyl-1,3-thiazolidin-4-one, 2-(3,5-di-t-butyl-4-hydroxyphenyl)-3-[3-[N-methyl-N-[2-(3,4-methylenedioxy-phenoxy)ethyl]amino]propyl]-5-(2-hydroxyethoxy)-1,3-thiazolidin-4-one, spiro[2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one-5,2'-[1,3]dioxolane], 2-(3,5-di-t-butyl-4-hydroxyphenyl)-3-[3-[N-methyl-N[2(3,4methylenedioxyphenoxy)ethyl]amino]propyl]-5-N,N-dimethylcarbamoylmethyl-1,3-thiazolidin-4-one, 2-(3,5-di-t-butyl-4-hydroxyphenyl)-3-[3-[1-(4-benzyl)piperidyl]propyl]-1,3-thiazolidin-4-one, and 2-(3,5-di-t-butyl-4-hydroxyphenyl)-3-[3-[1-[4-(3,4-methylenedioxyphenoxy)piperidyl]]propyl]-1,3-thiazolidin-4-one, and a pharmaceutically acceptable salt thereof.

23. A compound according to claim 1, which is selected from the group of compounds consisting of 2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, (+)-2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, (−)-2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, 2-(3,5-di-t-butyl-4-hydroxyphenyl)-3-[3-[N-ethyl-N-[2-(3,4-methylenedioxyphenoxy)ethyl]amino]propyl]-1,3-thiazolidin-4-one, 2-(3,5-di-t-butyl-4-hydroxyphenyl)-3-[3-[N-methyl-N-[3-(3,4-methylenedioxyphenoxy)propyl]amino]propyl]-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (−)-2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (+)-2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 2,5-trans-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 5-(3,5-di-t-butyl-4-hydroxyphenyl)-1-[3-[N-methyl-N[2-(3,4-methylenedioxyphenoxy)ethyl]amino]propyl]imidazole, 2-(3,5-di-t-butyl-4-hydroxyphenyl)-3-[3-[N-methyl-N-[2-(3,4-methylenedioxyphenoxy)ethyl]amino]propyl]-1,3-thiazolidin-4-thione, 5-(3,5-di-t-butyl-4-hydroxyphenyl)-4-ethyl-2-[3-[N-methyl-N-[2-(3,4-methylenedioxyphenoxy)ethyl]amino]propyl]-1,2,4-triazol-3-one, 3-(3,5-di-t-butyl-4-hydroxyphenyl)-5-[3-[N-methyl-N-[2-(3,4-methylenedioxyphenoxy)ethyl]amino]propoxy]-1,2,4-oxadiazole, 2-(3,5-di-t-butyl-4-hydroxyphenyl)-3-[3-[N-methyl-N-[2-(3,4-methylenedioxyphenoxy)ethyl]amino]propyl]-5-(2-hydroxy-ethyl)- 1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-ethoxycarbonylmethyl-1,3-thiazolidin-4-one, N-[3-[N-methyl-N-[2-(3,4-methylenedioxyphenoxy)ethyl]amino]propyl]-3,5-di-t-butyl-4-hydroxybenzenesulfonamide, 2-(3,5-di-t-butyl-4-hydroxyphenyl)-3-[3-[N-methyl-N-[2-(3,4-methylenedioxyphenoxy)ethyl]amino]propyl]-5-methoxy-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-isopropoxycarbonylmethyl-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-(2-hydroxyethoxy)-1,3-thiazolidin-4-one, spiro[2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one-5,2'-[1,3]dioxolane], 2-(3,5-di-t-butyl-4-hydroxy-phenyl)-3-[3-[N-methyl-N-[2-(3,4-methylenedioxy-phenoxy)ethyl]amino]propyl]-5-N,N-dimethylcarbamoylmethyl-1,3-thiazolidin-4-one, and 2-(3,5-di-t-butyl-4-hydroxy-phenyl)-3-[3-[1-(4-benzyl)piperidyl]propyl]-1,3-thiazolidin-4-one, and a pharmaceutically acceptable salt thereof.

24. 2-(3,5-Di-t-butyl-4-hydroxyphenyl)-3-[3-[N-methyl-N-[2-(3,4-methylenedioxyphenoxy)ethyl]amino]propyl]-1,3-thiazolidin-4-one according to claim 1 and a pharmaceutically acceptable salt thereof or an optical isomer thereof.

25. (+)-2-(3,5-Di-t-butyl-4-hydroxyphenyl)-3-[3-[N-methyl-N-[2-(3,4-methylenedioxyphenoxy)ethyl]amino]propyl]-1,3-thiazolidin-4-one according to claim 1 and a pharmaceutically acceptable salt thereof.

26. (−)-2-(3,5-Di-t-butyl-4-hydroxyphenyl)-3-[3-[N-methyl-N-[2-(3,4-methylenedioxyphenoxy)ethyl]amino]propyl]-1,3-thiazolidin-4-one according to claim 1 and a pharmaceutically acceptable salt thereof.

27. 2-(3,5-Di-t-butyl-4-hydroxyphenyl)-3-[3-[N-methyl-N-[2-(3,4-methylenedioxyphenoxy)ethyl]amino]propyl]-5-methyl-1,3-thiazolidin-4-one according to claim 1 and a pharmaceutically acceptable salt thereof or a stereoisomer or optical isomer thereof.

28. 2,5-Cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one according to claim 1 and a pharmaceutically acceptable salt thereof or an optical isomer thereof.

29. 2,5-Trans-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one according to claim 1 and a pharmaceutically acceptable salt thereof or an optical isomer thereof.

30. (−)-2,5-Cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one according to claim 1 and a pharmaceutically acceptable salt thereof.

31. (+)-2,5-Cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one according to claim 1 and a pharmaceutically acceptable salt thereof.

32. A compound represented by formula (I):

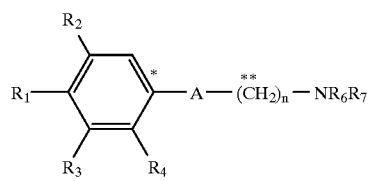

(I)

wherein $R_1$ represents a hydrogen atom; $R_2$ and $R_3$, which may be the same or different, each represents a lower alkyl group having 1 to 6 carbon atoms;

$R_4$ represents a hydrogen atom, a lower alkyl group having 1 to 6 carbon atoms; A represents a fragment represented by formula (II):

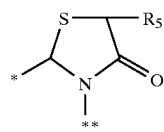

(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B (III)

wherein B represents a fragment selected from the following group of fragments represented by formulae (IV), (V), (VI), (VII), (VIII), (X), (XI), (XII), (XIII), (XIV), (XV), and (XVI):

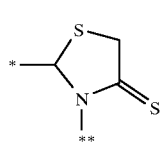

(IV)

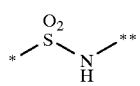

(V)

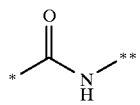

(IX)

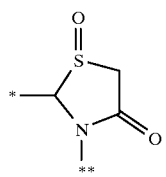

(X)

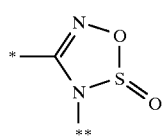

(XI)

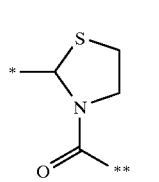

(XII)

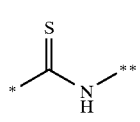

(XIII)

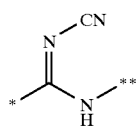

(XIV)

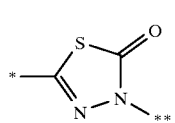

(XV)

(XVI)

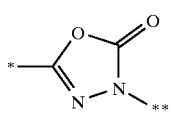

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, provided that $R_6$ and $R_7$ do not both represent a methyl group or $R_6$ and $R_7$ are taken together to form a substituted or unsubstituted ring which may be a condensed ring; and n represents an integer of 2, 3, 4, 5 or 6, or a stereoisomer or optical isomer thereof and a pharmaceutically acceptable salt thereof.

33. The compound as claimed in claim 31, wherein $R_2$ and $R_3$ are each a t-butyl group.

34. A composition for treating ischemic diseases comprising an effective amount of a compound represented by formula (I):

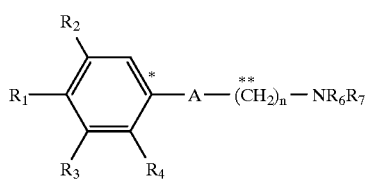

(I)

wherein $R_1$ represents a hydrogen atom, a hydroxyl group, an acyloxy group having 1 to 9 carbon atoms or a lower alkoxy group having 1 to 6 carbon atoms; $R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms; $R_4$ represents a hydrogen atom, a lower alkyl group having 1 to 6 carbon atoms; A represents a fragment represented by formula (II):

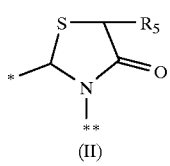

(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B (III)

wherein B represents a fragment selected from the following group of fragments represented by formulae (IV), (V), (VI), (VII), (VIII), (X), (XI), (XII), (XIII), (XIV), (XV), and (XVI):

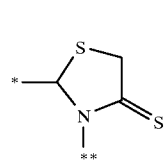

(IV)

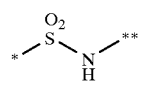

(V)

(VI)

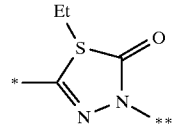

(VII)

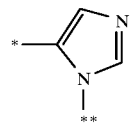

(VIII)

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, except the case in which both $R_6$ and $R_7$ are a methyl group, or $R_6$ and $R_7$ are taken together to form a substituted or unsubstituted ring which may be a condensed ring; and n represents an integer of 2, 3, 4, 5 or 6; or a stereoisomer, an optical isomer thereof, or a pharmaceutically acceptable salt thereof; and a pharmacologically acceptable carrier with the proviso that said compound is not 1,2-Bis(2-phenylthiazolidin-4-on-3-yl)ethane.

35. A composition for treating ischemic heart diseases having the formula according to claim 34 or a stereoisomer or optical isomer thereof or a pharmaceutically acceptable salt thereof and a pharmacologically acceptable carrier.

36. A method of treating ischemic diseases comprising administering to a person in need thereof, an effective amount of a compound represented by formula (I):

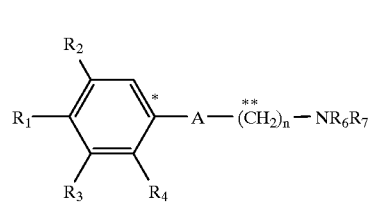

(I)

wherein $R_1$ represents a hydrogen atom, a hydroxyl group, an acyloxy group having 1 to 9 carbon atoms or a lower alkoxy group having 1 to 6 carbon atoms; $R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms; $R_4$ represents a hydrogen atom, a lower alkyl group having 1 to 6 carbon atoms; A represents a fragment represented by formula (II):

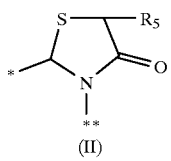

(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B     (III)

wherein B represents a fragment selected from the following group of fragments represented by formulae (IV), (V), (VI), (VII), (VIII), (X), (XI), (XII), (XIII), (XIV), (XV), and (XVI):

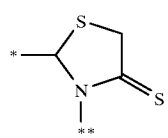

(IV)

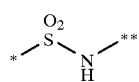

(V)

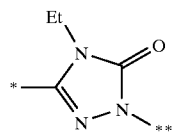

(VI)

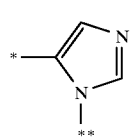

(VII)

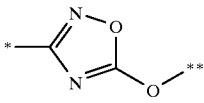

(VIII)

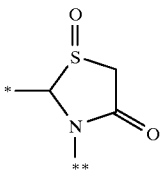

(X)

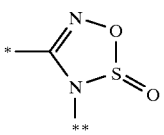

(XI)

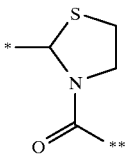

(XII)

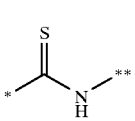

(XIII)

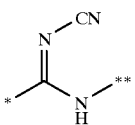

(XIV)

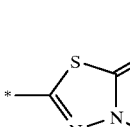

(XV)

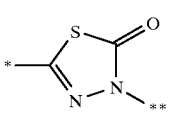

(XVI)

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, except the case in which both $R_6$ and $R_7$ are a methyl group, or $R_6$ and $R_7$ are taken together to form a substituted or unsubstituted ring which may be a condensed ring; and n represents an integer of 2, 3, 4, 5 or 6; or a stereoisomer, an optical isomer thereof, or a pharmaceutically acceptable salt thereof; and a pharmacologically acceptable carrier.

37. The method according to claim 36, wherein said ischemic disease is angina pectoris.

38. The method according to claim 36, wherein said ischemic disease is hypertension.

39. The method according to claim 36, wherein said ischemic disease is arrhythmia.

40. The method according to claim 36, wherein said compound results in coronary vasodilation.

41. A method of preventing cardiac infarction comprising administering to a person in need thereof comprising an effective amount of a compound represented by formula (I):

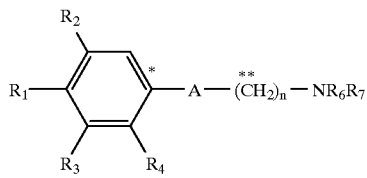

(I)

wherein $R_1$ represents a hydrogen atom, a hydroxyl group, an acyloxy group having 1 to 9 carbon atoms or a lower alkoxy group having 1 to 6 carbon atoms; $R_2$ and $R_3$, which may be the same or different, each represents a hydrogen atom, a hydroxyl group, a halogen atom, a lower alkyl group having 1 to 6 carbon atoms or a lower alkoxy group having 1 to 6 carbon atoms; $R_4$ represents a hydrogen atom, a lower alkyl group having 1 to 6 carbon atoms; A represents a fragment represented by formula (II):

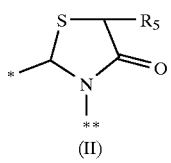

(II)

wherein $R_5$ represents a hydrogen atom, a substituted or unsubstituted lower alkyl group having 1 to 6 carbon atoms, a substituted or unsubstituted lower alkenyl group having 1 to 6 carbon atoms, a substituted or unsubstituted alkoxy group having 1 to 6 carbon atoms, a substituted or unsubstituted aryl group or a substituted or unsubstituted heterocyclic group, or a 5- or 6-membered ring containing two or more oxygen atoms or sulfur atoms, in which case the carbon atom to which it is bonded is a spiro atom; or a fragment represented by formula (III):

B  (III)

wherein B represents a fragment selected from the following group of fragments represented by formulae (IV), (V), (VI), (VII), (VIII), (X), (XI), (XII), (XIII), (XIV), (XV), and (XVI):

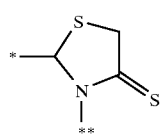

(IV)

-continued

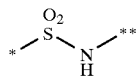

(V)

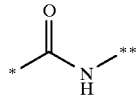

(IX)

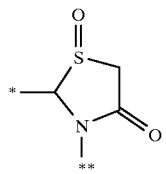

(X)

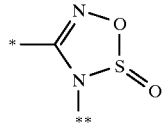

(XI)

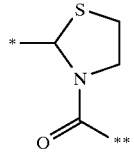

(XII)

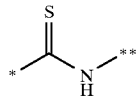

(XIII)

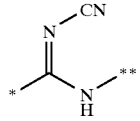

(XIV)

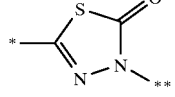

(XV)

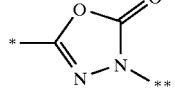

(XVI)

$R_6$ and $R_7$, which may be the same or different, each represents a hydrogen atom, a substituted or unsubstituted lower alkyl group having 1 to 6 carbon atoms, a substituted or unsubstituted lower alkenyl group having 1 to 6 carbon atoms, a substituted or unsubstituted aryl group or a substituted or unsubstituted heterocyclic group, except the case in which both $R_6$ and $R_7$ are a methyl group, or $R_6$ and $R_7$ are taken together to form a substituted or unsubstituted ring which may be a condensed ring; and n represents an integer of 2, 3, 4, 5 or 6; or a stereoisomer, an optical isomer thereof, or a pharmaceutically acceptable salt thereof; and a pharmacologically acceptable carrier.

42. The method according to claim 36, wherein said disease is an ischemic cerebrovascular disease.

43. The method according to claim 42, wherein said ischemic cerebrovascular disease is cerebral infarction.

44. The method according to claim 36, wherein said compound results in enhancing cerebral circulation.

45. The method according to claim 36, wherein said compound is a cerebral protecting agent.

46. The composition according to claim 34, wherein said compound is selected from the group consisting of 2-(3,5-di-t-butyl-4-hydroxyphenyl)-3-[3-[N-methyl-N-[2-(3,4-methylenedioxyphenoxy)ethyl]amino]-propyl]-1,3-thiazolidin-4-one, (+)-2-(3,5-di-t-butyl-4-hydroxyphenyl)-3-[3-[N-methyl-N-[2-(3,4-methylenedioxy-phenoxy)ethyl]amino]propyl]-1,3-thiazolidin-4-one, (−)-2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one, 2-(3,5-di-t-butyl-4-hydroxyphenyl)-3-[3-[N-ethyl-N-[2(3,4-methylenedioxyphenoxy)ethyl]amino]propyl]-1,3-thiazolidin-4-one, 2-(3,5-di-t-butyl-4-hydroxyphenyl)-3-[4-[N-methyl-N-[2-(3,4-methylenedioxyphenoxy)ethyl]amino]-butyl]-1,3-thiazolidin-4-one, 2-(3,5-di-t-butyl-4-hydroxyphenyl)-3-[5-[N-methyl-N-[2-(3,4-methylenedioxyphenoxy)ethyl]amino]pentyl]-1,3-thiazolidin-4-one, 2-(3,5-di-t-butyl-4-hydroxyphenyl)-3-[3-[N-methyl-N-[3-(3,4-methylenedioxyphenoxy)propyl]amino]propyl]-1,3-thiazolidin-4-one, 2-(3,5-diisopropyl-4-hydroxyphenyl)-3-[3-[N-methyl-N-[2-(3,4-methylenedioxyphenoxy)ethyl]amino]propyl]-1,3-thiazolidin-4-one, 2-(3,5-di-t-butyl-4-hydroxyphenyl)-3-[3-[1-[4-(2,3,4-trimethoxybenzyl)piperazinyl]]propyl]-1,3-thiazolidin-4-one, 2-(3,5-di-t-butyl-4-hydroxyphenyl)-3-[3-[N-methyl-N-[2-(3,4-methylenedioxyphenoxy)ethyl]amino]-propyl]-5-methyl-1,3-thiazolidin-4-one, 2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (−)-2,5-cis-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, (+)-2,5-cis-2-(3,5-di-t-butyl-4-hydroxyphenyl)-3-[3-[N-methyl-N-[2 -(3,4-methylenedioxyphenoxy)ethyl]amino]propyl]-5-methyl-1,3-thiazolidin-4-one, 2,5-trans-2-(3,5-di-t-butyl-4-hydroxyphenyl)-3-[3-[N-methyl-N-[2-(3,4-methylenedioxyphenoxy)ethyl]amino]propyl]-5-methyl-1,3-thiazolidin-4-one, 2-(3,5-di-t-butyl-4-hydroxyphenyl)-3-[3-N-methyl-N-[4-(3,4-methylenedioxyphenoxy)butyl]amino]propyl]-1,3-thiazolidin-4-one, 5-(3,5-di-t-butyl-4-hydroxyphenyl)-1-[3-[N-methyl-N-[2-(3,4-methylenedioxyphenoxy)ethyl]amino]-propyl]imidazole, 2-(3,5-di-t-butyl-4-hydroxyphenyl)-3-[3-[N-methyl-N-[2-(3,4-methylenedioxyphenoxy)ethyl]amino]-propyl]-1,3-thiazolidin-4-thione, 5-(3,5-di-t-butyl-4-hydroxyphenyl)-4-ethyl-2-[3-[N-methyl-N-[-2-(3,4-methylenedioxyphenoxy)ethyl]amino]propyl]-1,2,4-triazol-3-one, 3-(3,5-di-t-butyl-4-hydroxyphenyl)-5-[3-[N-methyl-N-[2-(3,4-methylenedioxyphenoxy)ethyl]amino]propoxy]-1,2,4-oxadiazole, 2-(3,5-di-t-butyl-4-hydroxyphenyl)-3-[3-[N-methyl-N-[2-(3,4-methylenedioxyphenoxy)ethyl]amino]propyl]-5-(2-hydroxyethyl)-1,3-thiazolidin-4-one, 2-(3,5-di-t-butyl-4-hydroxyphenyl)-3-[3-[N-methylenedioxyphenoxy)ethyl]amino]propyl]-5-ethoxycarbonylmethyl-1,3-thiazolidin-4-one, N-[3-[N-methyl-N-[2-(3,4-methylenedioxyphenoxy)ethyl]amino]propyl]-3,5-di-t-butyl-4-hydroxybenzenesulfonamide, 2-(3,5-di-t-butyl-4-hydroxyphenyl)-3-[3-[N-methyl-N-[2-(3,4-methylenedioxyphenoxy)ethyl]amino]propyl]-5-methoxy-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5 -isopropoxycarbonylmethyl-1,3-thiazolidin-4-one, 2-(3,5-di-t-butyl-4-hydroxyphenyl)-3-[3-[N-methyl-N-[2-(3,4-methylenedioxyphenoxy)ethyl]amino]propyl]-5-(2-hydroxyethoxy)-1,3-thiazolidin-4-one, spiro[2-(3,5-di-t-butyl-4-hydroxyphenyl)-3-[3-[N-methyl-N-[2-(3,4-methylenedioxyphenoxy)ethyl]amino]propyl]-1,3-thiazolidin-4-one-5,2'-[1,3]dioxolane], 2-(3,5-di-t-butyl-4-hydroxyphenyl)-3-[3-[N-methyl-N-[2-(3,4-methylenedioxyphenoxy)ethyl]amino]-propyl]-5-N,N-dimethylcarbamoylmethyl-1,3-thiazolidin-4-one, 2-(3,5-di-t-butyl-4-hydroxyphenyl)-3-[3-[1-(4-benzyl)piperidyl]propyl]-1,3-thiazolidin-4-one, and 2-(3,5-di-t-butyl-4-hydroxyphenyl)-3-[3-[1-[4-(3,4-methylenedioxy-phenoxy)piperidyl]]propyl]-1,3-thiazolidin-4-one, or a pharmaceutically acceptable salt thereof and a pharmacologically acceptable carrier.

\* \* \* \* \*